(12) United States Patent
Firooznia et al.

(10) Patent No.: US 8,263,656 B2
(45) Date of Patent: Sep. 11, 2012

(54) SUBSTITUTED AMINOTETRALINES

(75) Inventors: Fariborz Firooznia, Florham Park, NJ (US); Paul Gillespie, Westfield, NJ (US); Robert Alan Goodnow, Jr., Gillette, NJ (US); Tai-An Lin, Pequannock, NJ (US); Achyutharao Sidduri, Livingston, NJ (US); Sung-Sau So, Verona, NJ (US); Jenny Tan, New Providence, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 464 days.

(21) Appl. No.: 12/540,839

(22) Filed: Aug. 13, 2009

(65) Prior Publication Data

US 2010/0041713 A1 Feb. 18, 2010

Related U.S. Application Data

(60) Provisional application No. 61/089,102, filed on Aug. 15, 2008.

(51) Int. Cl.
A61K 31/195 (2006.01)
C07C 317/12 (2006.01)

(52) U.S. Cl. ........ 514/562; 562/427

(58) Field of Classification Search .......... None
See application file for complete search history.

(56) References Cited

U.S. PATENT DOCUMENTS

| | | | |
|---|---|---|---|
| 3,899,529 | A | 8/1975 | Witzel |
| 4,868,331 | A | 9/1989 | Niewöhner et al. |
| 4,921,998 | A | 5/1990 | Niewöhner et al. |
| 7,226,951 | B2 | 6/2007 | Vasudevan et al. |
| 2006/0154965 | A1 | 7/2006 | Harris et al. |

FOREIGN PATENT DOCUMENTS

| | | |
|---|---|---|
| DE | 4411856 | 1/1994 |
| EP | 0 253 257 | 1/1988 |
| EP | 0 405 602 | 1/1991 |
| EP | 0657422 | 6/1995 |
| WO | WO 92/01675 | 2/1992 |
| WO | WO 00/16798 | 3/2000 |
| WO | WO 2005/040114 | 5/2005 |
| WO | WO 2005/054232 | 6/2005 |
| WO | WO 2006/034418 | 3/2006 |
| WO | WO 2006/091674 | 8/2006 |

OTHER PUBLICATIONS

U.S. Appl. No. 12/497,807, Chen et al., Not yet published, filed Jul. 6, 2009.
U.S. Appl. No. 12/540,804, Blanc et al., Not yet published, Filed Aug. 13, 2009.
U.S. Appl. No. 12/540,839, Firooznia et al., Not yet published, filed Aug. 13, 2009.
U.S. Appl. No. 12/540,780, Blanc et al., Not yet published, filed Aug. 13, 2009.
U.S. Appl. No. 61/222,235, Firooznia et al., Not published, Filed Jul. 1, 2009.
U.S. Appl. No. 61/222,182, Chen et al., Not published, filed Jul. 1, 2009.
U.S. Appl. No. 61/222,262, Firooznia et al., Not published, filed Jul. 1, 2009.
Anderson et al., J. Am. Chem. Soc., 128, pp. 10694-10695 (2006).
Walsh, D.A., J. Medicinal Chem., 21, pp. 582-585 (1978).
Feixas et al., Bioorganic & Medicinal Chemistry Letter, 11, pp. 2687-2690 (2001).
Gilbert, E.E., Synthesis, 1, pp. 3-10 (1969).
Cherney et al., J. Med. Chem., 46, pp. 1811-1823 (2003).
Sugimoto et al., Eur. J. Pharmacol., 524, pp. 30-37 (2005).
Ulven Trond et al, "Targeting the prostaglandin D2 receptors DP and CRTH2 for treatment of inflammation" Current Topics in Medicinal Chemistry 6:13 (2006) 1427-1444 XP008104082.

*Primary Examiner* — Paul A Zucker
(74) *Attorney, Agent, or Firm* — George W. Johnston; Dennis P. Tramaloni; Brian C. Remy

(57) ABSTRACT

The invention is concerned with the compounds of formula I:

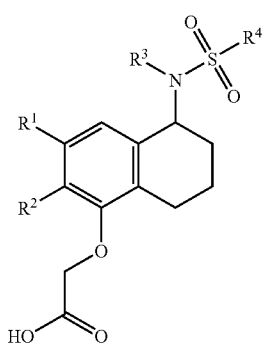

and pharmaceutically acceptable salts and esters thereof, wherein $R^1$-$R^4$ are defined in the detailed description and claims. In addition, the present invention relates to methods of manufacturing and using the compounds of formula I as well as pharmaceutical compositions containing such compounds. The compounds of formula I are antagonists at the CRTH2 receptor and may be useful in treating diseases and disorders associated with that receptor such as asthma.

26 Claims, No Drawings

SUBSTITUTED AMINOTETRALINES

PRIORITY TO RELATED APPLICATIONS

This application claims the benefit of U.S. Provisional Application No. 61/089,102, filed Aug. 15, 2008, which is hereby incorporated by reference in its entirety.

BACKGROUND OF THE INVENTION

The present invention relates to novel substituted (5-amino-5,6,7,8-tetrahydro-naphthalene-1-yloxy)-acetic acids, their manufacture, pharmaceutical compositions containing them and their use as CRTH2 antagonists.

Prostaglandin $D_2$ (PGD2) is the major prostanoid produced by activated mast cells and has been implicated in the pathogenesis of allergic diseases such as allergic asthma and atopic dermatitis. Chemoattractant Receptor-homologous molecule expressed on T-helper type cells (CRTH2) is one of the prostaglandin $D_2$ receptors and is expressed on the effector cells involved in allergic inflammation such as T helper type 2 (Th2) cells, eosinophils, and basophils (Nagata et al., *FEBS Lett* 459: 195-199, 1999). It has been shown to mediate PGD2-stimulated chemotaxis of Th2 cells, eosinophils, and basophils (Hirai et al., *J Exp Med* 193: 255-261, 2001). Moreover, CRTH2 mediates the respiratory burst and degranulation of eosinophils (Gervais et al., *J Allergy Clin Immunol* 108: 982-988, 2001), induces the production of proinflammatory cytokines in Th2 cells (Xue et al., *J Immunol* 175: 6531-6536), and enhances the release of histamine from basophils (Yoshimura-Uchiyama et al., *Clin Exp Allergy* 34:1283-1290). Sequence variants of the gene encoding CRTH2, which differentially influence its mRNA stability, are shown to be associated with asthma (Huang et al., *Hum Mol Genet* 13, 2691-2697, 2004). Increased numbers of circulating T cells expressing CRTH2 have also been correlated with severity of atopic dermatitis (Cosmi et al., *Eur J Immunol* 30, 2972-2979, 2000). These findings suggest that CRTH2 plays a proinflammatory role in allergic diseases. Therefore, antagonists of CRTH2 are believed to be useful for treating disorders such as asthma, allergic inflammation, COPD, and atopic dermatitis.

SUMMARY OF THE INVENTION

The invention is concerned with the compounds of formula I:

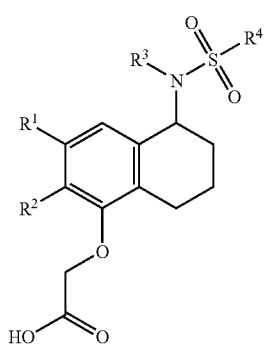

and pharmaceutically acceptable salts and esters thereof, wherein $R^1$-$R^4$ are defined in the detailed description and claims. In addition, the present invention relates to methods of manufacturing and using the compounds of formula I as well as pharmaceutical compositions containing such compounds. The compounds of formula I are antagonists at the CRTH2 receptor and may be useful in treating diseases and disorders associated with that receptor such as asthma.

DETAILED DESCRIPTION OF THE INVENTION

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the variables $R^1$, $R^2$, $R^3$ and $R^4$ of formula I refer to moieties that are attached to the core structure of formula I by a covalent bond.

In reference to a particular moiety with one or more hydrogen atoms, the term "substituted" refers to the fact that at least one of the hydrogen atoms of that moiety is replaced by another substituent or moiety. For example, the term "lower alkyl substituted by halogen" refers to the fact that one or more hydrogen atoms of a lower alkyl (as defined below) is replaced by one or more halogen atoms (e.g., trifluoromethyl, difluoromethyl, fluoromethyl, chloromethyl, etc.).

The term "optionally substituted" refers to the fact that one or more hydrogen atoms of a moiety (with one or more hydrogen atoms) can be, but does not necessarily have to be, substituted with another substituent.

The term "alkyl" refers to an aliphatic straight-chain or branched-chain saturated hydrocarbon moiety having 1 to 20 carbon atoms. In particular embodiments the alkyl has 1 to 10 carbon atoms.

The term "lower alkyl" refers to an alkyl moiety having 1 to 7 carbon atoms. In particular embodiments the lower alkyl has 1 to 4 carbon atoms and in other particular embodiments the lower alkyl has 1 to 3 carbon atoms. Examples of lower alkyls include methyl, ethyl, propyl, isopropyl, butyl, isobutyl, sec-butyl and tert-butyl.

The term "lower cycloalkyl" refers to a saturated or partly unsaturated non-aromatic hydrocarbon ring moiety having 3 to 7 carbon atoms bonded together to form a ring structure. Examples of cycloalkyls include cyclopropyl, cyclobutyl, cyclopentyl, cyclohexyl and cycloheptyl.

The term "lower alkoxy" refers to the moiety —O—R, wherein R is lower alkyl as defined previously. Examples of lower alkoxy moieties include methoxy, ethoxy, n-propoxy, isopropoxy, n-butoxy, isobutoxy, sec-butoxy and tert-butoxy.

The term "lower alkanoyl" refers to the moiety —C(O)—R, wherein R is lower alkyl as defined previously. An example of a lower alkanoyl is acetyl.

The term "lower alkylsulfanyl" refers to the moiety —S—R, wherein R is lower alkyl as defined previously. Examples of lower alkylsulfanyls include methylsulfanyl and ethylsulfanyl.

The term "lower cycloalkylsulfanyl" refers to the moiety —S—R, wherein R is lower cycloalkyl as defined previously. Examples of lower cycloalkylsulfanyls include cyclopropylsulfanyl, cyclobutylsulfanyl and cyclopentylsulfanyl.

The term "lower alkylsulfinyl" refers to the moiety —S(O)—R, wherein R is lower alkyl as defined previously. Examples of lower alkylsulfinyls include methylsulfinyl and ethylsulfinyl.

The term "lower cycloalkylsulfinyl" refers to the moiety —S(O)—R, wherein R is lower cycloalkyl as defined previously. Examples of lower cycloalkylsulfinyls include cyclopropylsulfinyl, cyclobutylsulfinyl and cyclopentylsulfinyl.

The term "lower alkylsulfonyl" refers to the moiety —S(O)2-R, wherein R is lower alkyl as defined previously. Examples of lower alkylsulfonyls include methylsulfonyl and ethylsulfonyl.

The term "lower cycloalkylsulfonyl" refers to the moiety —S(O)2-R, wherein R is lower cycloalkyl as defined previously. Examples of lower cycloalkylsulfonyls include cyclopropylsulfonyl, cyclobutylsulfonyl and cyclopentylsulfonyl.

The term "halogen" refers to a moiety of fluoro, chloro, bromo or iodo.

Unless otherwise indicated, the term "hydrogen" or "hydro" refers to the moiety of a hydrogen atom (—H) and not $H_2$.

Unless otherwise indicated, the term "a compound of the formula" or "a compound of formula" or "compounds of the formula" or "compounds of formula" refers to any compound selected from the genus of compounds as defined by the formula (including any pharmaceutically acceptable salt or ester of any such compound).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be effected in the course of the manufacturing process or can take place i.e. as a consequence of hygroscopic properties of an initially anhydrous compound of formula I (hydration).

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

In detail, the present invention relates to the compounds of formula I:

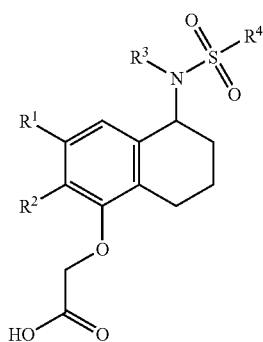

I and pharmaceutically acceptable salts and esters thereof, wherein:

$R^1$ is hydrogen, halogen, methoxy, or phenyl; and $R^2$ is hydrogen, halogen, or alkyl; with the proviso that $R^1$ and $R^2$ are not both hydrogen;

$R^3$ is hydrogen or methyl; and $R^4$ is phenyl or pyridine substituted by one or two substituents independently selected from the group consisting of:
(1) halogen;
(2) lower alkyl optionally substituted by halogen,
(3) lower alkanoyl;
(4) lower alkoxy;
(5) lower alkylsulfanyl, lower alkylsulfinyl, or lower alkylsulfonyl
(6) lower cycloalkylsulfanyl, lower cycloalkylsulfinyl, or lower cycloalkylsulfonyl; and
(7) phenyl or pyridine, wherein said phenyl or pyridine is optionally substituted by lower alkyl, lower alkylsulfanyl, lower alkylsulfonyl, lower cycloalkylsulfanyl, or lower cycloalkylsulfonyl.

Unless indicated otherwise, the genus of formula I and any subgenera thereof encompass all possible stereoisomers (i.e., (R)-enantiomers and (S)-enantiomers) as well as racemic and scalemic mixtures thereof. In one embodiment of the invention, the compounds of formula I are (R)-enantiomers or pharmaceutically acceptable salts or esters thereof as depicted in the following subgeneric structural formula IA for the (R)-enantiomers of formula I:

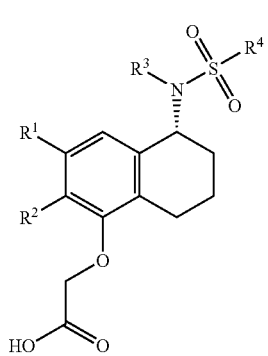

IA wherein $R^1$-$R^4$ are as defined previously.

In another embodiment, the compounds of formula I are (S)-enantiomers or pharmaceutically acceptable salts or esters thereof as depicted in the following subgeneric structural formula IB for the (S)-enantiomers of formula I:

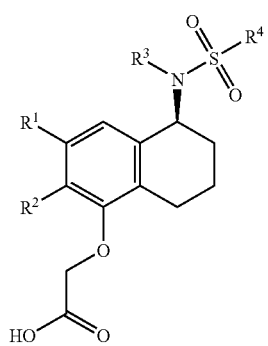

IB wherein $R^1$-$R^4$ are as defined previously.

In another embodiment the present invention is directed to a composition comprising a mixture (racemic or otherwise) of the (R)-enantiomers and (S)-enantiomers of a compound of formula I.

In a more particular embodiment the present invention is directed to the compounds of formula I or pharmaceutically acceptable salts or esters thereof, wherein $R^3$ is hydrogen.

In a more particular embodiment the present invention is directed to the compounds of formula IA or pharmaceutically acceptable salts or esters thereof, wherein $R^3$ is hydrogen.

In another embodiment the present invention is directed to the compounds of formula I or pharmaceutically acceptable salts or esters thereof, wherein $R^3$ is methyl.

In a more particular embodiment the present invention is directed to the compounds of formula IA or pharmaceutically acceptable salts or esters thereof, wherein $R^3$ is methyl.

In one embodiment the present invention is directed to the compounds of formula I or pharmaceutically acceptable salts or esters thereof, wherein $R^1$ is hydrogen, fluoro, chloro, bromo, methoxy, or phenyl and $R^2$ is hydrogen, fluoro, chloro, methyl, ethyl, propyl, or isopropyl; with the proviso that $R^1$ and $R^2$ are not both hydrogen.

In a more particular embodiment the present invention is directed to the compounds of formula IA or pharmaceutically acceptable salts or esters thereof, wherein $R^1$ is hydrogen, fluoro, chloro, bromo, methoxy, or phenyl and $R^2$ is hydrogen, fluoro, chloro, methyl, ethyl, propyl, or isopropyl; with the proviso that $R^1$ and $R^2$ are not both hydrogen.

In a more particular embodiment the present invention is directed to the compounds of formula IA or pharmaceutically acceptable salts or esters thereof, wherein $R^1$ is hydrogen, fluoro, chloro, bromo, methoxy, or phenyl and $R^2$ is hydrogen or fluoro; with the proviso that $R^1$ and $R^2$ are not both hydrogen.

In one embodiment the present invention is directed to the compounds of formula I or pharmaceutically acceptable salts or esters thereof, wherein at least one of $R^1$ or $R^2$ is halogen.

In another embodiment the present invention is directed to the compounds of formula I or pharmaceutically acceptable salts or esters thereof, wherein $R^1$ is fluoro or chloro.

In another embodiment the present invention is directed to the compounds of formula I or pharmaceutically acceptable salts or esters thereof, wherein $R^1$ is hydrogen and $R^2$ is fluoro.

In another embodiment the present invention is directed to the compounds of formula I or pharmaceutically acceptable salts or esters thereof, wherein $R^1$ is hydrogen and $R^2$ is chloro.

In another embodiment the present invention is directed to the compounds of formula I or pharmaceutically acceptable salts or esters thereof, wherein $R^1$ is hydrogen and $R^2$ is methyl.

In another embodiment the present invention is directed to the compounds of formula I or pharmaceutically acceptable salts or esters thereof, wherein $R^1$ is hydrogen and $R^2$ is ethyl.

In another embodiment the present invention is directed to the compounds of formula I or pharmaceutically acceptable salts or esters thereof, wherein $R^1$ is hydrogen and $R^2$ is propyl.

In another embodiment the present invention is directed to the compounds of formula I or pharmaceutically acceptable salts or esters thereof, wherein $R^1$ is hydrogen and $R^2$ is isopropyl.

In another embodiment the present invention is directed to the compounds of formula I or pharmaceutically acceptable salts or esters thereof, wherein $R^1$ is fluoro and $R^2$ is hydrogen.

In another embodiment the present invention is directed to the compounds of formula I or pharmaceutically acceptable salts or esters thereof, wherein $R^1$ is fluoro and $R^2$ is fluoro.

In another embodiment the present invention is directed to the compounds of formula I or pharmaceutically acceptable salts or esters thereof, wherein $R^1$ is fluoro and $R^2$ is chloro.

In another embodiment the present invention is directed to the compounds of formula I or pharmaceutically acceptable salts or esters thereof, wherein $R^1$ is fluoro and $R^2$ is methyl.

In another embodiment the present invention is directed to the compounds of formula I or pharmaceutically acceptable salts or esters thereof, wherein $R^1$ is fluoro and $R^2$ is ethyl.

In another embodiment the present invention is directed to the compounds of formula I or pharmaceutically acceptable salts or esters thereof, wherein $R^1$ is fluoro and $R^2$ is propyl.

In another embodiment the present invention is directed to the compounds of formula I or pharmaceutically acceptable salts or esters thereof, wherein $R^1$ is fluoro and $R^2$ is isopropyl.

In another embodiment the present invention is directed to the compounds of formula I or pharmaceutically acceptable salts or esters thereof, wherein $R^1$ is chloro and $R^2$ is hydrogen.

In another embodiment the present invention is directed to the compounds of formula I or pharmaceutically acceptable salts or esters thereof, wherein $R^1$ is chloro and $R^2$ is fluoro.

In another embodiment the present invention is directed to the compounds of formula I or pharmaceutically acceptable salts or esters thereof, wherein $R^1$ is chloro and $R^2$ is chloro.

In another embodiment the present invention is directed to the compounds of formula I or pharmaceutically acceptable salts or esters thereof, wherein $R^1$ is chloro and $R^2$ is methyl.

In another embodiment the present invention is directed to the compounds of formula I or pharmaceutically acceptable salts or esters thereof, wherein $R^1$ is chloro and $R^2$ is ethyl.

In another embodiment the present invention is directed to the compounds of formula I or pharmaceutically acceptable salts or esters thereof, wherein $R^1$ is chloro and $R^2$ is propyl.

In another embodiment the present invention is directed to the compounds of formula I or pharmaceutically acceptable salts or esters thereof, wherein $R^1$ is chloro and $R^2$ is isopropyl.

In another embodiment the present invention is directed to the compounds of formula I or pharmaceutically acceptable salts or esters thereof, wherein $R^1$ is bromo and $R^2$ is hydrogen.

In another embodiment the present invention is directed to the compounds of formula I or pharmaceutically acceptable salts or esters thereof, wherein $R^1$ is bromo and $R^2$ is fluoro.

In another embodiment the present invention is directed to the compounds of formula I or pharmaceutically acceptable salts or esters thereof, wherein $R^1$ is bromo and $R^2$ is chloro.

In another embodiment the present invention is directed to the compounds of formula I or pharmaceutically acceptable salts or esters thereof, wherein $R^1$ is bromo and $R^2$ is methyl.

In another embodiment the present invention is directed to the compounds of formula I or pharmaceutically acceptable salts or esters thereof, wherein $R^1$ is bromo and $R^2$ is ethyl.

In another embodiment the present invention is directed to the compounds of formula I or pharmaceutically acceptable salts or esters thereof, wherein $R^1$ is bromo and $R^2$ is propyl.

In another embodiment the present invention is directed to the compounds of formula I or pharmaceutically acceptable salts or esters thereof, wherein $R^1$ is bromo and $R^2$ is isopropyl.

In another embodiment the present invention is directed to the compounds of formula I or pharmaceutically acceptable salts or esters thereof, wherein $R^1$ is methoxy and $R^2$ is hydrogen.

In another embodiment the present invention is directed to the compounds of formula I or pharmaceutically acceptable salts or esters thereof, wherein $R^1$ is methoxy and $R^2$ is fluoro.

In another embodiment the present invention is directed to the compounds of formula I or pharmaceutically acceptable salts or esters thereof, wherein $R^1$ is methoxy and $R^2$ is chloro.

In another embodiment the present invention is directed to the compounds of formula I or pharmaceutically acceptable salts or esters thereof, wherein $R^1$ is methoxy and $R^2$ is methyl.

In another embodiment the present invention is directed to the compounds of formula I or pharmaceutically acceptable salts or esters thereof, wherein $R^1$ is methoxy and $R^2$ is ethyl.

In another embodiment the present invention is directed to the compounds of formula I or pharmaceutically acceptable salts or esters thereof, wherein $R^1$ is methoxy and $R^2$ is propyl.

In another embodiment the present invention is directed to the compounds of formula I or pharmaceutically acceptable salts or esters thereof, wherein $R^1$ is methoxy and $R^2$ is isopropyl.

In another embodiment the present invention is directed to the compounds of formula I or pharmaceutically acceptable salts or esters thereof, wherein $R^1$ is phenyl and $R^2$ is hydrogen.

In another embodiment the present invention is directed to the compounds of formula I or pharmaceutically acceptable salts or esters thereof, wherein $R^1$ is phenyl and $R^2$ is fluoro.

In another embodiment the present invention is directed to the compounds of formula I or pharmaceutically acceptable salts or esters thereof, wherein $R^1$ is phenyl and $R^2$ is chloro.

In another embodiment the present invention is directed to the compounds of formula I or pharmaceutically acceptable salts or esters thereof, wherein $R^1$ is phenyl and $R^2$ is methyl.

In another embodiment the present invention is directed to the compounds of formula I or pharmaceutically acceptable salts or esters thereof, wherein $R^1$ is phenyl and $R^2$ is ethyl.

In another embodiment the present invention is directed to the compounds of formula I or pharmaceutically acceptable salts or esters thereof, wherein $R^1$ is phenyl and $R^2$ is propyl.

In another embodiment the present invention is directed to the compounds of formula I or pharmaceutically acceptable salts or esters thereof, wherein $R^1$ is phenyl and $R^2$ is isopropyl.

In another particular embodiment the present invention is directed to the compounds of formula I or pharmaceutically acceptable salts or esters thereof, wherein $R^4$ is phenyl substituted by one or two substituents as defined previously.

In another embodiment the present invention is directed to the compounds of formula I or pharmaceutically acceptable salts or esters thereof, wherein $R^4$ is pyridine substituted by one or two substituents as defined previously.

In a more particular embodiment the present invention is directed to the compounds of formula I or pharmaceutically acceptable salts or esters thereof, wherein $R^4$ is phenyl substituted by one or two substituents independently selected from the group consisting of:
(1) halogen; and
(2) lower alkyl optionally substituted by halogen.

In a more specific embodiment the present invention is directed to the compounds of formula I or pharmaceutically acceptable salts or esters thereof, wherein $R^4$ is phenyl substituted by one or two substituents independently selected from the group consisting of:
(1) fluoro;
(2) chloro;
(3) bromo;
(4) lower alkyl
(5) lower alkanoyl;
(6) lower alkylsulfanyl, lower alkylsulfinyl, or lower alkylsulfonyl;
(7) lower cycloalkylsulfanyl, lower cycloalkylsulfinyl, or lower cycloalkylsulfonyl;
(8) trifluoromethyl, difluoromethyl, or fluoromethyl; and
(9) 1,1-difluoroethyl.
(10) phenyl optionally substituted by lower alkyl or lower alkylsulfonyl; and
(11) pyridine optionally substituted by lower alkyl or lower alkylsulfonyl.

In a more specific embodiment the present invention is directed to the compounds of formula I or pharmaceutically acceptable salts or esters thereof, wherein $R^4$ is phenyl substituted by one or two substituents independently selected from the group consisting of:
(1) fluoro;
(2) chloro;
(3) bromo;
(4) methyl;
(5) ethyl;
(6) propyl or isopropyl;
(7) butyl, sec-butyl, or tert-butyl;
(8) trifluoromethyl, difluoromethyl, or fluoromethyl; and
(9) 1,1-difluoroethyl.

In a more specific embodiment the present invention is directed to the compounds of formula I or pharmaceutically acceptable salts or esters thereof, wherein $R^4$ is phenyl substituted by one or two substituents independently selected from the group consisting of:
(1) fluoro;
(2) chloro;
(3) bromo; and
(4) trifluoromethyl.

In one embodiment the present invention is directed to the compounds of formula I or pharmaceutically acceptable salts or esters thereof, wherein $R^4$ is pyridine substituted by one or two substituents independently selected from the group consisting of:
(1) halogen;
(2) lower alkyl optionally substituted by halogen; and
(3) phenyl or pyridine, wherein said phenyl or pyridine is optionally substituted by lower alkyl.

In a more specific embodiment the present invention is directed to the compounds of formula I or pharmaceutically acceptable salts or esters thereof, wherein $R^4$ is pyridine substituted by one or two substituents independently selected from the group consisting of:
(1) fluoro;
(2) chloro;
(3) bromo;
(4) lower alkyl
(5) lower alkanoyl;
(6) lower alkylsulfanyl, lower alkylsulfinyl, or lower alkylsulfonyl;
(7) lower cycloalkylsulfanyl, lower cycloalkylsulfinyl, or lower cycloalkylsulfonyl;
(8) trifluoromethyl, difluoromethyl, or fluoromethyl; and
(9) 1,1-difluoroethyl.
(10) phenyl optionally substituted by lower alkyl or lower alkylsulfonyl; and
(11) pyridine optionally substituted by lower alkyl or lower alkylsulfonyl.

In a more specific embodiment the present invention is directed to the compounds of formula I or pharmaceutically acceptable salts or esters thereof, wherein $R^4$ is pyridine substituted by one or two substituents independently selected from the group consisting of:
(1) fluoro;
(2) chloro;
(3) bromo;
(4) methyl;
(5) ethyl;
(6) propyl or isopropyl;
(7) butyl, sec-butyl, or tert-butyl;
(8) trifluoromethyl, difluoromethyl, or fluoromethyl;
(9) 1,1-difluoroethyl;
(10) phenyl optionally substituted by lower alkyl; and
(11) pyridine optionally substituted by lower alkyl.

In a more specific embodiment the present invention is directed to the compounds of formula I or pharmaceutically acceptable salts or esters thereof, wherein $R^4$ is pyridine substituted by one substituent independently selected from the group consisting of:
(1) phenyl optionally substituted by lower alkyl; and
(2) pyridine optionally substituted by lower alkyl.

In a more specific embodiment the present invention is directed to the compounds of formula I or pharmaceutically acceptable salts or esters thereof, wherein R⁴ is pyridine substituted by phenyl wherein said phenyl is substituted by a lower alkyl moiety. In a more particular embodiment said phenyl is substituted by an isopropyl moiety.

In particular embodiments, the present invention is directed to the compounds of formula I or pharmaceutically acceptable salts or esters thereof, wherein R⁴ is phenyl substituted by one or two substituents at positions 2, 3, 4, 5, or 6 where such positions are as indicated below in formula IC:

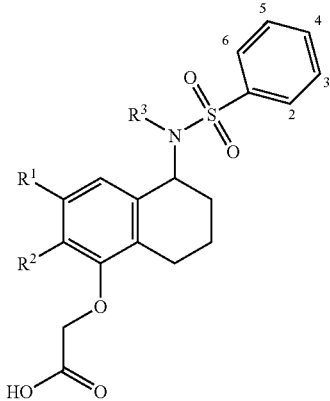

IC

In one embodiment, the present invention is directed to the compounds of formula I or pharmaceutically acceptable salts or esters thereof, wherein R⁴ is phenyl substituted by one substituent at the 2 position and another substituent at the 4 or 5 position (as indicated in formula IC).

In another embodiment, the present invention is directed to the compounds of formula I or pharmaceutically acceptable salts or esters thereof, wherein R⁴ is phenyl substituted by one substituent at the 2 position and another substituent at the 5 position (as indicated in formula IC).

In another embodiment, the present invention is directed to the compounds of formula I or pharmaceutically acceptable salts or esters thereof, wherein R⁴ is phenyl substituted by one substituent at the 2 or 6 position and another substituent at the 4 position (as indicated in formula IC).

In another embodiment, the present invention is directed to the compounds of formula I or pharmaceutically acceptable salts or esters thereof, wherein R⁴ is phenyl substituted by one substituent at the 3 position and another substituent at the 5 position (as indicated in formula IC).

In another embodiment, the present invention is directed to the compounds of formula I or pharmaceutically acceptable salts or esters thereof, wherein R⁴ is phenyl substituted by one substituent at the 3 or 5 position and another substituent at the 4 position (as indicated in formula IC).

In another embodiment, the present invention is directed to the compounds of formula I or pharmaceutically acceptable salts or esters thereof, wherein R¹ is fluoro or chloro; R² is hydrogen or fluoro; and R⁴ is phenyl substituted at positions 3 and 5 (as indicated in formula IC) with substituents independently selected from the group consisting of fluoro, bromo, or trifluoromethyl.

In another embodiment, the present invention is directed to the compounds of formula I or pharmaceutically acceptable salts or esters thereof, wherein R¹ is fluoro or chloro; R² is hydrogen or fluoro; and R⁴ is phenyl substituted at positions 3 and 5 (as indicated in formula IC) with trifluoromethyl.

In other particular embodiments, the present invention is directed to the compounds of formula I or pharmaceutically acceptable salts or esters thereof, wherein R⁴ is pyridine substituted by one or two substituents at positions, 4, 5, or 6 where such positions are as indicated below in formula ID:

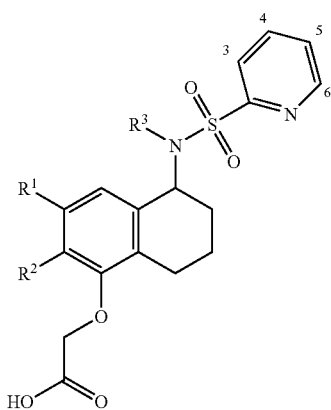

ID

In one embodiment, the present invention is directed to the compounds of formula I or pharmaceutically acceptable salts or esters thereof, wherein R⁴ is pyridine substituted by one substituent at the 6 position and another substituent at the 4 position (as indicated in formula ID).

In another embodiment, the present invention is directed to the compounds of formula I or pharmaceutically acceptable salts or esters thereof, wherein R⁴ is pyridine substituted by one substituent at the 4 position and another substituent at the 5 position (as indicated in formula ID).

In another embodiment, the present invention is directed to the compounds of formula I or pharmaceutically acceptable salts or esters thereof, wherein R⁴ is pyridine substituted by one substituent at the 5 position (as indicated in formula ID).

In another embodiment, the present invention is directed to the compounds of formula I or pharmaceutically acceptable salts or esters thereof, wherein R⁴ is pyridine substituted by one substituent at the 5 position and another substituent at the 6 position (as indicated in formula ID).

In another embodiment, the present invention is directed to the compounds of formula I or pharmaceutically acceptable salts or esters thereof, wherein R⁴ is pyridine substituted by one substituent at the 6 position (as indicated in formula ID).

In another embodiment, the present invention is directed to the compounds of formula I or pharmaceutically acceptable salts or esters thereof, wherein R⁴ is pyridine substituted by phenyl at the 6 position (as indicated in formula ID) wherein said phenyl is itself optionally substituted by lower alkyl.

In a more specific embodiment, the present invention is directed to a compound of formula I selected from the group consisting of:

[(R)-5-(3,5-Bis-trifluoromethyl-benzenesulfonylamino)-2,3-dichloro-5,6,7,8-tetrahydro-naphthalen-1-yloxy]-acetic acid;

[5-(3,5-Bis-trifluoromethyl-benzenesulfonylamino)-2-isopropyl-5,6,7,8-tetrahydro-naphthalen-1-yloxy]-acetic acid;

[5-(3,5-Bis-trifluoromethyl-benzenesulfonylamino)-2-methyl-5,6,7,8-tetrahydro-naphthalen-1-yloxy]-acetic acid;

[5-(3,5-Bis-trifluoromethyl-benzenesulfonylamino)-2-ethyl-5,6,7,8-tetrahydro-naphthalen-1-yloxy]-acetic acid;
[5-(3,5-Bis-trifluoromethyl-benzenesulfonylamino)-3-chloro-2-methyl-5,6,7,8-tetrahydro-naphthalen-1-yloxy]-acetic acid;
[5-(3,5-Bis-trifluoromethyl-benzenesulfonylamino)-3-chloro-5,6,7,8-tetrahydro-naphthalen-1-yloxy]-acetic acid;
[5-(3,5-Bis-trifluoromethyl-benzenesulfonylamino)-2-chloro-5,6,7,8-tetrahydro-naphthalen-1-yloxy]-acetic acid;
[(R)-5-(3,5-Bis-trifluoromethyl-benzenesulfonylamino)-3-chloro-5,6,7,8-tetrahydro-naphthalen-1-yloxy]-acetic acid;
5-(3,5-Bis-trifluoromethyl-benzenesulfonylamino)-3-chloro-2-fluoro-5,6,7,8-tetrahydro-naphthalen-1-yloxy]-acetic acid;
[3-Chloro-5-(2,5-dichloro-benzenesulfonylamino)-2-fluoro-5,6,7,8-tetrahydro-naphthalen-1-yloxy]-acetic acid;
[3-Chloro-5-(2,4-dichloro-benzenesulfonylamino)-5,6,7,8-tetrahydro-naphthalen-1-yloxy]-acetic acid;
5-(3,5-Bis-trifluoromethyl-benzenesulfonylamino)-2,3-dichloro-5,6,7,8-tetrahydro-naphthalen-1-yloxy]-acetic acid;
[3-Chloro-5-(2,5-dichloro-benzenesulfonylamino)-5,6,7,8-tetrahydro-naphthalen-1-yloxy]-acetic acid;
[3-Chloro-5-(2,4-dichloro-benzenesulfonylamino)-2-fluoro-5,6,7,8-tetrahydro-naphthalen-1-yloxy]-acetic acid;
[5-(3-Bromo-5-trifluoromethyl-benzenesulfonylamino)-3-chloro-2-fluoro-5,6,7,8-tetrahydro-naphthalen-1-yloxy]-acetic acid;
[3-Chloro-5-(3-fluoro-5-trifluoromethyl-benzenesulfonylamino)-5,6,7,8-Tetrahydro-naphthalen-1-yloxy]-acetic acid;
[5-(3-Bromo-5-trifluoromethyl-benzenesulfonylamino)-3-chloro-5,6,7,8-tetrahydro-naphthalen-1-yloxy]-acetic acid;
[(R)-3-Chloro-5-(2,4-dichloro-benzenesulfonylamino)-5,6,7,8-tetrahydro-naphthalen-1-yloxy]-acetic acid;
[5-(3,5-Bis-trifluoromethyl-benzenesulfonylamino)-3-bromo-5,6,7,8-tetrahydro-naphthalen-1-yloxy]-acetic acid;
[(R)-5-(3,5-Bis-trifluoromethyl-benzenesulfonylamino)-3-bromo-5,6,7,8-tetrahydro-naphthalen-1-yloxy]-acetic acid;
[3-Chloro-2-fluoro-5-(3-fluoro-5-trifluoromethyl-benzenesulfonylamino)-5,6,7,8-tetrahydro-naphthalen-1-yloxy]-acetic acid;
[5-(3,5-Bis-trifluoromethyl-benzenesulfonylamino)-2-fluoro-5,6,7,8-tetrahydro-naphthalen-1-yloxy]-acetic acid;
[(R)-5-(3,5-Bis-trifluoromethyl-benzenesulfonylamino)-3-methoxy-5,6,7,8-tetrahydro-naphthalen-1-yloxy]-acetic acid;
[5-(3,5-Bis-trifluoromethyl-benzenesulfonylamino)-3-phenyl-5,6,7,8-tetrahydro-naphthalen-1-yloxy]-acetic acid;
[(R)-5-(3,5-Bis-trifluoromethyl-benzenesulfonylamino)-2-chloro-5,6,7,8-tetrahydro-naphthalen-1-yloxy]-acetic acid;
[2,3-Difluoro-5-(3-fluoro-5-trifluoromethyl-benzenesulfonylamino)-5,6,7,8-tetrahydro-naphthalen-1-yloxy]-acetic acid;
[3-Fluoro-5-(3-fluoro-5-trifluoromethyl-benzenesulfonylamino)-5,6,7,8-tetrahydro-naphthalen-1-yloxy]-acetic acid;
[5-(3-Bromo-5-trifluoromethyl-benzenesulfonylamino)-3-fluoro-5,6,7,8-tetrahydro-naphthalen-1-yloxy]-acetic acid;
5-(3-Bromo-5-trifluoromethyl-benzenesulfonylamino)-2,3-difluoro-5,6,7,8-tetrahydro-naphthalen-1-yloxy]-acetic acid;
[5-(2,4-Dichloro-benzenesulfonylamino)-2,3-difluoro-5,6,7,8-tetrahydro-naphthalen-1-yloxy]-acetic acid;
[5-(2,4-Dichloro-benzenesulfonylamino)-3-fluoro-5,6,7,8-tetrahydro-naphthalen-1-yloxy]-acetic acid;
[5-(2,5-Dichloro-benzenesulfonylamino)-2,3-difluoro-5,6,7,8-tetrahydro-naphthalen-1-yloxy]-acetic acid;
[5-(2,5-Dichloro-benzenesulfonylamino)-3-fluoro-5,6,7,8-tetrahydro-naphthalen-1-yloxy]-acetic acid;
{2,3-Difluoro-5-[5-(3-isopropyl-phenyl)-pyridine-2-sulfonylamino]-5,6,7,8-tetrahydro-naphthalen-1-yloxy}-acetic acid;
{3-Fluoro-5-[5-(3-isopropyl-phenyl)-pyridine-2-sulfonylamino]-5,6,7,8-tetrahydro-naphthalen-1-yloxy}-acetic acid;
{3-Chloro-5-[5-(3-isopropyl-phenyl)-pyridine-2-sulfonylamino]-5,6,7,8-tetrahydro-naphthalen-1-yloxy}-acetic acid;
[(R)-3-Bromo-5-(3-bromo-5-trifluoromethyl-benzenesulfonylamino)-5,6,7,8-tetrahydro-naphthalen-1-yloxy]-acetic acid;
[(R)-3-Chloro-2-fluoro-5-(3-fluoro-5-trifluoromethyl-benzenesulfonylamino)-5,6,7,8-tetrahydro-naphthalen-1-yloxy]-acetic acid;
[(R)-5-(3-Bromo-5-trifluoromethyl-benzenesulfonylamino)-3-chloro-2-fluoro-5,6,7,8-tetrahydro-naphthalen-1-yloxy]-acetic acid;
[(R)-3-Chloro-5-(2,4-dichloro-benzenesulfonylamino)-2-fluoro-5,6,7,8-tetrahydro-naphthalen-1-yloxy]-acetic acid;
[(R)-3-Chloro-5-(3-fluoro-5-trifluoromethyl-benzenesulfonylamino)-5,6,7,8-tetrahydro-naphthalen-1-yloxy]-acetic acid;
[(R)-5-(3-Bromo-5-trifluoromethyl-benzenesulfonylamino)-3-chloro-5,6,7,8-tetrahydro-naphthalen-1-yloxy]-acetic acid;
[(R)-3-Chloro-5-(2,5-dichloro-benzenesulfonylamino)-5,6,7,8-tetrahydro-naphthalen-1-yloxy]-acetic acid;
{3-Chloro-2-fluoro-5-[5-(3-isopropyl-phenyl)-pyridine-2-sulfonylamino]-5,6,7,8-tetrahydro-naphthalen-1-yloxy}-acetic acid;
[5-(2,5-Dichloro-benzenesulfonylamino)-2-fluoro-5,6,7,8-tetrahydro-naphthalen-1-yloxy]-acetic acid;
[5-(2,4-Dichloro-benzenesulfonylamino)-2-fluoro-5,6,7,8-tetrahydro-naphthalen-1-yloxy]-acetic acid;
{2-Fluoro-5-[5-(3-isopropyl-phenyl)-pyridine-2-sulfonylamino]-5,6,7,8-tetrahydro-naphthalen-1-yloxy}-acetic acid;
[(R)-3-Bromo-5-(2,5-dichloro-benzenesulfonylamino)-5,6,7,8-tetrahydro-naphthalen-1-yloxy]-acetic acid;
[(R)-3-Bromo-5-(2,4-dichloro-benzenesulfonylamino)-5,6,7,8-tetrahydro-naphthalen-1-yloxy]-acetic acid;
[5-(3,5-Bis-methanesulfonyl-benzenesulfonylamino)-3-bromo-5,6,7,8-tetrahydro-naphthalen-1-yloxy]-acetic acid; and any pharmaceutically acceptable salt or ester thereof.

In another specific embodiment, the present invention is directed to a compound of formula I selected from the group consisting of:

[5-(3,5-Bis-trifluoromethyl-benzenesulfonyl)-methyl-amino)-3-chloro-2-fluoro-5,6,7,8-tetrahydro-naphthalen-1-yloxy]-acetic acid;

{5-[(3,5-Bis-trifluoromethyl-benzenesulfonyl)-methyl-amino]-2-methyl-5,6,7,8-tetrahydro-naphthalen-1-yloxy}-acetic acid;

{5-[(3,5-Bis-trifluoromethyl-benzenesulfonyl)-methyl-amino]-2-ethyl-5,6,7,8-tetrahydro-naphthalen-1-yloxy}-acetic acid;

{5-[(3,5-Bis-trifluoromethyl-benzenesulfonyl)-methyl-amino]-3-chloro-5,6,7,8-tetrahydro-naphthalen-1-yloxy}-acetic acid;

{(R)-5-[(3,5-Bis-trifluoromethyl-benzenesulfonyl)-methyl-amino]-3-chloro-5,6,7,8-tetrahydro-naphthalen-1-yloxy}-acetic acid;

{3-Chloro-5-[(2,4-dichloro-benzenesulfonyl)-methyl-amino]-5,6,7,8-tetrahydro-naphthalen-1-yloxy}-acetic acid;

{5-[(3,5-Bis-trifluoromethyl-benzenesulfonyl)-methyl-amino]-2,3-dichloro-5,6,7,8-tetrahydro-naphthalen-1-yloxy}-acetic acid;

{5-[(3,5-Bis-trifluoromethyl-benzenesulfonyl)-methyl-amino]-3-chloro-2-methyl-5,6,7,8-tetrahydro-naphthalen-1-yloxy}-acetic acid;

{3-Chloro-5-[(2,5-dichloro-benzenesulfonyl)-methyl-amino]-2-fluoro-5,6,7,8-tetrahydro-naphthalen-1-yloxy}-acetic acid;

{3-Chloro-5-[(2,5-dichloro-benzenesulfonyl)-methyl-amino]-5,6,7,8-tetrahydro-naphthalen-1-yloxy}-acetic acid;

{3-Chloro-5-[(2,4-dichloro-benzenesulfonyl)-methyl-amino]-2-fluoro-5,6,7,8-tetrahydro-naphthalen-1-yloxy}-acetic acid;

{5-[(3-Bromo-5-trifluoromethyl-benzenesulfonyl)-methyl-amino]-3-chloro-2-fluoro-5,6,7,8-tetrahydro-naphthalen-1-yloxy}-acetic acid;

{5-[(3-Bromo-5-trifluoromethyl-benzenesulfonyl)-methyl-amino]-3-chloro-5,6,7,8-tetrahydro-naphthalen-1-yloxy}-acetic acid;

{3-Chloro-5-[(3-fluoro-5-trifluoromethyl-benzenesulfonyl)-methyl-amino]-5,6,7,8-tetrahydro-naphthalen-1-yloxy}-acetic acid;

{3-Chloro-2-fluoro-5-[(3-fluoro-5-trifluoromethyl-benzenesulfonyl)-methyl-amino]-5,6,7,8-tetrahydro-naphthalen-1-yloxy}-acetic acid;

{5-[(2,4-Dichloro-benzenesulfonyl)-methyl-amino]-3-fluoro-5,6,7,8-tetrahydro-naphthalen-1-yloxy}-acetic acid;

{5-[(3,5-Bis-trifluoromethyl-benzenesulfonyl)-methyl-amino]-2-fluoro-5,6,7,8-tetrahydro-naphthalen-1-yloxy}-acetic acid;

{5-[(2,4-Dichloro-benzenesulfonyl)-methyl-amino]-2,3-difluoro-5,6,7,8-tetrahydro-naphthalen-1-yloxy}-acetic acid;

{5-[(2,5-Dichloro-benzenesulfonyl)-methyl-amino]-3-fluoro-5,6,7,8-tetrahydro-naphthalen-1-yloxy}-acetic acid;

{5-[(3-Bromo-5-trifluoromethyl-benzenesulfonyl)-methyl-amino]-2,3-difluoro-5,6,7,8-tetrahydro-naphthalen-1-yloxy}-acetic acid;

{5-[(2,5-Dichloro-benzenesulfonyl)-methyl-amino]-2,3-difluoro-5,6,7,8-tetrahydro-naphthalen-1-yloxy}-acetic acid;

{5-[(3-Bromo-5-trifluoromethyl-benzenesulfonyl)-methyl-amino]-3-fluoro-5,6,7,8-tetrahydro-naphthalen-1-yloxy}-acetic acid;

{3-Fluoro-5-[(3-fluoro-5-trifluoromethyl-benzenesulfonyl)-methyl-amino]-5,6,7,8-tetrahydro-naphthalen-1-yloxy}-acetic acid;

{2,3-Difluoro-5-[(3-fluoro-5-trifluoromethyl-benzenesulfonyl)-methyl-amino]-5,6,7,8-tetrahydro-naphthalen-1-yloxy}-acetic acid;

(2,3-Difluoro-5-{[5-(3-isopropyl-phenyl)-pyridine-2-sulfonyl]-methyl-amino}-5,6,7,8-tetrahydro-naphthalen-1-yloxy)-acetic acid;

(3-Fluoro-5-{[5-(3-isopropyl-phenyl)-pyridine-2-sulfonyl]-methyl-amino}-5,6,7,8-tetrahydro-naphthalen-1-yloxy)-acetic acid;

(3-Chloro-5-{[5-(3-isopropyl-phenyl)-pyridine-2-sulfonyl]-methyl-amino}-5,6,7,8-tetrahydro-naphthalen-1-yloxy)-acetic acid;

(3-Chloro-2-fluoro-5-{[5-(3-isopropyl-phenyl)-pyridine-2-sulfonyl]-methyl-amino}-5,6,7,8-tetrahydro-naphthalen-1-yloxy)-acetic acid;

{5-[(2,5-Dichloro-benzenesulfonyl)-methyl-amino]-2-fluoro-5,6,7,8-tetrahydro-naphthalen-1-yloxy}-acetic acid;

{5-[(2,4-Dichloro-benzenesulfonyl)-methyl-amino]-2-fluoro-5,6,7,8-tetrahydro-naphthalen-1-yloxy}-acetic acid;

(2-Fluoro-5-{[5-(3-isopropyl-phenyl)-pyridine-2-sulfonyl]-methyl-amino}-5,6,7,8-tetrahydro-naphthalen-1-yloxy)-acetic acid; and any pharmaceutically acceptable salt or ester thereof.

In another particular embodiment, the present invention is directed to the compounds of formula I or pharmaceutically acceptable salts or esters thereof except for [5-(3,5-Bis-trifluoromethyl-benzenesulfonylamino)-2-isopropyl-5,6,7,8-tetrahydro-naphthalen-1-yloxy]-acetic acid; and any pharmaceutically acceptable salt or ester thereof.

In another particular embodiment, the present invention is directed to the compounds of formula I or pharmaceutically acceptable salts or esters thereof except for {5-[(3,5-Bis-trifluoromethyl-benzenesulfonyl)-methyl-amino]-2-methyl-5,6,7,8-tetrahydro-naphthalen-1-yloxy}-acetic acid; and any pharmaceutically acceptable salt or ester thereof.

In another particular embodiment, the present invention is directed to the compounds of formula I or pharmaceutically acceptable salts or esters thereof except for {5-[(3,5-Bis-trifluoromethyl-benzenesulfonyl)-methyl-amino]-2-ethyl-5,6,7,8-tetrahydro-naphthalen-1-yloxy}-acetic acid; and any pharmaceutically acceptable salt or ester thereof.

In another particular embodiment, the present invention is directed to the compounds of formula I or pharmaceutically acceptable salts or esters thereof except for {5-[(3,5-Bis-trifluoromethyl-benzenesulfonyl)-methyl-amino]-2,3-dichloro-5,6,7,8-tetrahydro-naphthalen-1-yloxy}-acetic acid; and any pharmaceutically acceptable salt or ester thereof.

In another particular embodiment, the present invention is directed to the compounds of formula I or pharmaceutically acceptable salts or esters thereof except for {5-[(3,5-Bis-trifluoromethyl-benzenesulfonyl)-methyl-amino]-3-chloro-2-methyl-5,6,7,8-tetrahydro-naphthalen-1-yloxy}-acetic acid; and any pharmaceutically acceptable salt or ester thereof.

In another particular embodiment, the present invention is directed to the compounds of formula I or pharmaceutically acceptable salts or esters thereof except for {3-Chloro-5-[(2,5-dichloro-benzenesulfonyl)-methyl-amino]-2-fluoro-5,6,7, 8-tetrahydro-naphthalen-1-yloxy}-acetic acid; and any pharmaceutically acceptable salt or ester thereof.

In another particular embodiment, the present invention is directed to the compounds of formula I or pharmaceutically acceptable salts or esters thereof except for {3-Chloro-5-[(2,4-dichloro-benzenesulfonyl)-methyl-amino]-2-fluoro-5,6,7,8-tetrahydro-naphthalen-1-yloxy}-acetic acid; and any pharmaceutically acceptable salt or ester thereof.

In another particular embodiment, the present invention is directed to the compounds of formula I or pharmaceutically acceptable salts or esters thereof except for {5-[(2,4-dichloro-benzenesulfonyl)-methyl-amino]-3-fluoro-5,6,7,8-tetrahydro-naphthalen-1-yloxy}-acetic acid; and any pharmaceutically acceptable salt or ester thereof.

General Synthesis of Compounds according to the Invention

The compounds of the present invention can be prepared by any conventional means. Suitable processes for synthesizing these compounds are provided in the examples. Generally, compounds of formula I can be prepared according to the schemes illustrated below.

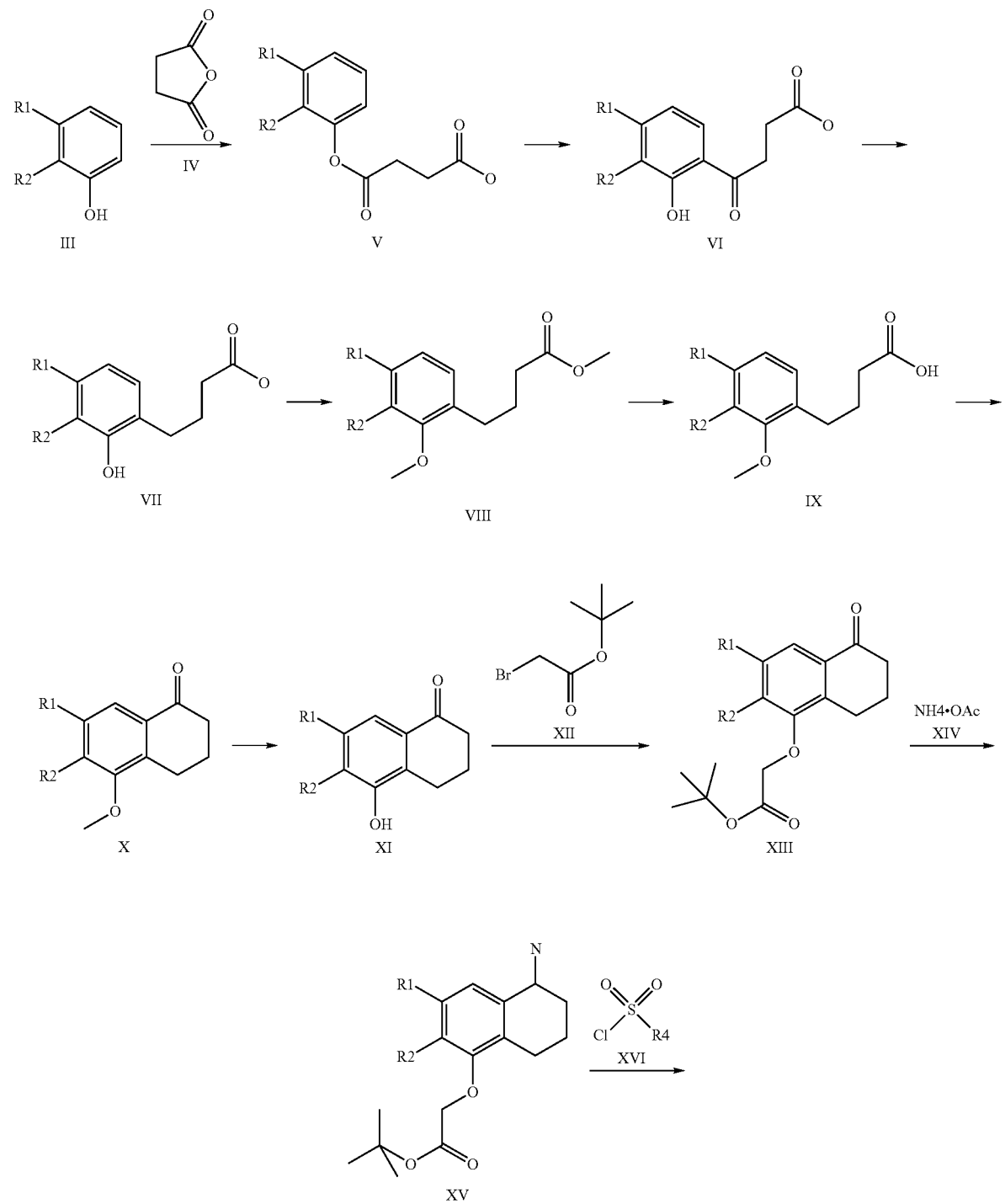

Scheme 1

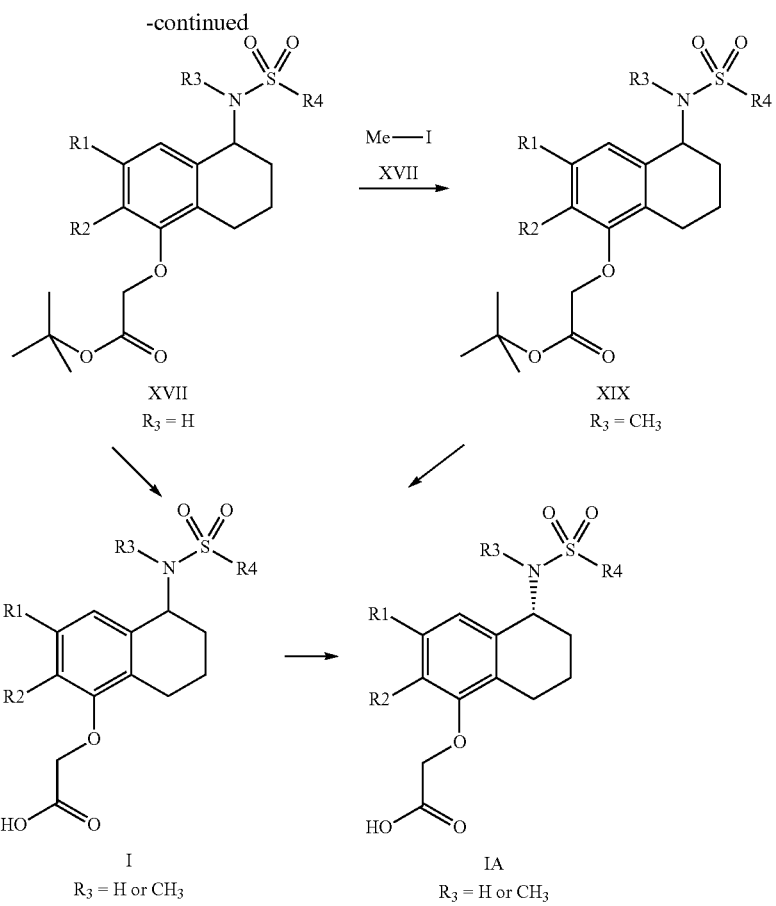

Compounds of interest I and IA with substituents on the tetrahydro-naphthalene ring can be prepared according to Scheme 1. Starting with phenols III and succinic anhydride (IV), esterification followed by Fries rearrangement gives the butyric acid derivatives VI. Clemmensen reduction of keto acids VI yields compounds of structures VII. Methylation followed by ester hydrolysis converts phenols VII to the methoxy acid derivatives IX, which can form naphthalenones X via intramolecular Friedel-Crafts reactions. Demethylation of compounds of structure X gives 5-hydroxy-naphthalenones XI, which undergo nucleophilic substitution with tert-butyl bromoacetate (XII) under basic conditions to generate the ethers XIII. Reductive amination reactions of intermediates XIII afford the corresponding amino derivatives XV. Sulfonylation of amino compounds XV with sulfonyl chlorides XVI affords the corresponding sulfonamides of structure XVII. N-Methylation of the sulfonamides XVII gives the corresponding derivatives XIX. Ester hydrolysis of either XVII or XIX produces compounds of interest I, which can be resolved to the optically pure (R)-enantiomers IA by chiral HPLC.

In the first step of the sequence, nucleophilic substitution reactions of phenols III and succinic anhydride (IV) give the phenol esters V. Subsequent Fries rearrangement of intermediates V to yield the ortho keto acids VI can be carried out in the presence of a strong Lewis acid catalyst such as aluminum chloride, boron trifluoride, or titanium tetrachloride under anhydrous conditions, either neat, or in a solvent such as tetrahydrofuran, dichloromethane, 1,1,2,2-tetrachloroethane, or dichloroethane, at a temperature between room temperature and reflux temperature for several hours.

Conversion of keto acids VI to derivatives VII can be accomplished under Clemmensen reduction conditions. The reaction is typically carried out using zinc amalgam and hydrochloric acid with or without an auxiliary solvent such as toluene or ether, at a temperature between room temperature and reflux temperature for 3 days.

Methylation of phenols VII to compounds VIII can be achieved using methods that are well known to someone skilled in the art. For example, dimethyl sulfate can be used in presence of a base such as potassium carbonate or potassium hydroxide in a solvent such as acetone, acetonitrile, 1,4-dioxane, toluene, water or mixtures thereof, at a temperature between room temperature and reflux temperature, preferably reflux temperature, for several hours. Alternatively, methyl iodide can be used as a methylating agent under similar reaction conditions.

For the specific case of compound VIII where R1 is bromo and R2 is hydrogen, the key intermediate VIII can be prepared as described in U.S. Pat. No. 7,226,951 (WO 2005058798) which is hereby incorporated by reference in its entirety.

Hydrolysis of methyl ester VIII to give the corresponding acid derivatives IX can be carried out in the presence of an aqueous inorganic base such as sodium hydroxide or potassium hydroxide, in an inert solvent such as 1,4-dioxane or tetrahydrofuran, at room temperature for several hours.

The cyclization of acid derivatives IX to form naphthalenones X can be accomplished in two steps. The first step is to convert the acids IX to the corresponding acyl chloride derivatives using methods that are well known to someone skilled in the art. The acids can be treated with thionyl chloride or certain phosphorus chloride reagents such as phosphorus trichloride or phosphorus pentachloride at a temperature between room temperature and reflux temperature for several hours. The second step consists of intramolecular Friedel-Crafts acylation of the resulting acyl chloride intermediates in the presence of a strong Lewis acid such as aluminum chloride, under anhydrous conditions. The reactions can be carried out either neat (no solvent), or in a solvent such as tetrahydrofuran, dichloromethane, 1,1,2,2-tetrachloroethane, benzene or 1,2-dichloroethane, at a temperature between room temperature and 80 degrees for several hours. Alternatively, naphthalenones X can be obtained by treating compounds IX with phosphorus oxychloride at an elevated temperature in a solvent such as 1,2-dichloroethane, tetrahydrofuran, or 1,1,2,2-tetrachloroethane for several hours.

Demethylation of the methoxy compounds X to give the phenol derivatives XI can be carried out in the presence of aluminum chloride in a solvent such as dichloromethane, acetonitrile, toluene, or p-xylene at a temperature between room temperature and reflux temperature for several hours.

Nucleophilic substitution reactions of 8-hydroxy-naphthalenones X with tert-butyl bromoacetate (XII) to give compounds XIII can be accomplished using methods that are well known to someone skilled in the art. The reactions are typically carried out in the presence of a carbonate base (e.g. cesium carbonate, potassium carbonate, or the like) or potassium hydroxide in an aprotic solvent such as acetonitrile, N,N-dimethylformamide, or dimethyl sulfoxide, at a temperature between 50 and 100° C. for several hours.

Transformation of the naphthalenones XIII to the amine derivatives XV can be achieved via reductive amination. The reactions can be carried out in stepwise fashion by treating ketones XIII with an amine such as ammonium acetate (XIV) or ammonia to generate the corresponding imines, which can then be isolated and reduced with a suitable reducing agent (e.g. sodium borohydride). It is also possible to carry out the same reaction sequence in one pot, with the imine formation and reduction occurring concurrently with reducing agents such as sodium cyanoborohydride ($NaBH_3CN$) or sodium triacetoxyborohydride ($NaBH(OCOCH_3)_3$). The reaction is typically performed in a solvent such as methanol or tetrahydrofuran, at a temperature between room temperature and reflux temperature for several hours.

Sulfonylation of the amines XV with sulfonyl chlorides XVI to give sulfonamides XVII can be easily accomplished using methods well known to someone skilled in the art. The reaction is typically carried out in the presence of a base such as diisopropylethylamine, triethylamine, pyridine, or dimethyl-pyridin-4-yl-amine in a suitable inert solvent such as dichloromethane, acetonitrile, 1,4-dioxane, tetrahydrofuran or mixtures thereof, at 0° C. to room temperature for 16 hours.

A large number of sulfonyl chlorides are commercially available. The preparation of non-commercial sulfonyl chlorides is well known to someone skilled in the art, through a variety of methods [for examples, see a) Gilbert, E. E. *Sulfonation and Related Reactions*; Wiley: NY, 1965; b) Gilbert, E. E. *Synthesis,* 1969, 1, 6; and c) the procedure described for the preparation of 5-(3-isopropyl-phenyl)-pyridine-2-sulfonyl chloride from 2-chloro-5-(3-isopropyl-phenyl)-pyridine, below].

N-Methylation of compounds XVII to produce the derivatives XIX can be achieved by treating compounds XVII with methyl iodide (XVIII) in the presence of a weak base such as potassium carbonate or sodium carbonate, in an inert solvent such as N,N-dimethylformamide, acetonitrile, or tetrahydrofuran, at 65 degrees for 5 hours.

Hydrolysis of esters XVII or XIX gives the corresponding acids I. The reaction can be carried out in the presence of an aqueous inorganic base such as lithium hydroxide, sodium hydroxide, or potassium hydroxide, in an inert solvent such as 1,4-dioxane or tetrahydrofuran, at room temperature for several hours.

The compounds of interest IA, in enantiomerically pure (R)-form, can be obtained through a resolution of the racemic mixtures I using chiral chromatography.

Alternatively, the (R)-enantiomers IA can be generated by following the exact same route as described in Scheme 1, this time employing the enantiomerically pure form of intermediates XV, which can be obtained by chiral resolution of racemic XV.

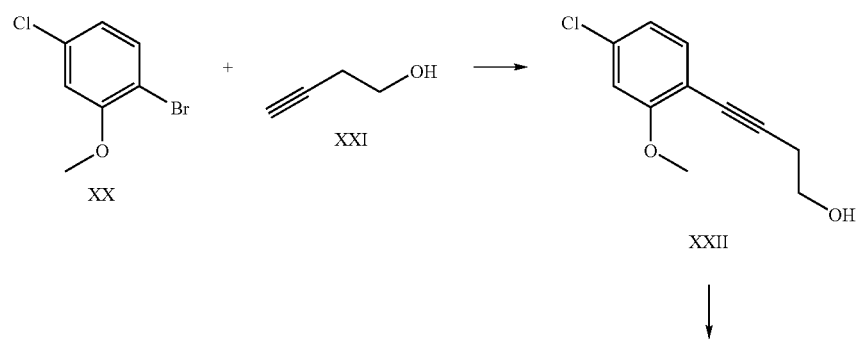

Scheme 2

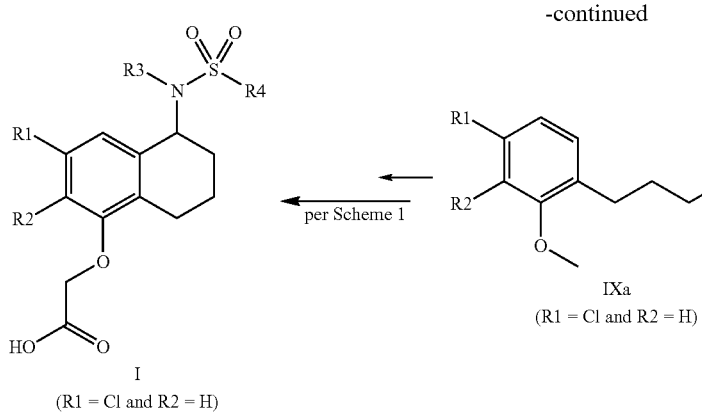
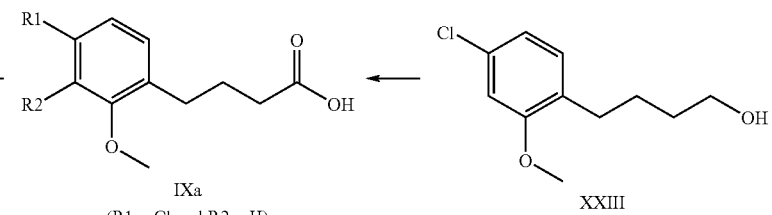

For the specific case where R1 is chloro and R2 is hydrogen, an alternative synthesis may be utilized to access the key intermediate IXa (prior to intramolecular Friedel-Crafts cyclization), as outlined in Scheme 2. A Sonogashira coupling between 2-bromo-5-chloroanisole (XX), and 3-butyn-1-ol (XXI) provides the acetylene intermediate XXII, which can be reduced by hydrogenation to furnish the intermediate alcohol XXIII. Oxidation of the alcohol XXIII to the corresponding carboxylic acid provides the key intermediate IXa (wherein R1 is chloro and R2 is hydrogen). The intermediate IXa can then be converted to compounds of interest I wherein R1 is chloro and R2 is hydrogen, as previously described above (in Scheme 1).

The Sonogashira coupling reaction between 2-bromo-5-chloroanisole (XX) and 3-butyn-1-ol (XXI) to give the aryl-substituted acetylene XXII can be achieved in the presence of a palladium catalyst such as tetrakis(triphenylphosphine)palladium(0) or bis(triphenylphosphine)palladium(II) chloride, and a copper(I) catalyst such as copper(I) iodide. The reaction can be carried out in an inert solvent such as pyrrolidine, at a temperature between room temperature and 80° C. for several hours.

The reduction of the acetylene XXII to the corresponding saturated alcohol XXIII can be achieved by hydrogenation in the presence of $PtO_2$ under 50 psi hydrogen atmosphere. The reaction can be carried out in a solvent such as ethyl acetate, at room temperature, for several hours.

The oxidation of alcohol XXIII to the corresponding acid IXa (wherein R1 is chloro and R2 is hydrogen) can be accomplished using methods well known to someone skilled in the art, by utilizing a variety of oxidizing agents. For example, $H_5IO_6/CrO_3$ can be used as the oxidant. The reaction can be carried out in a suitable solvent mixture, such as acetonitrile and water, at 0° C.

Scheme 3

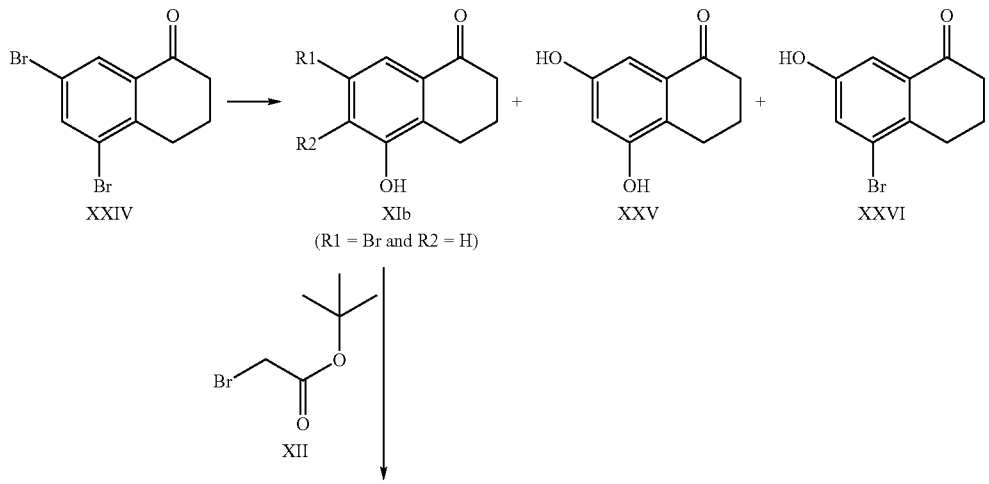

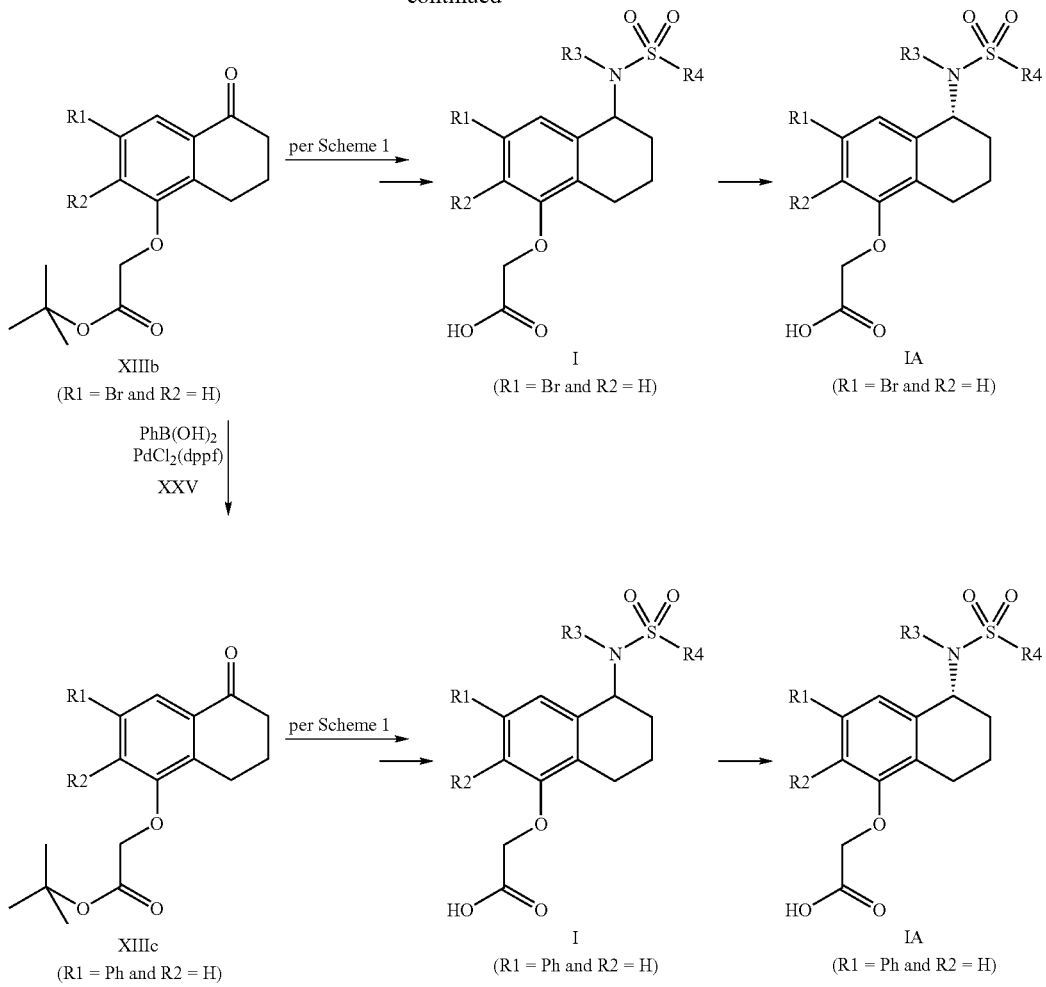

For the specific case where R1 is bromo and R2 is hydrogen, an alternative synthesis may be utilized to access the key intermediate XIIIb (prior to reductive amination), as outlined in Scheme 3. A non-regioselective Pd-catalyzed hydroxylation of the commercially available dibromo derivative XXIV provides the phenol derivative XIb in a single step. Two other products are also observed in the reaction, namely the dihydroxyl derivative XXV, and the undesired regioisomer XXVI. The intermediate XIb can then be separated and converted to esters XIIIb by treatment with tert-butyl bromoacetate (XII), as previously described. The compounds of interest I or IA, wherein R1 is bromo and R2 is hydrogen, are then prepared from XIIIb in a manner analogous to the one previously described above (in Scheme 1).

The intermediate XIIIb (prepared via the reaction of XIb with tert-butyl bromoacetate (XII), as described in Scheme 1) would undergo a Suzuki cross-coupling reaction with phenylboronic acid to provide the phenyl-substituted derivative XIIIc. A similar sequence of reactions as described in Scheme 1 would then provide the compounds of interest I or IA, wherein R1 is phenyl and R2 is hydrogen.

The Pd-catalyzed hydroxylation of 5,7-dibromo-3,4-dihydro-2H-naphthalen-1-one (XXIV) to produce the phenol derivative XIb can be achieved using the methodology described by Buchwald et. al (*J. Am. Chem. Soc.* 2006, 128, 10694). The reaction can be carried out with potassium hydroxide, using catalytic amounts of tris(dibenzylideneacetone)dipalladium (0), and di-tert-butyl-(2',4',6'-triisopropyl-biphenyl-2-yl)-phosphane, in a mixture of water and dioxane, at 100° C.

The conversion of XIb to XIIIb can be accomplished as described above (Scheme 1). The Pd-catalyzed Suzuki coupling of (3-bromo-5-oxo-5,6,7,8-tetrahydro-naphthalen-1-yloxy)-acetic acid tert-butyl ester (XIIIb) with phenylboronic acid is then carried out in the presence of a Pd catalyst, such as [1,1'-bis(diphenylphosphino)ferrocene]dichloropalladium, and a base such as cesium carbonate, in a solvent such as dimethoxyethane, at 95° C., for several hours.

The intermediate XIIIc can then be converted to the compounds of interest I or IA wherein R1 is phenyl and R2 is hydrogen, as previously described above (in Scheme 1).

Scheme 4

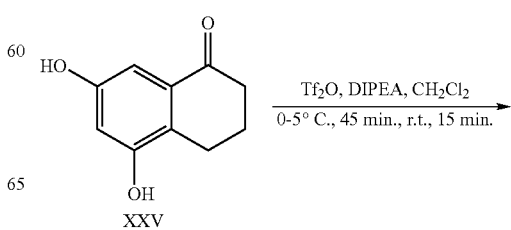

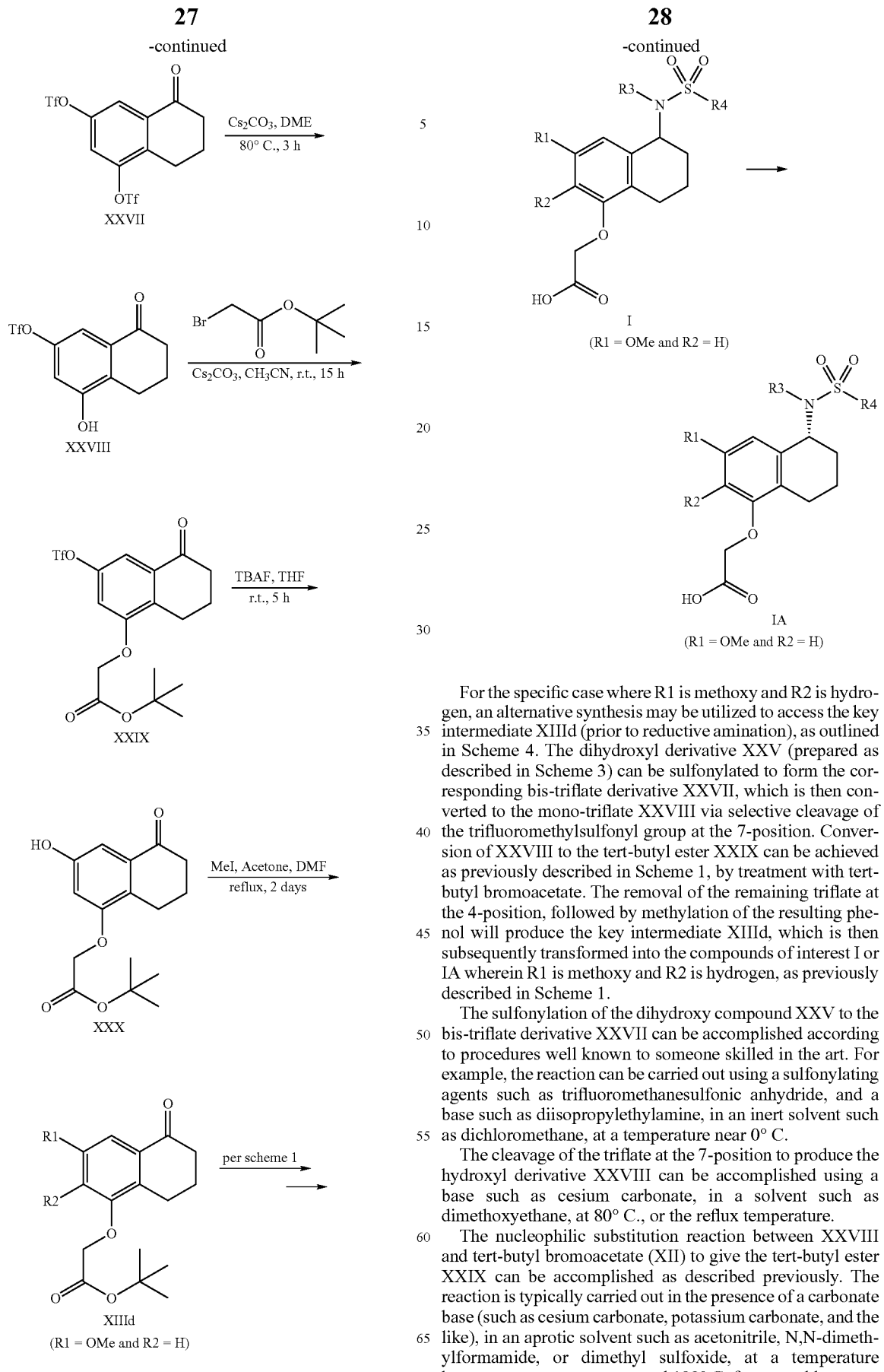

For the specific case where R1 is methoxy and R2 is hydrogen, an alternative synthesis may be utilized to access the key intermediate XIIId (prior to reductive amination), as outlined in Scheme 4. The dihydroxyl derivative XXV (prepared as described in Scheme 3) can be sulfonylated to form the corresponding bis-triflate derivative XXVII, which is then converted to the mono-triflate XXVIII via selective cleavage of the trifluoromethylsulfonyl group at the 7-position. Conversion of XXVIII to the tert-butyl ester XXIX can be achieved as previously described in Scheme 1, by treatment with tert-butyl bromoacetate. The removal of the remaining triflate at the 4-position, followed by methylation of the resulting phenol will produce the key intermediate XIIId, which is then subsequently transformed into the compounds of interest I or IA wherein R1 is methoxy and R2 is hydrogen, as previously described in Scheme 1.

The sulfonylation of the dihydroxy compound XXV to the bis-triflate derivative XXVII can be accomplished according to procedures well known to someone skilled in the art. For example, the reaction can be carried out using a sulfonylating agents such as trifluoromethanesulfonic anhydride, and a base such as diisopropylethylamine, in an inert solvent such as dichloromethane, at a temperature near 0° C.

The cleavage of the triflate at the 7-position to produce the hydroxyl derivative XXVIII can be accomplished using a base such as cesium carbonate, in a solvent such as dimethoxyethane, at 80° C., or the reflux temperature.

The nucleophilic substitution reaction between XXVIII and tert-butyl bromoacetate (XII) to give the tert-butyl ester XXIX can be accomplished as described previously. The reaction is typically carried out in the presence of a carbonate base (such as cesium carbonate, potassium carbonate, and the like), in an aprotic solvent such as acetonitrile, N,N-dimethylformamide, or dimethyl sulfoxide, at a temperature between room temperature and 100° C. for several hours.

The cleavage of the remaining triflate functionality in XXIX to provide the hydroxyl derivative XXX may be accomplished by treatment with tetrabutylammonium fluoride, in a solvent such as tetrahydrofuran, at room temperature, for several hours.

The O-methylation of phenol XXX, to provide the methoxy derivative XIIId, can be carried out using methods that are well known to someone skilled in the art. For example, the reaction can be performed using a methylating agent such as iodomethane or dimethyl sulfate, in the presence of a base such as potassium carbonate, in a solvent such as acetone, acetonitrile, 1,4-dioxane, or N,N-dimethylformamide, or mixtures thereof, at a temperature between room temperature and reflux temperature (preferably the reflux temperature), for several hours.

The intermediate XIIId can then be converted to the compounds of interest I or IA wherein R1 is methoxy and R2 is hydrogen, as previously described above (in Scheme 1).

EXAMPLES

Materials and Instrumentation in General

Intermediates and final compounds were purified by either flash chromatography and/or preparative HPLC (high performance liquid chromatography). Flash chromatography was performed using (1) the Biotage SP1™ system and the Quad 12/25 Cartridge module from Biotage AB) or (2) the ISCO CombiFlash® chromatography instrument (from Teledyne Isco, Inc.); unless otherwise noted. The silica gel brand and pore size utilized were: (1) KP-SIL™ 60 Å, particle size: 40-60 micron (from Biotage AB); (2) Silica Gel CAS registry No: 63231-67-4, particle size: 47-60 micron; or (3) ZCX from Qingdao Haiyang Chemical Co., Ltd, pore size: 200-300 mesh or 300-400 mesh. Preparative HPLC was performed on a reversed phase column using an Xbridge™ Prep $C_{18}$ (5 μm, OBD™ 30×100 mm) column (from Waters Corporation), a SunFire™ Prep $C_{18}$ (5 μm, OBD™ 30×100 mm) column (from Waters Corporation), or a Varian Pursuit® C-18 column 20×150 mm (from Varian, Inc.).

Mass spectrometry (MS) or high resolution mass spectrometry (HRMS) was performed using a Waters® ZQ™ 4000 (from Waters Corporation), a Waters® Alliance® 2795-ZQ™2000 (from Waters Corporation), a Waters® Quattro Micro™ API (from Waters Corporation), or an MDS Sciex™ API-2000™n API (from MDS Inc.). Mass spectra data generally only indicates the parent ions unless otherwise stated. MS or HRMS data is provided for a particular intermediate or compound where indicated.

Nuclear magnetic resonance spectroscopy (NMR) was performed using a Varian® Mercury300 NMR spectrometer (for the HNMR spectrum acquired at 300 MHz) and a Varian® Inova400 NMR spectrometer (for the HNMR spectrum acquired at 400 MHz) both from Varian Inc. NMR data is provided for a particular intermediate or compound where indicated.

The microwave assisted reactions were carried out in a Biotage Initiator™ Sixty (or its early models) (from Biotage AB) or by a CEM Discover® model (with gas addition accessory) (from CEM Corporation).

Chiral separation was performed by supercritical fluid chromatography (SFC) using a Multigram® III instrument (from Thar Technologies, Inc.).

All reactions involving air-sensitive reagents were performed under an inert atmosphere. Reagents were used as received from commercial suppliers unless otherwise noted.

Preparation of Key Intermediates

Preparation of 4-(4-Chloro-2-methoxy-phenyl)-butyric acid (IXa)-Prepared as described in Scheme 2

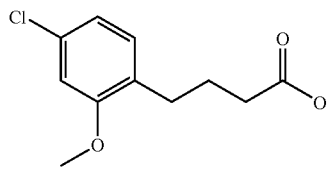

4-(4-Chloro-2-methoxy-phenyl)-but-3-yn-1-ol

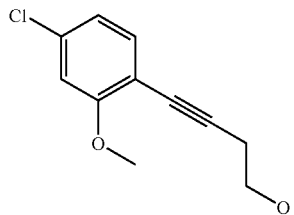

To a stirred solution of 2-bromo-5-chloroanisole (2 g, 9 mmol), Pd(PPh$_3$)$_4$ (520 mg, 0.45 mmol), and CuI (400 mg) in pyrrolidine (20 mL) was added a solution of 3-butyn-1-ol (1.26 g, 18 mmol) in pyrrolidine (30 mL). The reaction mixture was stirred at 80° C. for 6 h, and then concentrated in vacuo. The resulting residue was extracted with ethyl acetate and the organic phase was washed with 1N hydrochloric acid, followed by water, then brine, and dried over sodium sulfate. Upon removal of the solvent under reduced pressure, the crude product was subjected to column chromatography on silica gel (gradient elution with 0%-40% EtOAc/hexane) to give 4-(4-chloro-2-methoxy-phenyl)-but-3-yn-1-ol as a colorless oil (1.46 g, 76.7%). $^1$H NMR (300 MHz, CDCl$_3$) δ ppm 7.29 (d, J=8.2 Hz, 1H), 6.88 (dd, J=8.2, 1.6 Hz, 1H), 6.85 (d, J=1.6 Hz, 1H), 3.87 (s, 3H), 3.82 (t, J=6.2 Hz, 2H), 2.73 (t, J=6.2 Hz, 2H), 1.92 (br. s, 1H).

4-(4-Chloro-2-methoxy-phenyl)-butan-1-ol

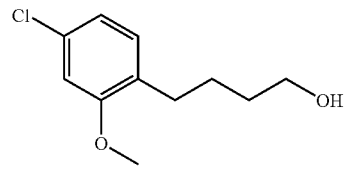

A solution of 4-(4-chloro-2-methoxy-phenyl)-but-3-yn-1-ol (2.2 g, 10.4 mmol) and PtO$_2$ (200 mg) in ethyl acetate (15 mL) was hydrogenated under 50 psi hydrogen atmosphere until no more hydrogen uptake was observed. The reaction mixture was then filtered and concentrated in vacuo. The crude product was subjected to column chromatography on silica gel (gradient elution with 0%-40% EtOAc/hexane) to give 4-(4-chloro-2-methoxy-phenyl)-butan-1-ol as a colorless oil (2 g, 89.7%). $^1$H NMR (300 MHz, CDCl$_3$) δ ppm 7.03

(d, J=8.2 Hz, 1H), 6.86 (dd, J=8.2, 1.6 Hz, 1H), 6.81 (d, J=1.6 Hz, 1H), 3.81 (s, 3H), 3.66 (t, J=6.0 Hz, 2H), 2.49-2.65 (m, 2H), 1.50-1.72 (m, 5H).

4-(4-Chloro-2-methoxy-phenyl)-butyric acid (IXa)

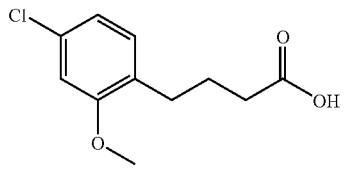

A stock solution of $H_5IO_6/CrO_3$ was prepared by dissolving $H_5IO_6$ (11.4 g, 50 mmol) and $CrO_3$ (23 mg, 1.2 mol %) in wet acetonitrile (0.75 v % water) to a volume of 114 mL (complete dissolution typically required 1-2 hours). The $H_5IO_6/CrO_3$ solution (8.7 mL) was then added to a solution of 4-(4-chloro-2-methoxy-phenyl)-butan-1-ol (330 mg, 1.54 mmol) in wet acetonitrile (10 mL, 0.75 v % water) dropwise over 30-60 minutes while maintaining the reaction temperature at 0-5° C. The resulting reaction mixture was stirred at 0° C. for 0.5 h, when completion of the reaction was confirmed by LC/MS. The reaction was quenched by the addition of an aqueous solution of $Na_2HPO_4$ (0.60 g in 10 mL $H_2O$). Ethyl acetate was added and the organic layer was separated and washed with water and then brine. The organic layer was then dried and concentrated to give the crude carboxylic acid, which was purified by flash chromatography on silica gel (gradient elution with 25%-50% EtOAc/hexane) to give 4-(4-chloro-2-methoxy-phenyl)-butyric acid as a white solid (200 mg, 56.9%). $^1$H NMR (300 MHz, DMSO-$d_6$) δ ppm 11.64 (br. s, 1H), 7.12 (d, J=8.2 Hz, 1H), 7.00 (s, 1H), 6.92 (d, J=8.2 Hz, 1H), 3.79 (s, 3H), 2.51-2.57 (m, 2H), 2.18 (t, J=7.4 Hz, 2H), 1.72 (quin, J=7.4 Hz, 2H).

Preparation of 7-Bromo-5-hydroxy-3,4-dihydro-2H-naphthalen-1-one (XIb)-Prepared as described in Scheme 3

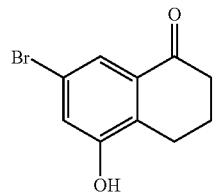

To a mixture of tris(dibenzylideneacetone)dipalladium(0) (210 mg, 0.23 mmol), di-tert-butyl-(2',4',6'-triisopropyl-biphenyl-2-yl)-phosphane (403 mg, 0.92 mmol), and potassium hydroxide (1.67 g, 25.32 mmol) were added degassed water (5.25 mL) and a solution of 5,7-dibromo-3,4-dihydro-2H-naphthalen-1-one (3.5 g, 11.51 mmol) in dioxane (7.0 mL) at room temperature under nitrogen. The resulting suspension was heated to 100° C. for 3.5 h. The reaction mixture was then cooled to room temperature, diluted with water (~10 mL) and acidified with 1N HCl solution. The resulting mixture was extracted with ethyl acetate (2×100 mL) and the combined organic extracts were washed with brine (200 mL), then dried over anhydrous magnesium sulfate, filtered, and concentrated in vacuo. The crude product was purified by chromatography, using an ISCO (120 g) column (gradient elution with 5-30% ethyl acetate in hexanes) to obtain 7-bromo-5-hydroxy-3,4-dihydro-2H-naphthalen-1-one (0.45 g, 16%) as a white solid: ES(−)-HRMS m/e calcd. (calculated) for $C_{10}H_9O_2Br$ (M−H)$^-$ 238.9713, obsd. (observed) 238.9712. Two other side products were also isolated and characterized as 5-bromo-7-hydroxy-3,4-dihydro-2H-naphthalen-1-one (0.3 g, 10%) and 5,7-dihydroxy-3,4-dihydro-2H-naphthalen-1-one (0.191 g, 7%).

Preparation of (3-bromo-5-oxo-5,6,7,8-tetrahydro-naphthalen-1-yloxy)-acetic acid tert-butyl ester (XIIIb)-Prepared as described in Scheme 3

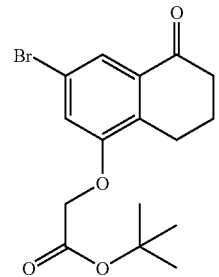

To a suspension of 7-bromo-5-hydroxy-3,4-dihydro-2H-naphthalen-1-one (XIb, 158 mg, 0.65 mmol) and cesium carbonate (431 mg, 1.31 mmol) in acetonitrile (5 mL) was added tert-butyl bromoacetate (XII, 261 mg, 1.31 mmol) at room temperature under nitrogen. The resulting suspension was stirred for 15 h at room temperature and then concentrated under vacuum. The residue was diluted with water (10 mL) and ethyl acetate (20 mL). The aqueous layer was separated and extracted with ethyl acetate (20 mL), and the combined organic extracts were washed with brine solution (50 mL), then dried over anhydrous magnesium sulfate, filtered, and concentrated in vacuo to give the crude product. Chromatography using an ISCO (40 g) column, (gradient elution with 5-25% ethyl acetate in hexanes) provided (3-bromo-5-oxo-5,6,7,8-tetrahydro-naphthalen-1-yloxy)-acetic acid tert-butyl ester (150 mg, 64%) as a white solid: ES(+)-HRMS m/e calcd. for $C_{16}H_{19}O_4Br$ (M+Na)$^+$ 377.0359, obsd. 377.0358.

Preparation of (5-oxo-3-phenyl-5,6,7,8-tetrahydro-naphthalen-1-yloxy)-acetic acid tert-butyl ester (XIIIc)-Prepared as described in Scheme 3

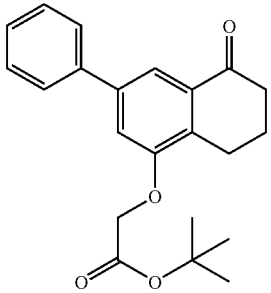

To a mixture of (3-bromo-5-oxo-5,6,7,8-tetrahydro-naphthalen-1-yloxy)-acetic acid tert-butyl ester (XIIIb, 78 mg, 0.22 mmol), phenylboronic acid (55.3 mg, 0.44 mmol), [1,1'-bis(diphenylphosphino)ferrocene]dichloropalladium(II) (24.1 mg, 0.033 mmol), and cesium carbonate (144.8 mg, 0.44 mmol) was added dimethoxyethane (2 mL) at room temperature under nitrogen. The resulting brown reaction mixture was heated at 95° C. for 15 h. Then, the reaction mixture was cooled to room temperature, and diluted with water (20 mL) and ethyl acetate (20 mL). The aqueous layer was separated and extracted with ethyl acetate (20 mL), and the combined organic extracts were washed with water (50 mL) and brine solution (50 mL), then dried over anhydrous magnesium sulfate, filtered, and concentrated under vacuum to provide the colored residue. Chromatography using an ISCO (12 g) column, (gradient elution with 2-25% ethyl acetate in hexanes) afforded (5-oxo-3-phenyl-5,6,7,8-tetrahydro-naphthalen-1-yloxy)-acetic acid tert-butyl ester (54 mg, 70%) as a white solid: ES(+)-HRMS m/e calcd. for $C_{22}H_{24}O_4$ (M+Na)$^+$ 375.1567, obsd. 375.1567.

Preparation of (3-Methoxy-5-oxo-5,6,7,8-tetrahydro-naphthalen-1-yloxy)-acetic acid tert-butyl ester (XIIId)-Prepared as described in Scheme 4

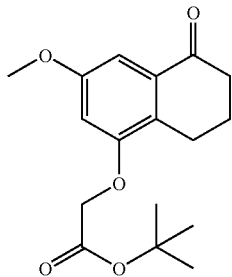

Trifluoro-methanesulfonic acid 8-oxo-4-trifluoromethanesulfonyloxy-5,6,7,8-tetrahydro-naphthalen-2-yl ester (XXVII)

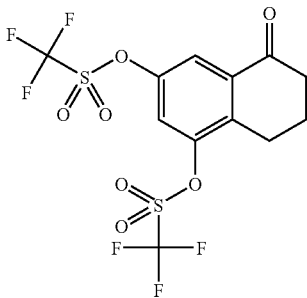

To a suspension of 5,7-dihydroxy-3,4-dihydro-2H-naphthalen-1-one (XXV, prepared as described in Scheme 3 above, 320 mg, 1.79 mmol) in dichloromethane (25 mL) was added diisopropylethylamine (925 mg, 7.16 mmol) at −5 to 0° C. To the resulting solution was then added trifluoromethanesulfonic anhydride (1.06 g, 3.76 mmol) dropwise over 5 minutes at this temperature. The resulting brown solution was stirred for 45 minutes at ~0-5° C. and then warmed to room temperature and stirred for another 15 minutes. The reaction mixture was then diluted with dichloromethane (50 mL) and water (70 mL). The aqueous layer was separated and extracted with dichloromethane (25 mL). The combined organic extracts were washed with brine (100 mL), dried over anhydrous magnesium sulfate, filtered, and concentrated under vacuum. The crude product was dissolved in dichloromethane (10 mL) and diluted with hexanes (50 mL). The brown solution was stored in the refrigerator for 15 h. The resulting solids were collected by filtration and washed with hexanes. After drying in the air, trifluoro-methanesulfonic acid 8-oxo-4-trifluoromethanesulfonyloxy-5,6,7,8-tetrahydro-naphthalen-2-yl ester (0.548 g, 69%) was obtained as a light brown solid: EI(+)-HRMS m/e calcd. for $C_{12}H_8F_6O_7S_2$ (M+) 442.9616, obsd. 442.9618.

Trifluoro-methanesulfonic acid 4-hydroxy-8-oxo-5,6,7,8-tetrahydro-naphthalen-2-yl ester (XXVIII)

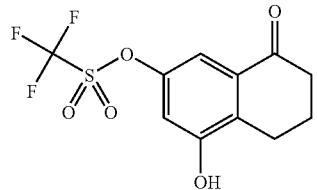

To a mixture of trifluoro-methanesulfonic acid 8-oxo-4-trifluoromethanesulfonyloxy-5,6,7,8-tetrahydro-naphthalen-2-yl ester (XXVII, 542 mg, 1.23 mmol) and cesium carbonate (599 mg, 1.84 mmol) was added dimethoxyethane (11 mL) at room temperature. The resulting brown suspension was then heated at 80° C. and stirred for 3 h. The reaction mixture was cooled to room temperature and diluted with saturated ammonium chloride solution (50 mL), and then extracted with ethyl acetate (2×50 mL). The combined organic extracts were washed with brine (100 mL), dried over anhydrous magnesium sulfate, filtered, and concentrated under vacuum. The crude product was dissolved in dichloromethane (15 mL) and diluted with hexanes (100 mL), then heated to remove the dichloromethane. The cloudy solution was then stored in the refrigerator for 15 h. The resulting solids were collected by filtration and washed with hexanes. After drying in the air, trifluoro-methanesulfonic acid 4-hydroxy-8-oxo-5,6,7,8-tetrahydro-naphthalen-2-yl ester (182 mg, 51%) was obtained as a dark brown solid: ES(−)-HRMS m/e calcd. for $C_{11}H_9F_3O_5S$ (M−H)$^−$ 309.0050, obsd. 309.0049.

(5-Oxo-3-trifluoromethanesulfonyloxy-5,6,7,8-tetrahydro-naphthalen-1-yloxy)-acetic acid tert-butyl ester (XXIX)

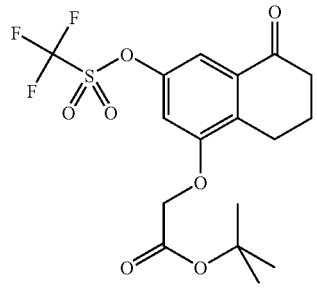

To a suspension of trifluoro-methanesulfonic acid 4-hydroxy-8-oxo-5,6,7,8-tetrahydro-naphthalen-2-yl ester (XXVIII, 177 mg, 0.57 mmol) and cesium carbonate (372 mg, 1.14 mmol) in acetonitrile (5 mL) was added tert-butyl bromoacetate (167 mg, 0.86 mmol) at room temperature under nitrogen. The resulting suspension was stirred for 15 h at room temperature, and then concentrated under vacuum. The residue was diluted with water (10 mL) and ethyl acetate (20 mL). The aqueous layer was separated and extracted with ethyl acetate (20 mL). The combined organic extracts were washed with brine (50 mL), dried over anhydrous magnesium sulfate, filtered, and concentrated in vacuo. The crude product was purified by ISCO (40 g) column chromatography, (gradient elution with 5-25% ethyl acetate in hexanes) to provide (5-oxo-3-trifluoromethanesulfonyloxy-5,6,7,8-tetrahydro-naphthalen-1-yloxy)-acetic acid tert-butyl ester (143 mg, 59%) as a white solid: ES(+)-HRMS m/e calcd. for $C_{17}H_{19}F_3O_7S$ (M+H)$^+$425.0877, obsd. 425.0876.

(3-Hydroxy-5-oxo-5,6,7,8-tetrahydro-naphthalen-1-yloxy)-acetic acid tert-butyl ester (XXX)

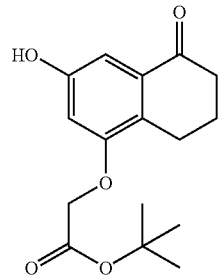

To a solution of (5-oxo-3-trifluoromethanesulfonyloxy-5,6,7,8-tetrahydro-naphthalen-1-yloxy)-acetic acid tert-butyl ester (XXIX, 140 mg, 0.33 mmol) in tetrahydrofuran (5 mL) was added a 1.0 M solution of tetrabutylammonium fluoride (660 µL, 0.66 mmol) in tetrahydrofuran at room temperature under nitrogen. The resulting light yellow solution was stirred for 5 h at room temperature, and then diluted with water (10 mL) and 1.0N hydrochloric acid (5 mL). The mixture was extracted with ethyl acetate (2×35 mL). The combined organic extracts were washed with brine (50 mL), dried over anhydrous magnesium sulfate, filtered, and concentrated in vacuo. The crude product was purified by ISCO (40 g) column chromatography (gradient elution with 5-50% ethyl acetate in hexanes) to provide (3-hydroxy-5-oxo-5,6,7,8-tetrahydro-naphthalen-1-yloxy)-acetic acid tert-butyl ester (82 mg, 85%) as a yellow solid: ES(+)-HRMS m/e calcd. for $C_{16}H_{20}O_5$ (M+H)$^+$293.1384, obsd. 293.1383.

(3-Methoxy-5-oxo-5,6,7,8-tetrahydro-naphthalen-1-yloxy)-acetic acid tert-butyl ester (XIIId)

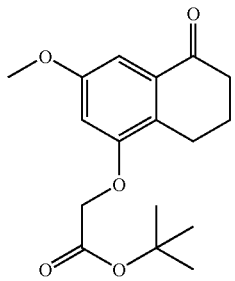

To a suspension of (3-hydroxy-5-oxo-5,6,7,8-tetrahydro-naphthalen-1-yloxy)-acetic acid tert-butyl ester (XXX, 78 mg, 0.27 mmol) and potassium carbonate (111 mg, 0.8 mmol) in acetone (4 mL) and DMF (2 mL) was added iodomethane (114 mg, 0.8 mmol) at room temperature under nitrogen. The resulting red-brown suspension was heated at reflux for 2 days. The reaction mixture was then cooled to room temperature and diluted with water (10 mL) and brine (10 mL). The resulting mixture was extracted with ethyl acetate (2×35 mL). The combined organic extracts were washed with brine (50 mL), dried over anhydrous magnesium sulfate, filtered, and concentrated in vacuo. The crude product was purified by using ISCO (40 g) column chromatography (gradient elution with 5-40% ethyl acetate in hexanes) to obtain (3-methoxy-5-oxo-5,6,7,8-tetrahydro-naphthalen-1-yloxy)-acetic acid tert-butyl ester (76 mg, 94%) as a light yellow solid: ES(+)-HRMS m/e calcd. for $C_{17}H_{22}O_5$ (M+H)$^+$307.1540, obsd. 307.1540.

Preparation of Sulfonyl Chlorides

Preparation of 5-(3-Isopropyl-phenyl)-pyridine-2-sulfonyl chloride

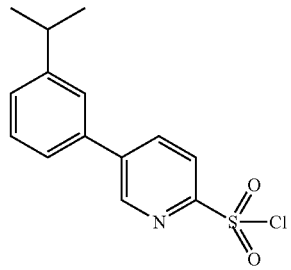

3-Isopropyl-phenylboronic acid

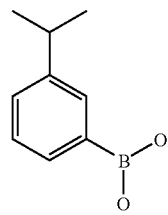

n-BuLi (7.7 mL, 14.0 mmol) was added dropwise to a stirred solution of 1-bromo-3-isopropyl-benzene (2.4 g, 12.1 mmol) in dry THF (40 mL) over 30 min at −70° C. under nitrogen. The reaction mixture was degassed for 15 min, and triisopropylborate (2.63 g, 14.0 mmol) was added at the same temperature. The reaction mixture was gradually warmed to 0° C. during 90 min and stirred for an additional 30 min at 0° C. The reaction mixture was then cooled to −20° C., and an aqueous solution of 2N HCl (20 mL) was added slowly. THF was distilled off and the reaction mixture was extracted with ethyl acetate (2×20 mL). The combined organic layers were dried over $Na_2SO_4$, and concentrated in vacuo to obtain the crude product (1.85 g, 93.5%), which was used for the next step without further purification.

2-Chloro-5-(3-isopropyl-phenyl)-pyridine

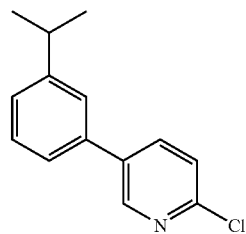

To a stirred solution of 5-bromo-2-chloropyridine (1.27 g, 6.63 mmol) in toluene (30 mL) was added an ethanolic solution (10 mL) of 3-isopropyl-phenylboronic acid (1.8 g, 11.28 mmol) followed by water (10 mL) and potassium carbonate (2.76 g, 20.0 mmol). The resulting mixture was degassed for 15 min (by purging with argon). At this time, Pd(PPh$_3$)$_4$ (0.613 g, 0.53 mmol) was added under argon and the reaction mixture was heated at 80° C. for 4 h. The reaction mixture was then cooled to room temperature and extracted with ethyl acetate (3×10 mL). The combined organic layers were washed with water (2×10 mL), dried over Na$_2$SO$_4$ and concentrated in vacuo to obtain the crude product, which was purified over silica gel (Biotage column chromatography, 2% ethyl acetate in hexane) to afford 0.900 g (59%) of 2-chloro-5-(3-isopropyl-phenyl)-pyridine.

2-Benzylsulfanyl-5-(3-isopropyl-phenyl)-pyridine

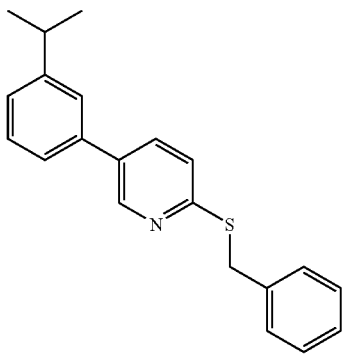

A solution of phenyl-methanethiol (0.8 mL, 5.84 mmol) in DMF (5 mL) was treated with NaH (0.140 g, 5.84 mmol) at room temperature under argon. After 15 min of stirring, the reaction mixture was treated with a solution of 2-chloro-5-(3-isopropyl-phenyl)-pyridine (0.900 g, 3.90 mmol) in DMF (15 mL). After 2 h of additional stirring at room temperature (reaction was monitored by TLC), the reaction mixture was quenched with ice cold water (20 mL), and extracted with ethyl acetate (3×10 mL). The combined organic layers were washed with water (2×10 mL), dried over Na$_2$SO$_4$, and concentrated in vacuo to obtain a crude product, which was purified over silica gel (Biotage column chromatography, gradient elution using 0-1% ethyl acetate in hexane) to furnish 2-benzylsulfanyl-5-(3-isopropyl-phenyl)-pyridine (0.680 g, 54.71%).

5-(3-Isopropyl-phenyl)-pyridine-2-sulfonyl chloride

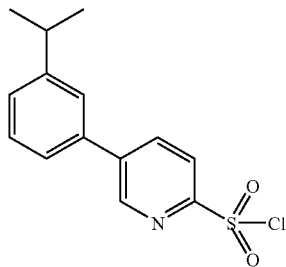

Chlorine gas was bubbled through a stirred solution of 2-benzylsulfanyl-5-(3-isopropyl-phenyl)-pyridine (0.680 g, 2.13 mmol) in carbon tetrachloride-water mixture (5:1; 30 mL) at 0° C. After 15 min of additional stirring, argon was bubbled through the reaction mixture, which was then quenched with ice (~10 mL) and extracted with dichloromethane (2×20 mL). The combined organic layers were dried over Na$_2$SO$_4$ and concentrated in vacuo to obtain 5-(3-isopropyl-phenyl)-pyridine-2-sulfonyl chloride (0.700 g, 71.5%), which was used without further purification. $^1$H NMR (400 MHz, DMSO-d$_6$) δ ppm 8.92 (s, 1H), 8.72 (d, J=8.0 Hz, 1H), 8.13 (d, J=8.0 Hz, 1H), 7.74 (s, 1H), 7.66 (d, J=7.3 Hz, 1H), 7.48 (t, J=7.3 Hz, 1H), 7.40 (d, J=7.3 Hz, 1H), 2.92-3.06 (m, 1H), 1.27 (d, J=6.8 Hz, 6H).

Preparation of
3-fluoro-5-trifluoromethyl-benzenesulfonyl chloride

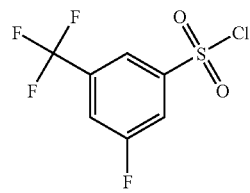

A mixture of 3-fluoro-5-trifluoromethyl-phenylamine (9.7 g, 54 mmol) in trifluoroacetic acid (100 mL) was cooled at 0° C. To the mixture was slowly added concentrated hydrochloric acid (10 mL), followed by a solution of sodium nitrite (4.7 g, 68 mmol) in water (5 mL) dropwise over 20 minutes. The mixture was stirred for another 10 minutes at 0° C., and then poured into a stirred mixture of acetic acid (120 mL), sulfurous acid (0.94 N aqueous sulfur dioxide solution, 120 mL), copper(II) chloride (9.2 g, 93 mmol) and copper(I) chloride (100 mg, 0.74 mmol) at 0° C. The resulting reaction mixture was allowed to warm to room temperature and stirred for 15 hours. Water (200 mL) was added, and the resulting mixture was extracted with ethyl acetate (100 mL×3). The combined organic layers were dried over sodium sulfate, filtered through a glass funnel and concentrated in vacuo. The residue was purified by column chromatography (20% ethyl acetate in petroleum ether) to afford 3-fluoro-5-trifluoromethyl-benzenesulfonyl chloride (3.7 g, 26%) as a white solid (reference: Cherney, R. J. et al., *J. Med. Chem.* 46 (2003) 1811). $^1$H NMR (400 MHz, CDCl$_3$) δ ppm 8.15 (s, 1H); 7.97-7.99 (d, J=4.0 Hz, 1H); 7.74-7.76 (d, J=4.0 Hz, 1H).

Preparation of
3-methoxy-5-trifluoromethyl-benzenesulfonyl chloride

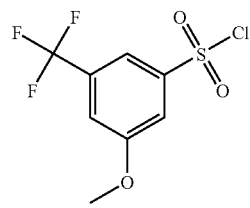

3-methoxy-5-trifluoromethyl-phenylamine (10 g, 54 mmol) was added to trifluoroacetic acid (100 mL) in a 250 mL flask, and the mixture was cooled to 0° C. Concentrated hydrochloric acid (10 mL) was then added slowly to the reaction mixture, followed by the dropwise addition of a solution of sodium nitrite (4.7 g, 68 mmol) in water (5 mL) over 20 min. The mixture was stirred for another 10 minutes at 0° C., and then poured into a stirred mixture of acetic acid (120 mL), sulfurous acid (0.94 N aqueous sulfur dioxide solution, 120 mL, 113 mmol), copper(II) chloride (9.2 g, 68 mmol) and copper(I) chloride (100 mg, 1 mmol) at 0° C. The reaction mixture was allowed to warm to room temperature and stirred for 15 hours, and then treated with water (200 mL). The aqueous layer was extracted with ethyl acetate (100 mL×3). The combined organic layers were dried over sodium sulfate, filtered through a glass funnel and concentrated in vacuo. The residue was purified by column chromatography (20% ethyl acetate in petroleum ether) to afford 3-methoxy-5-trifluoromethyl-benzenesulfonyl chloride (3.9 g, 27%) as a white solid [reference: Cherney, R. J. et al., *J. Med. Chem.* 46 (2003) 1811]. $^1$H NMR (400 MHz, CDCl$_3$) δ ppm 7.89 (s, 1H); 7.70 (s, 1H); 7.50 (s, 1H); 4.00 (s, 3H).

Preparation of Compounds of Interest

Example 1-1

Prepared as described in Scheme 1

[(R)-5-(3,5-Bis-trifluoromethyl-benzenesulfonylamino)-3-chloro-2-fluoro-5,6,7,8-tetrahydro-naphthalen-1-yloxy]-acetic acid

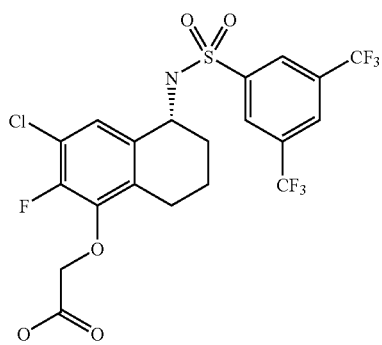

4-(4-Chloro-3-fluoro-2-hydroxy-phenyl)-4-oxo-butyric acid

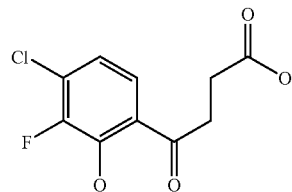

To a stirred and cooled solution of 2-fluoro-3-chloro-phenol (21.9 g, 0.15 mol) and succinic anhydride (15.3 g, 0.15 mol) in 1,1,2,2-tetrachloroethane (135 mL) was added anhydrous aluminum chloride (38.7 g, 0.29 mol) portion-wise. The reaction mixture was stirred at room temperature for 3 hours and then heated at 130° C. for 2 hours. After being cooled to room temperature, to the reaction mixture were added concentrated hydrochloric acid and ice alternatively in small portions. The resulting mixture was extracted with ethyl acetate (75 mL×3). The combined organic layers were evaporated. The solid residue was basified by slow addition of an aqueous solution of 2N sodium hydroxide solution under cooling conditions, and then extracted with ethyl acetate (30 mL×3). The aqueous layer was acidified by dropwise addition of concentrated hydrochloric acid to a pH of about 2, and then extracted with ethyl acetate (50 mL×3). The combined organic layers were dried over sodium sulfate, filtered, and concentrated in vacuo. Column chromatography (silica gel, 100-120 mesh, 15% ethyl acetate in hexane) gave 4-(4-chloro-3-fluoro-2-hydroxy-phenyl)-4-oxo-butyric acid (7.0 g, 19%). $^1$H NMR (400 MHz, DMSO-d$_6$) δ ppm 2.59 (t, J=6.26 Hz, 2H), 3.31 (t, J=6.28 Hz, 2H), 7.15 (d, J=6.56 Hz, 1H), 7.74 (d, J=6.56 Hz, 1H), 11.90-12.31 (m, 2H).

4-(4-Chloro-3-fluoro-2-hydroxy-phenyl)-butyric acid

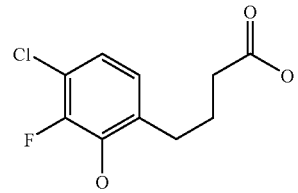

A mixture of zinc pieces (11.4 g), mercuric chloride (3.0 g), concentrated hydrochloric acid (4.6 mL) and water (140 mL) was stirred at room temperature for 5 minutes. The solvent was then decanted off. To the solid, were added concentrated hydrochloric acid (41 mL), water (18.6 mL), toluene (23 mL) and 4-(4-chloro-3-fluoro-2-hydroxy-phenyl)-4-oxo-butyric acid (8.6 g, 35 mmol). The resulting mixture was heated at reflux for 2 days, with the addition of concentrated hydrochloric acid in 12 hour intervals. The reaction mixture was cooled and extracted with ether (50 mL×3). The collected organic layers were dried over anhydrous sodium sulfate, filtered, and concentrated in vacuo to give pure 4-(4-chloro-3-fluoro-2-hydroxy-phenyl)-butyric acid (6.0 g, 74%), which was used in the next step without further purification. $^1$H NMR (400 MHz, DMSO-d$_6$) δ ppm 1.74 (dt, 2H), 2.20 (t, J=7.40 Hz, 2H), 2.57 (t, J=7.56 Hz, 2H), 6.87-6.92 (m, 2H), 9.90 (br s, 1H), 12.03 (br s, 1H).

4-(4-Chloro-3-fluoro-2-methoxy-phenyl)-butyric acid methyl Ester

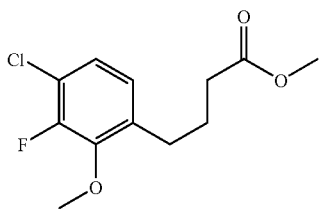

To a stirred solution of 4-(4-chloro-3-fluoro-2-hydroxyphenyl)-butyric acid (6.0 g, 0.026 mol) in acetone (20 mL) was added anhydrous potassium carbonate (9.7 g, 0.07 mol) at room temperature under nitrogen. After 10 minutes, dimethyl sulfate (5.49 mL, 0.058 mol) was added and the resulting mixture was stirred for an additional 3-4 hours. The solvent was removed in vacuo and the residue was extracted with dichloromethane (25 mL×3). The combined organic layers were washed with water (15 mL×2), dried over anhydrous sodium sulfate, filtered, and concentrated in vacuo to give 4-(4-chloro-3-fluoro-2-methoxy-phenyl)-butyric acid methyl ester (5.6 g, 83%), which was used in the next step without further purification. MS cald. for $C_{12}H_{14}ClFO_3$ 260, obsd. 261 [(M+H)$^+$].

4-(4-Chloro-3-fluoro-2-methoxy-phenyl)-butyric acid

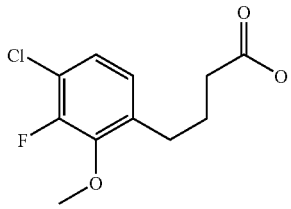

To a stirred solution of 4-(4-chloro-3-fluoro-2-methoxy-phenyl)-butyric acid methyl ester (5.6 g, 0.022 mol) in tetrahydrofuran (25 mL) was added a solution of lithium hydroxide (2.7 g, 0.067 mol) in water-methanol (2:1; 20 mL) at room temperature. The reaction mixture was stirred for 4 hours at room temperature. The solvents were removed under reduced pressure. The residue was diluted with water (25 mL) and then acidified by dropwise addition of aqueous 1N hydrochloric acid under cooling conditions. The resulting solution was extracted with ethyl acetate (30 mL×3). The combined organic layers were washed with water (30 mL), dried over anhydrous sodium sulfate, filtered, and concentrated in vacuo to give 4-(3,4-dichloro-2-methoxy-phenyl)-butyric acid (4.7 g, 87%), which was used in the next step without further purification. MS cald. for $C_{11}H_{12}ClFO_3$ 246, obsd. 247 [(M+H)$^+$].

7-Chloro-6-fluoro-5-methoxy-3,4-dihydro-2H-naphthalen-1-one

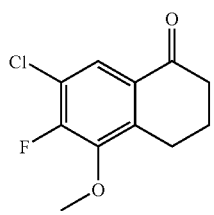

To a stirred solution of 4-(3,4-dichloro-2-methoxy-phenyl)-butyric acid (1.03 g, 8.10 mmol) in benzene (100 mL) were added phosphorus pentachloride (2.70 g, 12.96 mmol) and aluminum chloride (3.24 g, 24.30 mmol) at room temperature. After the reaction mixture was stirred for 4 hours, it was poured into ice water with continuous stirring, and then extracted with ethyl acetate (50 mL×3). The collected organic layers were subsequently washed with saturated sodium bicarbonate solution (20 mL) and water (20 mL), dried over anhydrous sodium sulfate, filtered, and concentrated in vacuo. Column chromatography (silica gel, 100-200 mesh, 10% ethyl acetate in hexane) gave 7-chloro-6-fluoro-5-methoxy-3,4-dihydro-2H-naphthalen-1-one (1.04 g, 58%).

$^1$H-NMR (400 MHz, CDCl$_3$) δ ppm 2.10 (dt, 2H), 2.61 (t, J=6.58 Hz, 2H), 2.90 (t, J=6.10 Hz, 2H), 3.93 (s, 3H), 7.83 (s, 1H).

7-Chloro-6-fluoro-5-hydroxy-3,4-dihydro-2H-naphthalen-1-one

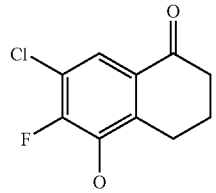

To a stirred solution of 7-chloro-6-fluoro-5-methoxy-3,4-dihydro-2H-naphthalen-1-one (1.04 g, 4.7 mmol) in xylene (35 mL) was added anhydrous aluminum chloride (1.93 g, 14.5 mmol) at room temperature. The reaction mixture was then heated at reflux for 1 hour. After being cooled to room temperature, the reaction mixture was slowly poured into ice water with continuous stirring. The resulting solution was extracted with ethyl acetate (50 mL×3). The collected organic layers were then washed with saturated sodium bicarbonate solution and water, dried with anhydrous sodium sulfate, filtered, and concentrated in vacuo to give the crude residue, which was washed with ether to afford 7-chloro-6-fluoro-5-hydroxy-3,4-dihydro-2H-naphthalen-1-one (0.90 g, 89%), which was used in the next step without further purification. MS cald. for $C_{10}H_8ClFO_2$ 214, obsd. 215 [(M+H)$^+$].

(3-Chloro-2-fluoro-5,6,7,8-tetrahydro-naphthalen-1-yloxy)-acetic acid tert-butyl ester To a stirred solution of 7-chloro-6-fluoro-5-hydroxy-3,4-dihydro-2H-naphthalen-1-one (0.90 g, 4.18 mmol) in dry N,N-dimethylformamide (10 mL) was added potassium carbonate (1.16 g, 8.36 mmol) and tert-butyl bromoacetate (1.22 g, 6.27 mmol) at room temperature and the resulting mixture was stirred for 2 hours, then extracted with ethyl acetate (25 mL×3), washed with water (25 mL×3), dried over anhydrous sodium sulfate, filtered, and concentrated in vacuo to afford (3-chloro-2-fluoro-5,6,7,8-tetrahydro-naphthalen-1-yloxy)-acetic acid tert-butyl ester (1.32 g, 96%), which was used in the next step without further purification. MS cald. for $C_{16}H_{18}ClFO_4$ 328, obsd. 329 [(M+H)+].

(5-Amino-3-chloro-2-fluoro-5,6,7,8-tetrahydro-naphthalen-1-yloxy)-acetic acid tert-butyl ester

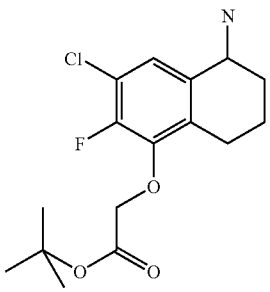

To a stirred and ice cold solution of (3-chloro-2-fluoro-5,6,7,8-tetrahydro-naphthalen-1-yloxy)-acetic acid tert-butyl ester (1.32 g, 4.01 mmol) and ammonium acetate (4.7 g, 61.0 mmol) in methanol (21 mL) was added sodium cyanoborohydride (504 mg, 8.02 mmol) under nitrogen. After 10 minutes of stirring at room temperature, the reaction mixture was heated at reflux for 4 hours. The solvent was removed under reduced pressure and to the residue was added saturated sodium bicarbonate solution (10 mL). The resulting solution was extracted with dichloromethane (25 mL×3). The organic layers were dried over anhydrous sodium sulfate, filtered, and concentrated in vacuo to afford (5-amino-3-chloro-2-fluoro-5,6,7,8-tetrahydro-naphthalen-1-yloxy)-acetic acid tert-butyl ester (1.26 g, 98%), which is used in the next step without further purification.

[5-(3,5-Bis-trifluoromethyl-benzenesulfonylamino)-3-chloro-2-fluoro-5,6,7,8-tetrahydro-naphthalen-1-yloxy]-acetic acid tert-butyl ester

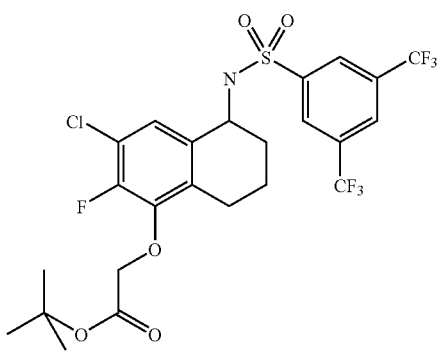

To a solution of (5-amino-3-chloro-2-fluoro-5,6,7,8-tetrahydro-naphthalen-1-yloxy)-acetic acid tert-butyl ester (125.0 mg, 0.38 mmol) and 3,5-di-(trifluoromethyl)benzene-1-sulfonyl chloride (0.117 g, 0.38 mmol) in dry tetrahydrofuran (5 mL) was added diisopropylethylamine (0.2 mL, 0.94 mmol) at 0° C. under nitrogen. After 2 hours of stirring at room temperature, the reaction mixture was concentrated in vacuo. The residue was partitioned between ethyl acetate and water. The collected organic layers were dried over anhydrous sodium sulfate, filtered, and concentrated under reduced pressure. Column chromatography (silica gel, 100-200 mesh, 5% ethyl acetate in hexane) gave [5-(3,5-bis-trifluoromethyl-benzenesulfonylamino)-3-chloro-2-fluoro-5,6,7,8-tetrahydro-naphthalen-1-yloxy]-acetic acid tert-butyl ester (163.2 mg, 71%). MS cald. for $C_{24}H_{23}ClF_7NO_5S$ 605, obsd. 604 [(M+H)+].

[(R)-5-(3,5-Bis-trifluoromethyl-benzenesulfonylamino)-3-chloro-2-fluoro-5,6,7,8-tetrahydro-naphthalen-1-yloxy]-acetic acid

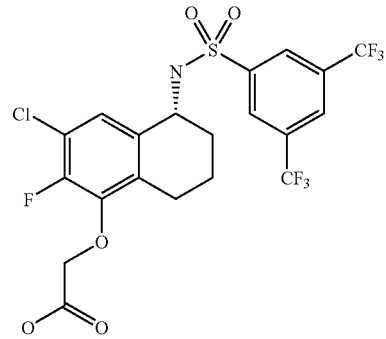

To a stirred solution of [5-(3,5-bis-trifluoromethyl-benzenesulfonylamino)-3-chloro-2-fluoro-5,6,7,8-tetrahydro-naphthalen-1-yloxy]-acetic acid tert-butyl ester (163.4 mg, 0.27 mmol) in tetrahydrofuran (4 mL) were added an aqueous (2 mL) solution of lithium hydroxide (0.036 g, 0.87 mmol) and methanol (1 mL) at room temperature and the resulting reaction mixture was stirred for 2 hours. The solvent was removed under reduced pressure. The residue was diluted with water (15 mL) and acidified with dilute hydrochloric acid, which resulted in the formation of a precipitate. The resulting mixture was extracted with ethyl acetate (15 mL×3). The combined organic layers was washed with water (15 mL×3), dried over anhydrous sodium sulfate, filtered, and concentrated in vacuo. Column chromatography (silica gel, 100-200 mesh, 50% ethyl acetate in hexane) gave [5-(3,5-bis-trifluoromethyl-benzenesulfonylamino)-3-chloro-2-fluoro-5,6,7,8-tetrahydro-naphthalen-1-yloxy]-acetic acid (130.4 mg, 88%). MS cald. for $C_{20}H_{15}ClF_7NO_5S$ 549, obsd. 548 (ESI+) [(M−H)+].

Chiral separation by super fluid chromatography (SFC) (Thar Technologies, Inc.'s Multigram® II instrument AD column, 100 bar back pressure, 35° C. oven, 10% methanol in carbon dioxide at 70 ml/min) gave (R)-[5-(3,5-bis-trifluoromethyl-benzenesulfonylamino)-3-chloro-2-fluoro-5,6,7,8-tetrahydro-naphthalen-1-yloxy]-acetic acid (58 mg). $^1$H NMR (400 MHz, DMSO-$d_6$) δ ppm 13.06 (br. s, 1H), 8.60 (d, J=7.9 Hz, 1H), 8.54 (s, 1H), 8.45 (s, 2H), 6.63 (d, J=6.8 Hz, 1H), 4.67 (s, 2H), 4.46-4.57 (m, 1H), 2.57-2.75 (m, 2H), 1.70-1.83 (m, 1H), 1.60 (m, 3H); MS cald. for $C_{20}H_{15}ClF_7NO_5S$ 549, obsd. 548 (ESI+) [(M−H)+].

Examples 1-2 to 1-52

The following examples 1-2 to 1-52 were prepared in an analogous manner to example 1-1 starting with commercially available substituted phenols and aryl sulfonyl chlorides. Where appropriate, the examples were prepared from the corresponding key intermediates IXa, XIb, or XIIIc, as described above. In cases where the example is depicted as a single enantiomer, a chiral separation of enantiomers was performed on the racemic final product, as described above.

| Example No. | Systematic Name | $^1$H NMR (400 MHz, DMSO-d$_6$) δ ppm | MS (M−+0H)$^-$ | Structure |
|---|---|---|---|---|
| 1-2 | [5-(3,5-Bis-trifluoromethyl-benzenesulfonyl-amino)-2-isopropyl-5,6,7,8-tetrahydro-naphthalen-1-yloxy]-acetic acid | (CDCl$_3$) 8.39 (s, 2H), 8.12 (s, 1H), 7.06 (d, J = 8.1 Hz, 1H), 6.80 (d, J = 8.1 Hz, 1H), 4.88 (d, J = 8.1 Hz, 1H), 4.52-4.62 (m, 1H), 4.41 (s, 2H), 3.13-3.30 (m, 1H), 2.80 (ddd, J = 17.2, 5.3, 5.1 Hz, 1H), 2.56-2.67 (m, 1H), 1.73-1.91 (m, 5H), 1.20 (d, J = 7.1 Hz, 6H) | 538 | 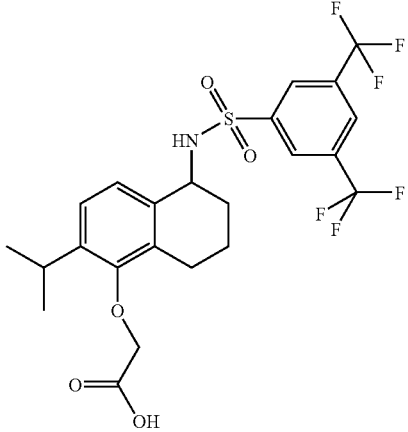 |
| 1-3 | [5-(3,5-Bis-trifluoromethyl-benzenesulfonyl-amino)-2-methyl-5,6,7,8-tetrahydro-naphthalen-1-yloxy]-acetic acid | 12.90 (br. s, 1H), 8.51 (br. s, 1H), 8.50 (d, J = 8.3 Hz, 1H), 8.44 (s, 2H), 6.91 (d, J = 8.0 6.65 (d, J = 8.0 Hz, 1H), 4.50 (br. s, 1H), 4.29 (s, 2H), 2.54-2.74 (m, 2H), 2.17 (s, 3H), 1.65-1.86 (m, 1H), 1.56 (br. s, 3H) | 510 | 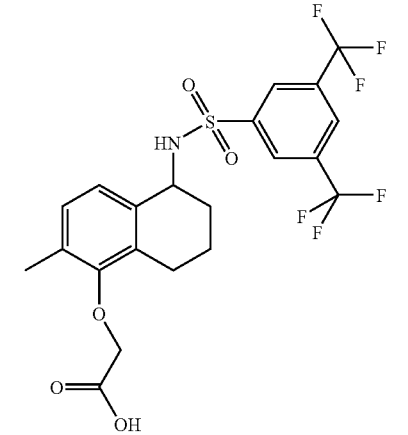 |
| 1-4 | [5-(3,5-Bis-trifluoromethyl-benzenesulfonyl-amino)-2-ethyl-5,6,7,8-tetrahydro-naphthalen-1-yloxy]-acetic acid | 12.88 (br. s, 1H), 8.48-8.52 (m, 2H), 8.45 (s, 2H), 6.94 (d, J = 7.8 Hz, 1H), 6.69 (d, J = 7.8 Hz, 1H), 4.47-4.54 (m, 1H), 4.28 (s, 2H), 2.52-2.72 (m, 4H), 1.66-1.82 (m, 1H), 1.50-1.67 (m, 3H), 1.10 (t, J = 7.3 Hz, 3H) | 524 | 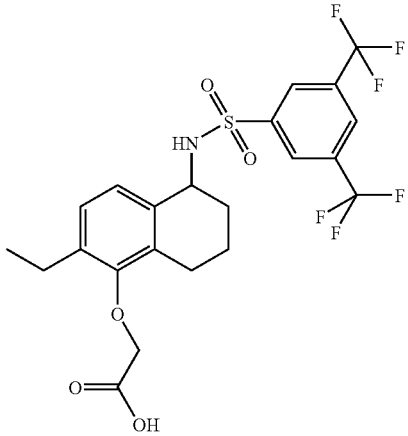 |

-continued

| Example No. | Systematic Name | $^1$H NMR (400 MHz, DMSO-d$_6$) δ ppm | MS (M−+0H)$^-$ | Structure |
|---|---|---|---|---|
| 1-5 | [5-(3,5-Bis-trifluoromethyl-benzenesulfonyl-amino)-3-chloro-2-methyl-5,6,7,8-tetrahydro-naphthalen-1-yloxy]-acetic acid | 8.50 (s, 1H), 8.42 (s, 2H), 6.56 (s, 1H), 4.42-4.53 (m, 1H), 4.30 (s, 2H), 2.54-2.70 (m, 2H), 2.17 (s, 3H), 1.68-1.80 (m, 1H), 1.56-1.68 (m, 3H) | 544 | 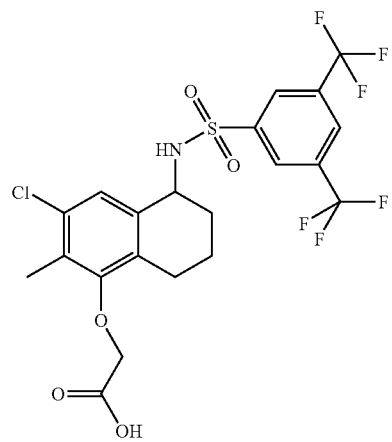 |
| 1-6 | [5-(3,5-Bis-trifluoromethyl-benzenesulfonyl-amino)-3-chloro-5,6,7,8-tetrahydro-naphthalen-1-yloxy]-acetic acid | 13.07 (br. s, 1H), 8.63 (d, J = 8.1 Hz, 1H), 8.54 (s, 1H), 8.46 (s, 2H), 6.78 (d, J = 1.6 Hz, H), 6.37 (d, J = 1.6 Hz, 1H), 4.71 (s, 2H), 4.44-4.63 (m, 1H), 2.54-2.70 (m, 2H), 1.69-1.85 (m, 1H), 1.60 (m, 3H) | 530 | 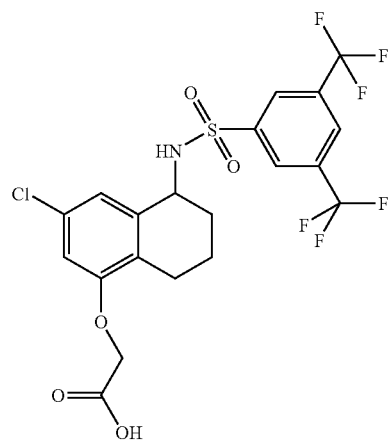 |
| 1-7 | [5-(3,5-Bis-trifluoromethyl-benzenesulfonyl-amino)-2-chloro-5,6,7,8-tetrahydro-naphthalen-1-yloxy]-acetic acid | 13.04 (br. s, 1H), 8.62 (d, J = 8.3 Hz, 1H), 8.53 (s, 1H), 8.46 (s, 2H), 6.79 (s, 1H), 6.38 (s, 1H), 4.73 (s, 2H), 4.45-4.60 (m, 1H), 2.42-2.49 (m, 2H), 1.70-1.83 (m, 1H), 1.53-1.70 (m, 3H) | 530 | 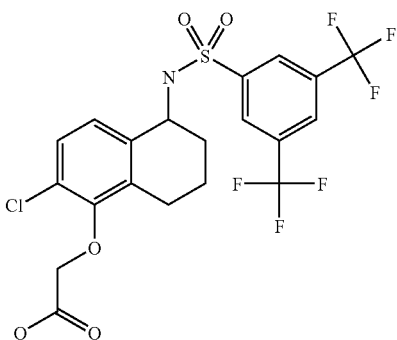 |

| Example No. | Systematic Name | $^1$H NMR (400 MHz, DMSO-d$_6$) δ ppm | MS (M−+0H)$^-$ | Structure |
|---|---|---|---|---|
| 1-8 | [(R)-5-(3,5-Bis-trifluoromethyl-benzenesulfonyl-amino)-2-chloro-5,6,7,8-tetrahydro-naphthalen-1-yloxy]-acetic acid | 13.08 (br. s, 1H), 8.62 (d, J = 8.1 Hz, 1H), 8.54 (s, 1H), 8.46 (s, 2H), 6.79 (d, J = 1.4 Hz, 1H), 6.38 (d, J = 1.4 Hz, 1H), 4.71 (s, 2H), 4.47-4.58 (m, 1H), 2.40-2.61 (m, 2H), 1.70-1.84 (m, 1H), 1.55-1.71 (m, 3H) | 530 | 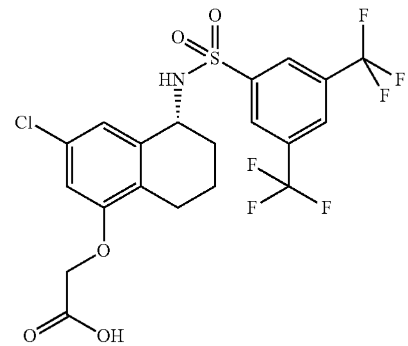 |
| 1-9 | [5-(3,5-Bis-trifluoromethyl-benzenesulfonyl-amino)-3-chloro-2-fluoro-5,6,7,8-tetrahydro-naphthalen-1-yloxy]-acetic acid | 13.07 (br. s, 1H), 8.61 (d, J = 8.1 Hz, 1H), 8.54 (s, 1H), 8.45 (s, 2H), 6.63 (d, J = 6.8 Hz, 1H), 4.68 (d, J = 2.0 Hz, 2H), 4.49-4.57 (m, 1H), 2.54-2.73 (m, 2H), 1.70-1.84 (m, 1H), 1.52- 1.69 (m, 3H) | 548 | 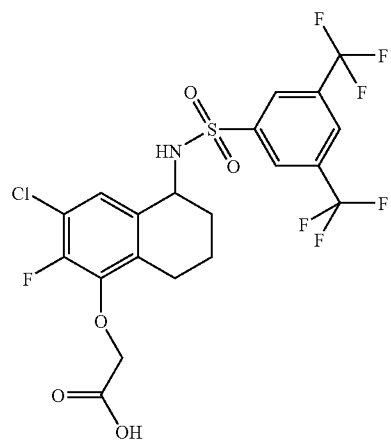 |
| 1-10 | [3-Chloro-5-(2,5-dichloro-benzenesulfonyl-2-fluoro-5,6,7,8-tetrahydro-naphthalen-1-yloxy]-acetic acid | 13.06 (br. s, 1H), 8.71 (d, J = 8.6 Hz, 1H), 8.00 (d, J = 2.2 Hz, 1H), 7.68-7.85 (m, 2H), 6.92 (d, J = 6.6 Hz, 1H), 4.68 (s, 2H), 4.29-4.47 (m, 1H), 2.58-2.69 (m, 2H), 1.83 (br. s, 1H), 1.62 (br. s, 3H) | 480 | 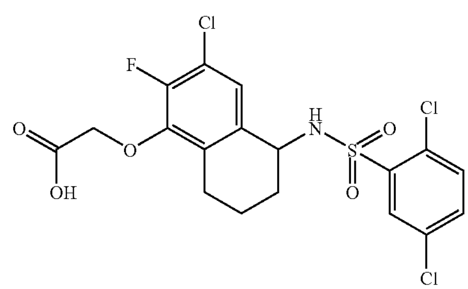 |
| 1-11 | [3-Chloro-5-(2,4-dichloro-benzenesulfonyl-amino)-5,6,7,8-tetrahydro-naphthalen-1-yloxy]-acetic acid | 13.05 (br. s, 1H), 8.61 (d, J = 9.3 Hz, 1H), 8.06 (d, J = 8.8 Hz, 1H), 7.93 (d, J = 2.0 Hz, 1H), 7.67 (dd, J = 8.8, 2.0 Hz, 1H), 6.80 (s, 1H), 6.69 (s, 1H), 4.73 (s, 2H), 4.26-4.38 (m, 1H), 2.44-2.50 (m, 2H), 1.77-1.89 (m, 1H), 1.53-1.67 (m, 3H) | 462 | 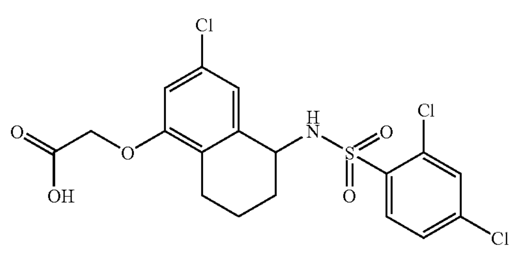 |

| Example No. | Systematic Name | ¹H NMR (400 MHz, DMSO-d₆) δ ppm | MS (M −+0H)⁻ | Structure |
|---|---|---|---|---|
| 1-12 | [5-(3,5-Bis-trifluoromethyl-benzenesulfonyl-amino)-2,3-dichloro-5,6,7,8-tetrahydro-naphthalen-1-yloxy]-acetic acid | 13.08 (s, 1H), 8.63 (d, J = 8.1 Hz, 1H), 8.55 (s, 1H), 8.46 (s, 2H), 6.81 (s, 1H), 4.51-4.61 (m, 1H), 4.48 (s, 2H), 2.54-2.81 (m, 2H), 1.71-1.85 (m, 1H), 1.54-1.71 (m, 3H) | 564 | 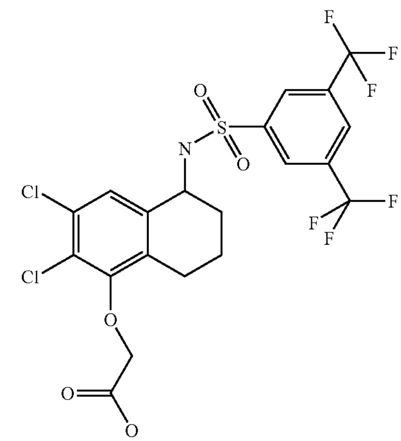 |
| 1-13 | [3-Chloro-5-(2,5-dichloro-benzenesulfonyl-amino)-5,6,7,8-tetrahydro-naphthalen-1-yloxy]-acetic acid | 12.88 (br. s, 1H), 8.55 (s, 1H), 8.52 (s, 2H), 7.10 (dd, J = 11.7, 8.7 Hz, 1H), 6.84 (dd, J = 8.7, 5.1 Hz, 1H), 5.22-5.30 (m, 1H), 4.64 (s, 2H), 2.78-2.90 (m, 1H), 2.57 (s, 3H), 2.43-2.49 (m, 1H), 1.80 (br. s, 1H), 1.50-1.76 (m, 2H), 1.46 (br. s, 1H) | 462 | 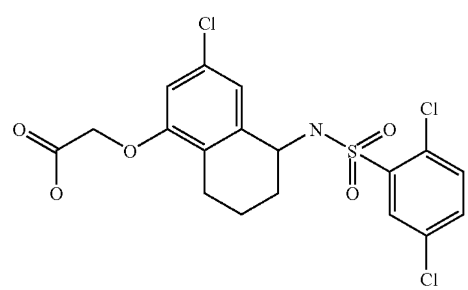 |
| 1-14 | [3-Chloro-5-(2,4-dichloro-2-fluoro-5,6,7,8-tetrahydro-naphthalen-1-yloxy]-acetic acid | 13.03 (br. s, 1H), 8.62 (d, J = 9.0 Hz, 1H), 8.05 (d, J = 8.4 Hz, 1H), 7.93 (d, J = 2.2 Hz, 1H), 7.67 (dd, J = 8.4, 2.2 Hz, 1H), 6.91 (d, J = 6.6 Hz, 1H), 4.69 (s, 2H), 4.24-4.38 (m, 1H), 2.63 (br. s, 2H), 1.83 (br. s, 1H), 1.52-1.75 (m, 3H) | 480 | 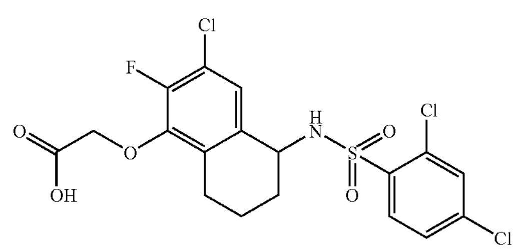 |
| 1-15 | [5-(3-Bromo-5-trifluoromethyl-benzenesulfonyl-amino)-3-chloro-2-fluoro-5,6,7,8-tetrahydro-naphthalen-1-yloxy]-acetic acid | 13.09 (br. s, 1H), 8.53 (d, J = 8.3 Hz, 1H), 8.38 (s, 1H), 8.31 (s, 1H), 8.14 (s, 1H), 6.67 (d, J = 6.8 Hz, 1H), 4.68 (s, 2H), 4.44-4.52 (m, 1H), 2.57-2.72 (m, 2H), 1.70-1.80 (m, 1H), 1.59 (br. s, 3H) | 560/562 | 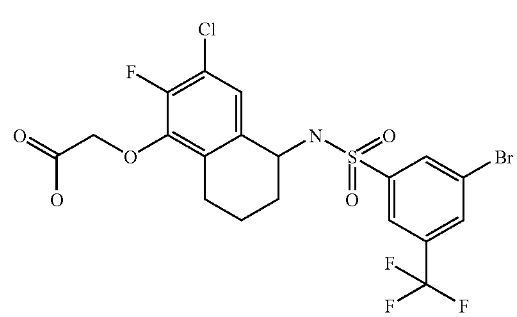 |

-continued

| Example No. | Systematic Name | ¹H NMR (400 MHz, DMSO-d$_6$) δ ppm | MS (M−+0H)⁻ | Structure |
|---|---|---|---|---|
| 1-16 | [3-Chloro-5-(3-fluoro-5-trifluoromethyl-benzenesulfonyl-amino)-5,6,7,8-tetrahydro-naphthalen-1-yloxy]-acetic acid | 13.05 (br. s, 1H), 8.54 (d, J = 8.1 Hz, 1H), 8.13 (d, J = 9.0 Hz, 1H), 8.05 (d, J = 7.3 Hz, 1H), 8.02 (s, 1H), 6.80 (d, J = 1.4 Hz, 1H), 6.46 (d, J = 1.4 Hz, 1H), 4.74 (s, 2H), 4.44-4.52 (m, 1H), 2.54-2.60 (m, 1H), 2.42-2.48 (m, 1H), 1.70-1.84 (m, 1H), 1.47-1.70 (m, 3H) | 480/482 | 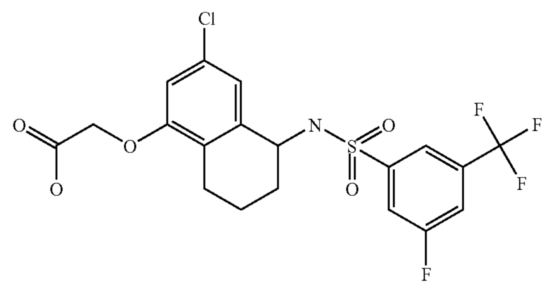 |
| 1-17 | [5-(3-Bromo-5-trifluoromethyl-benzenesulfonyl-amino)-3-chloro-5,6,7,8-tetrahydro-naphthalen-1-yloxy]-acetic acid | 13.05 (br. s, 1H), 8.54 (d, J = 8.6 Hz, 1H), 8.38 (s 1H), 8.32 (s 1H), 8.15 (s, 1H), 6.80 (d, J = 1.6 Hz, 1H), 6.43 (d, J = 1.6 Hz, 1H), 4.74 (s, 2H), 4.41-4.53 (m, 1H), 2.53-2.60 (m, 1H), 2.40-2.49 (m, 1H), 1.75 (br. s, 1H), 1.54-1.71 (m, 3H) | 540/542 | 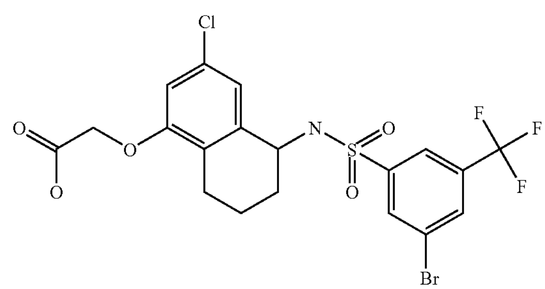 |
| 1-18 | [(R)-3-Chloro-5-(2,4-dichloro-benzenesulfonyl-amino)-5,6,7,8-tetrahydro-naphthalen-1-yloxy]-acetic acid | 8.61 (br. s, 1H), 8.06 (d, J = 8.5 Hz, 1H), 7.93 (d, J = 2.0 Hz, 1H), 7.67 (dd, J = 8.5, 2.0 Hz, 1H), 6.75 (s, 1H), 6.67 (s, 1H), 4.64 (s, 2H), 4.31 (br. s, 1H), 2.45-2.50 (m, 2H), 1.75-1.93 (m, 1H), 1.51-1.66 (m, 3H) | 462 | 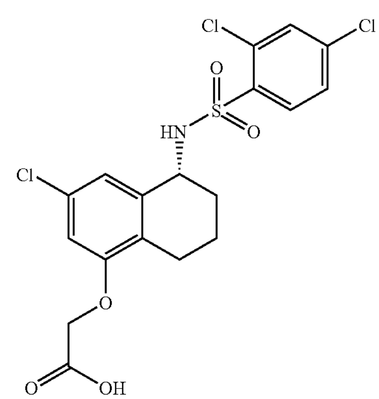 |
| 1-19 | [5-(3,5-Bis-trifluoromethyl-benzenesulfonyl-amino)-3-bromo-5,6,7,8-tetrahydro-naphthalen-1-yloxy]-acetic acid | (300 MHz, DMSO-d$_6$) 13.07 (br. s, 1H), 8.63 (d, J = 8.2 Hz, 1H), 8.54 (s, 1H), 8.46 (s, 2H), 6.89 (s, 1H), 6.49 (s, 1H), 4.73 (s, 2H), 4.46-4.60 (m, 1H), 2.33-2.47 (m, 2H), 1.52-1.82 (m, 4H) | 597# | 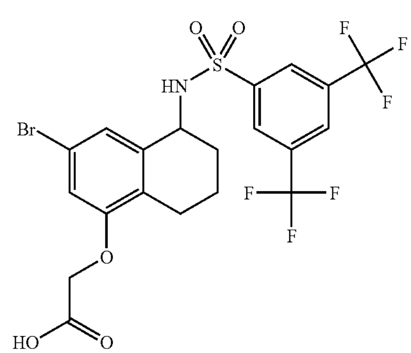 |

-continued

| Example No. | Systematic Name | ¹H NMR (400 MHz, DMSO-d₆) δ ppm | MS (M −+0H)⁻ | Structure |
|---|---|---|---|---|
| 1-20 | [(R)-5-(3,5-Bis-trifluoromethyl-benzenesulfonyl-amino)-3-bromo-5,6,7,8-tetrahydro-naphthalen-1-yloxy]-acetic acid | (300 MHz, DMSO-d₆) 13.07 (br. s, 1H), 8.63 (d, J = 8.2 Hz, 1H), 8.54 (s, 1H), 8.46 (s, 2H), 6.89 (s, 1H), 6.49 (s, 1H), 4.73 (s, 2H), 4.46-4.60 (m, 1H), 2.33-2.47 (m, 2H), 1.52-1.82 (m, 4H) | 597# | 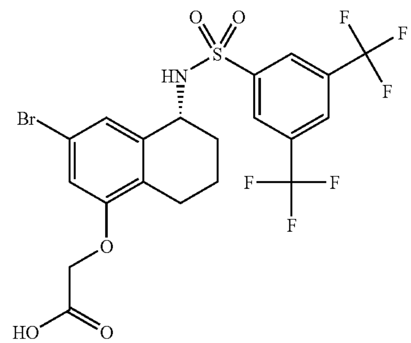 |
| 1-21 | [3-Chloro-2-fluoro-5-(3-fluoro-5-trifluoromethyl-benzenesulfonyl-amino)-5,6,7,8-tetrahydro-naphthalen-1-yloxy]-acetic acid | 13.36 (br. s, 1H), 8.52 (d, J = 8.3 Hz, 1H), 8.13 (d, J = 8.8 Hz, 1H), 8.04 (d, J = 7.8 Hz, 1H), 8.01 (s, 1H), 6.70 (d, J = 6.8 Hz, 1H), 4.68 (s, 2H), 4.41-4.53 (m, 1H), 2.57-2.73 (m, 2H), 1.69-1.82 (m, 1H), 1.54-1.69 (m, 3H) | 498/500 | 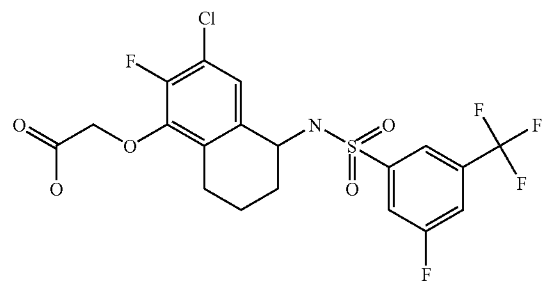 |
| 1-22 | [5-(3,5-Bis-trifluoromethyl-benzenesulfonyl-amino)-2-fluoro-5,6,7,8-tetrahydro-naphthalen-1-yloxy]-acetic acid | 12.92 (br. s, 1H), 8.53 (d, J = 7.8 Hz, 1H), 8.51 (s, 1H), 8.45 (s, 2H), 7.00 (dd, J = 11.7, 8.7 Hz, 1H), 6.76 (dd, J = 8.7, 5.1 Hz, 1H), 4.62 (s, 2H), 4.47-4.57 (m, 1H), 2.56-2.81 (m, 2H), 1.66-1.83 (m, 1H), 1.48-1.66 (m, 3H) | 537# | 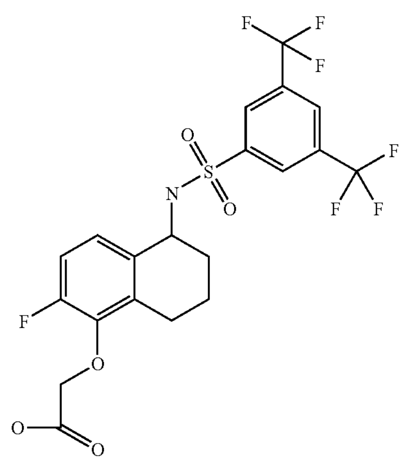 |
| 1-23* | [(R)-5-(3,5-Bis-trifluoromethyl-benzenesulfonyl-amino)-3-methoxy-5,6,7,8-tetrahydro-naphthalen-1-yloxy]-acetic acid | 14.31 (br. s, 1H), 8.50-8.56 (m, 2H), 8.48 (s, 2H), 6.25 (d, J = 1.8 Hz, 1H), 5.92 (d, J = 1.8 Hz, 1H), 4.55 (br. s, 2H), 4.44-4.52 (m, 1H), 3.45 (s, 3H), 2.80 (br. s, 1H), 2.36-2.46 (m, 1H), 1.68-1.82 (m, 1H), 1.62 (br. s, 3H) | 526 | 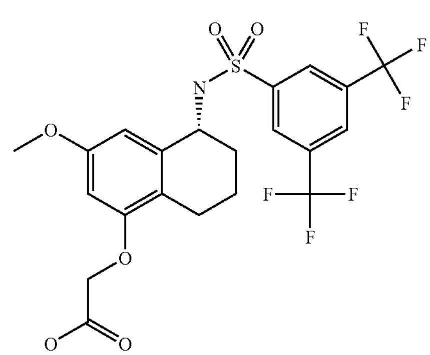 |

-continued

| Example No. | Systematic Name | ¹H NMR (400 MHz, DMSO-$d_6$) δ ppm | MS (M−+0H)⁻ | Structure |
|---|---|---|---|---|
| 1-24 | [5-(3,5-Bis-trifluoromethyl-benzenesulfonyl-amino)-3-phenyl-5,6,7,8-tetrahydro-naphthalen-1-yloxy]-acetic acid | (300 MHz, DMSO-$d_6$) 12.99 (br. s, 1H), 8.62 (d, J = 7.5 Hz, 1H), 8.47 (s, 3H), 7.28-7.48 (m, 3H), 7.24 (d, J = 7.5 Hz, 2H), 6.92 (s, 1H), 6.4 (s, 1H), 4.79 (s, 2H), 4.64 (br. s, 1H), 2.63-2.76 (m, 1H), 2.5-2.57 (m, 1 H), 1.74 (br. s, 4H) | 596# | 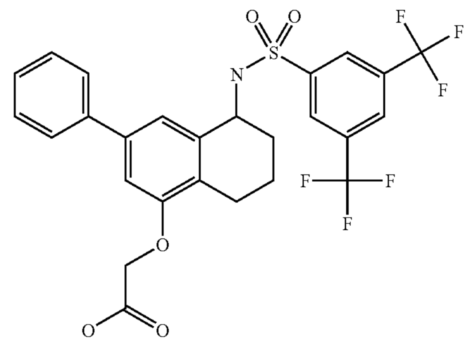 |
| 1-25 | [(R)-5-(3,5-Bis-trifluoromethyl-benzenesulfonyl-amino)-2-chloro-5,6,7,8-tetrahydro-naphthalen-1-yloxy]-acetic acid | N/A | 530 | 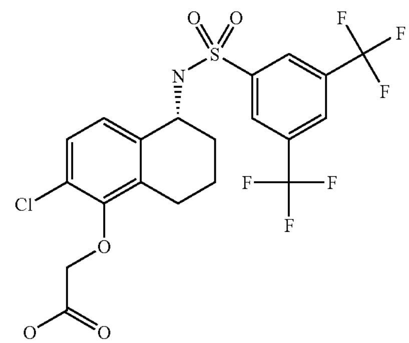 |
| 1-26 | [2,3-Difluoro-5-(3-fluoro-5-trifluoromethyl-benzenesulfonyl-amino)-5,6,7,8-tetrahydro-naphthalen-1-yloxy]-acetic acid | 12.91 (br. s, 1H), 8.52 (d, J = 8.3 Hz, 1H), 8.12 (d, J = 7.8 Hz, 1H), 8.04 (d, J =]7.8 Hz, 1H), 8.01 (s, 1H), 6.64 (dd, J =11.2, 7.8 Hz, 1H), 4.71 (d, J = 2.0 Hz, 2H), 4.33-4.56 (m, 1H), 2.53-2.72 (m, 2H), 1.67-1.82 (m, 1H), 1.47-1.67 (m, 3H) | 506# | 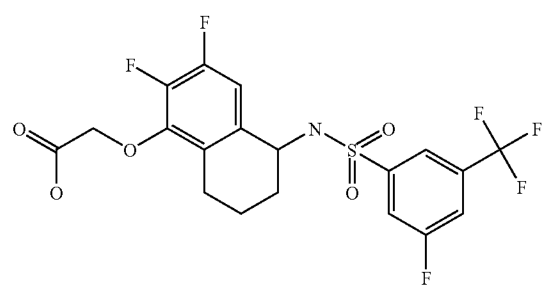 |
| 1-27 | [3-Fluoro-5-(3-fluoro-5-trifluoromethyl-benzenesulfonyl-amino)-5,6,7,8-tetrahydro-naphthalen-1-yloxy]-acetic acid | 12.69 (br. s, 1H), 8.52 (d, J = 8.3 Hz, 1H), 8.12 (d, J = 8.3 Hz, 1H), 8.00-8.08 (m, 2H), 6.66 (d, J = 10.3 Hz, 1H), 6.31 (d, J =8.8 Hz, 1H), 4.70 (s, 2H), 4.39-4.51 (m, 1H), 2.51-2.58 (m, 2H), 1.75 (br. s, 1H), 1.47-1.69 (m, 3H) | 488# | 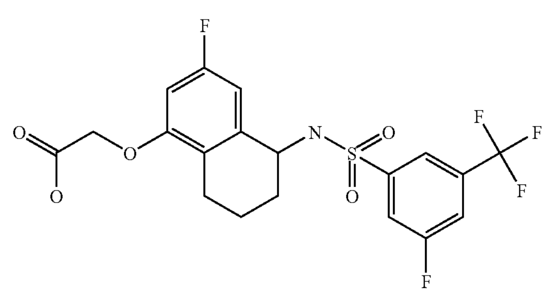 |
| 1-28 | [5-(3-Bromo-5-trifluoromethyl-benzenesulfonyl-amino)-3-fluoro-5,6,7,8-tetrahydro-naphthalen-1-yloxy]-acetic acid | 13.02 (br. s, 1H), 8.52 (d, J =8.3 Hz, 1H), 8.37 (s, 1H), 8.32 (s, 1H), 8.16 (s, 1H), 6.66 (d, J = 11.2 Hz, 1H), 6.30 (d, J = 8.8 Hz, 1H), 4.71 (s, 2H), 4.39-4.52 (m, 1H), 2.41-2.48 (m, 2H), 1.75 (br. s, 1H), 1.58 (br. s, 3 H) | 548# | 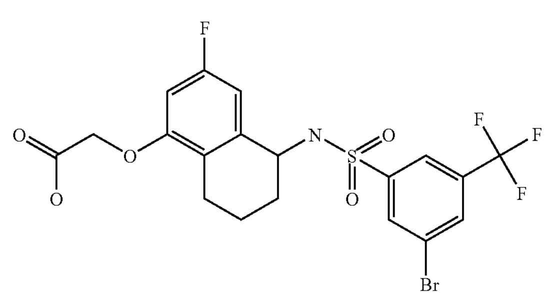 |

-continued

| Example No. | Systematic Name | $^1$H NMR (400 MHz, DMSO-$d_6$) δ ppm | MS (M−+0H)$^-$ | Structure |
|---|---|---|---|---|
| 1-29 | [5-(3-Bromo-5-trifluoromethyl-benzenesulfonyl-amino)-2,3-difluoro-5,6,7,8-tetrahydro-naphthalen-1-yloxy]-acetic acid | 13.06 (br. s, 1H), 8.52 (d, J = 7.8 Hz, 1H), 8.38 (s, 1H), 8.31 (s, 1H), 8.15 (s, 1H), 6.63 (dd, J = 11.2, 7.3 Hz, 1H), 4.72 (s, 2H), 4.29-4.51 (m, 1H), 2.55-2.65 (m, 2H), 1.69-1.82 (m, 1H), 1.49-1.69 (m, 3H) | 542 | 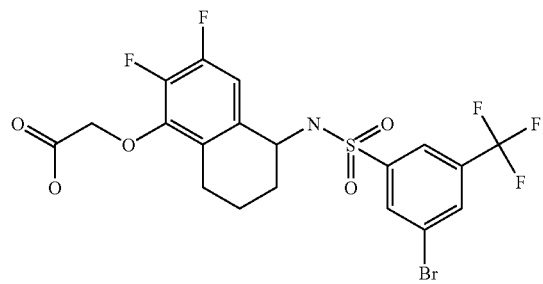 |
| 1-30 | [5-(2,4-Dichloro-benzenesulfonyl-amino)-2,3-difluoro-5,6,7,8-tetrahydro-naphthalen-1-yloxy]-acetic acid | 13.05 (br. s, 1H), 8.62 (d, J = 8.8 Hz, 1H), 8.05 (d, J = 8.5 Hz, 1H), 7.94 (d, J = 2.0 Hz, 1H), 7.66 (dd, J = 8.5, 2.0 Hz, 1H), 6.83 (dd, J = 11.5, 7.6 Hz, 1H), 4.72 (s, 2H), 4.19-4.35 (m, 1H), 2.60 (br. s, 2H), 1.83 (br. s, 1H), 1.50-1.67 (m, 3H) | 464 | 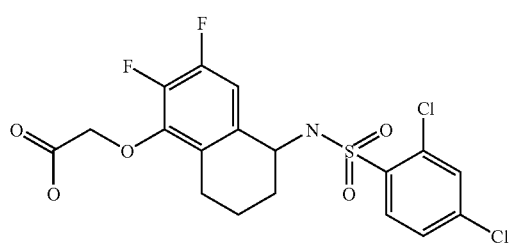 |
| 1-31 | [5-(2,4-Dichloro-benzenesulfonyl-amino)-3-fluoro-5,6,7,8-tetrahydro-naphthalen-1-yloxy]-acetic acid | 13.05 (br. s, 1H), 8.60 (d, J = 9.3 Hz, 1H), 8.06 (d, J = 8.3 Hz, 1H), 7.93 (d, J = 2.0 Hz, 1H), 7.66 (dd, J = 8.3, 2.0 Hz, 1H), 6.67 (dd, J = 11.0, 2.2 Hz, 1H), 6.53 (dd, J = 10.0, 2.2 Hz, 1H), 4.72 (s, 2H), 4.25-4.37 (m, 1H), 2.50 (s, 2H), 1.74-1.92 (m, 1H), 1.49-1.71 (m, 3H) | 446 | 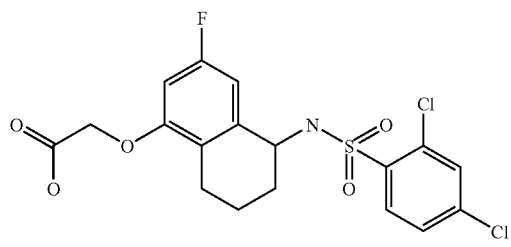 |
| 1-32 | [5-(2,5-Dichloro-benzenesulfonyl-amino)-2,3-difluoro-5,6,7,8-tetrahydro-naphthalen-1-yloxy]-acetic acid | 13.04 (br. s, 1H), 8.69 (d, J = 9.3 Hz, 1H), 8.01 (s, 1H), 7.73-7.83 (m, 2H), 6.80 (dd, J = 11.2, 7.3 Hz, 1H), 4.72 (s, 2H), 4.28-4.42 (m, 1H), 2.60 (br. s, 2H), 1.75-1.89 (m, 1H), 1.49-1.71 (m, 3H) | 464 | 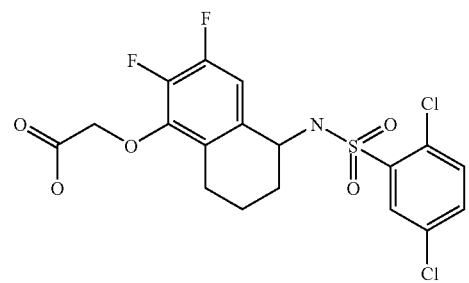 |
| 1-33 | [5-(2,5-Dichloro-benzenesulfonyl-amino)-3-fluoro-5,6,7,8-tetrahydro-naphthalen-1-yloxy]-acetic acid | 13.03 (br. s, 1H), 8.67 (d, J = 8.8 Hz, 1H), 8.02 (s, 1H), 7.77 (br. s, 2H), 6.67 (d, J = 10.8 Hz, 1H), 6.51 (d, J = 9.8 Hz, 1H), 4.71 (s, 2H), 4.26-4.44 (m, 1H), 2.50 (br. s, 2H), 1.85 (br. s, 1H), 1.63 (br. s, 3H) | 470$^#$ | 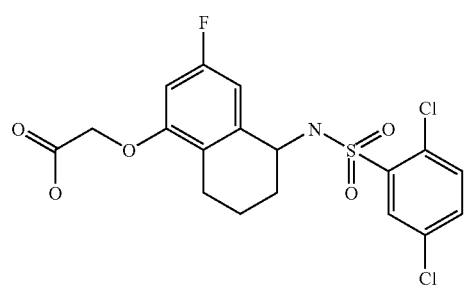 |

| Example No. | Systematic Name | ¹H NMR (400 MHz, DMSO-d₆) δ ppm | MS (M−+0H)⁻ | Structure |
|---|---|---|---|---|
| 1-34 | {2,3-Difluoro-5-[5-(3-isopropyl-phenyl)-pyridine-2-sulfonylamino]-5,6,7,8-tetrahydro-naphthalen-1-yloxy}-acetic acid | 12.82 (br. s, 1H), 9.10 (s, 1H), 8.45 (d, J = 8.3 Hz, 1H), 8.39 (dd, J = 8.2, 1.7 Hz, 1H), 8.06 (d, J = 8.2 Hz, 1H), 7.70 (s, 1H), 7.64 (d, J = 7.3 Hz, 1H), 7.48 (t, J = 7.3 Hz, 1H), 7.39 (d, J = 7.3 Hz, 1H), 6.91 (dd, J = 12.0, 7.6 Hz, 1H), 4.71 (s, 2H), 4.34-4.61 (m, 1H), 2.85-3.10 (m, 1H), 2.57-2.66 (m, 2H), 1.62 (br. s, 4H), 1.28 (d, J = 6.8 Hz, 6H) | 517## | 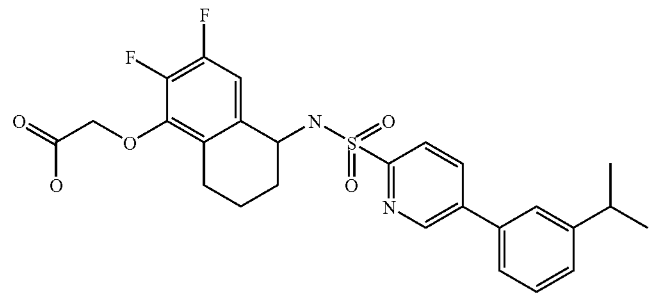 |
| 1-35 | {3-Fluoro-5-[5-(3-isopropyl-phenyl)-pyridine-2-sulfonylamino]-5,6,7,8-tetrahydro-naphthalen-1-yloxy}-acetic acid | 13.04 (br. s, 1H), 9.10 (d, J = 2.0 Hz, 1H), 8.42 (d, J = 8.8 Hz, 1H), 8.38 (dd, J = 8.0, 2.0 Hz, 1H), 8.06 (d, J = 8.0 Hz, 1H), 7.70 (s, 1H), 7.64 (d, J = 7.8 Hz, 1H), 7.48 (t, J = 7.8 Hz, 1H), 7.39 (d, J = 7.8 Hz, 1H), 6.65 (dd, J = 11.2, 2.0 Hz, 1H), 6.61 (d, J = 10.3 Hz, 1H), 4.71 (s, 2H), 4.44-4.55 (m, 1H), 2.91-3.07 (m, 1H), 2.50 (br. s, 2H), 1.53-1.90 (m, 4H), 1.28 (d, J = 7.3 Hz, 6H) | 499## | 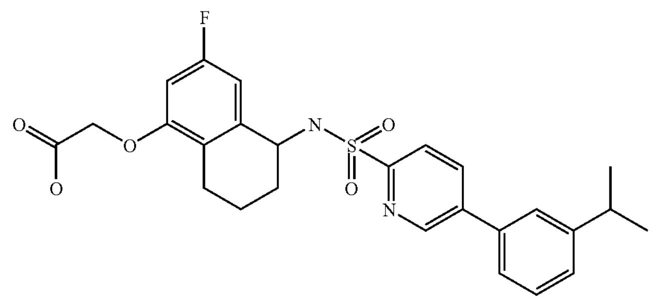 |
| 1-36 | {3-Chloro-5-[5-(3-isopropyl-phenyl)-pyridine-2-sulfonylamino]-5,6,7,8-tetrahydro-naphthalen-1-yloxy}-acetic acid | 13.04 (br. s, 1H), 9.09 (s, 1H), 8.45 (d, J = 8.8 Hz, 1H), 8.38 (d, J = 7.8 Hz, 1H), 8.06 (d, J = 7.8 Hz, 1H), 7.69 (s, 1H), 7.64 (d, J = 7.3 Hz, 1H), 7.48 (t, J = 7.3 Hz, 1H), 7.38 (d, J = 7.3 Hz, 1H), 6.75 (br. s, 1H), 6.73 (s, 1H), 4.67 (br. s, 2H), 4.49 (br. s, 1H), 2.88-3.09 (m, 1H), 2.51-2.65 (m, 2H), 1.54-1.90 (m, 4H), 1.27 (d, J = 6.8 Hz, 6H) | 515## | 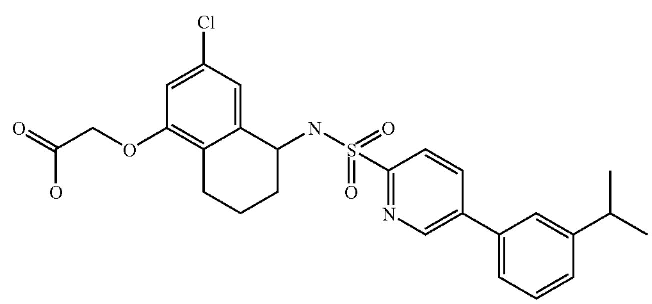 |
| 1-37 | [(R)-3-Bromo-5-(3-bromo-5-trifluoromethyl-benzenesulfonyl-amino)-5,6,7,8-tetrahydro-naphthalen-1-yloxy]-acetic acid | 13.14 (br. s, 1H), 8.61 (d, J = 8.5 Hz, 1H), 8.44 (s, 1H), 8.38 (s, 1H), 8.21 (s, 1H), 6.97 (s, 1H), 6.61 (s, 1H), 4.80 (s, 2H), 4.47-4.64 (m, 1H), 2.58-2.76 (m, 2H), 1.56-1.91 (m, 4H) | 583 | 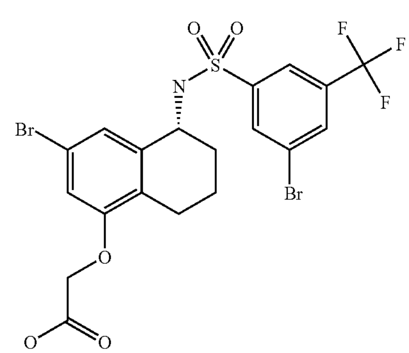 |

| Example No. | Systematic Name | ¹H NMR (400 MHz, DMSO-d₆) δ ppm | MS (M−+0H)⁻ | Structure |
|---|---|---|---|---|
| 1-38 | [(R)-3-Chloro-2-fluoro-5-(3-fluoro-5-trifluoromethyl-benzenesulfonyl-amino)-5,6,7,8-tetrahydro-naphthalen-1-yloxy]-acetic acid | 13.01 (br. s, 1H), 8.54 (d, J = 7.7 Hz, 1H), 8.13 (d, J = 8.1 Hz, 1H), 8.04 (d, J = 8.0 Hz, 1H), 8.01 (s, 1H), 6.69 (d, J = 6.8 Hz, 1H), 4.67 (s, 2H), 4.42-4.52 (m, 1H), 2.57-2.77 (m, 2H), 1.68-1.85 (m, 1H), 1.49-1.70 (m, 3H) | 498 | 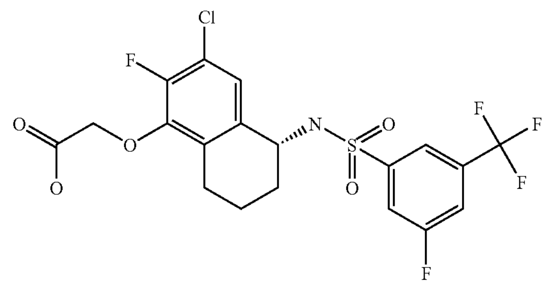 |
| 1-39 | [(R)-5-(3-Bromo-5-trifluoromethyl-benzenesulfonyl-amino)-3-chloro-2-fluoro-5,6,7,8-tetrahydro-naphthalen-1-yloxy]-acetic acid | 12.96 (br. s, 1H), 8.53 (d, J = 6.2 Hz, 1H), 8.38 (s, 1H), 8.31 (s, 1H), 8.14 (s, 1H), 6.66 (d, J = 6.8 Hz, 1H), 4.66 (s, 2H), 4.40-4.54 (m, 1H), 2.56-2.75 (m, 2H), 1.71-1.85 (m, 1H), 1.51-1.70 (m, 3H) | 558 | 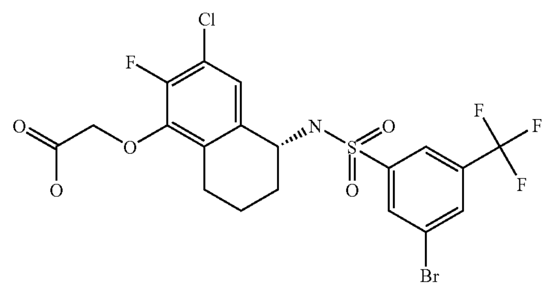 |
| 1-40 | [(R)-3-Chloro-5-(2,4-dichloro-benzenesulfonyl-amino)-2-fluoro-5,6,7,8-tetrahydro-naphthalen-1-yloxy]-acetic acid | 13.08 (br. s, 1H), 8.63 (d, J = 9.0 Hz, 1H), 8.05 (d, J = 8.5 Hz, 1H), 7.93 (d, J = 2.0 Hz, 1H), 7.67 (dd, J = 8.5, 2.0 Hz, 1H), 6.90 (d, J = 6.8 Hz, 1H), 4.68 (s, 2H), 4.21-4.41 (m, 1H), 2.59-2.70 (m, 2H), 1.84 (br. s, 1H), 1.48-1.69 (m, 3H) | 480 | 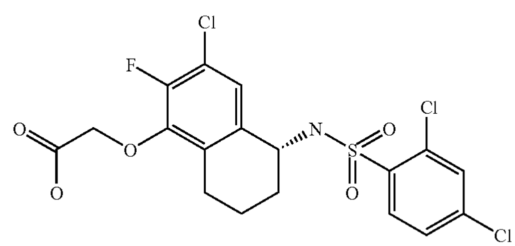 |
| 1-41 | [(R)-3-Chloro-5-(3-fluoro-5-trifluoromethyl-benzenesulfonyl-amino)-5,6,7,8-tetrahydro-naphthalen-1-yloxy]-acetic acid | 13.34 (br. s, 1H), 8.55 (d, J = 8.2 Hz, 1H), 8.13 (d, J = 8.2 Hz, 1H), 8.05 (d, J = 7.7 Hz, 1H), 8.02 (s, 1H), 6.79 (d, J = 1.3 Hz, 1H), 6.46 (s, 1H), 4.72 (s, 2H), 4.43-4.52 (m, 1H), 2.39-2.51 (m, 2H), 1.75 (br. s, 1H), 1.48-1.70 (m, 3H) | 480 | 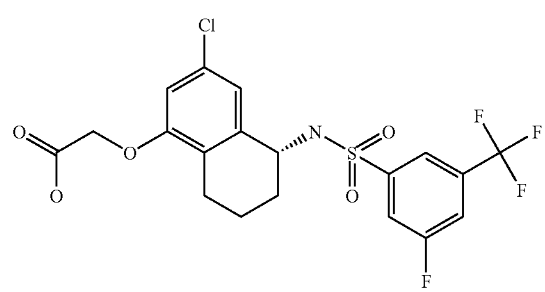 |
| 1-42 | [(R)-5-(3-Bromo-5-trifluoromethyl-benzenesulfonyl-amino)-3-chloro-5,6,7,8-tetrahydro-naphthalen-1-yloxy]-acetic acid | 12.97 (br. s, 1H), 8.54 (d, J = 7.9 Hz, 1H), 8.38 (s, 1H), 8.32 (s, 1H), 8.15 (s, 1H), 6.79 (d, J = 1.3 Hz, 1H), 6.43 (d, J = 1.3 Hz, 1H), 4.71 (s, 2H), 4.42-4.53 (m, 1H), 2.40-2.50 (m, 2H), 1.69-1.83 (m, 1H), 1.49-1.72 (m, 3H) | 540 | 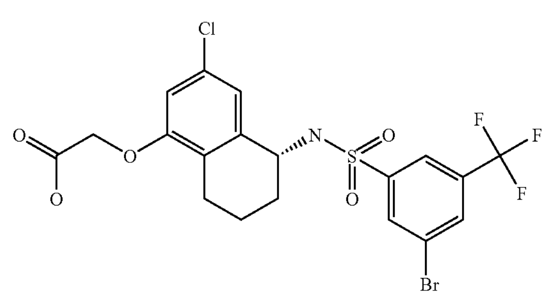 |

| Example No. | Systematic Name | ¹H NMR (400 MHz, DMSO-d₆) δ ppm | MS (M −+0H)⁻ | Structure |
|---|---|---|---|---|
| 1-43 | [(R)-3-Chloro-5-(2,5-dichloro-benzenesulfonyl-amino)-5,6,7,8-tetrahydro-naphthalen-1-yloxy]-acetic acid | 13.14 (br. s, 1H), 8.70 (d, J = 9.0 Hz, 1H), 8.03 (d, J = 2.2 Hz, 1H), 7.79 (dd, J = 8.5, 2.2 Hz, 1H), 7.76 (d, J = 8.5 Hz, 1H), 6.79 (d, J = 1.5 Hz, 1H), 6.72 (d, J = 1.5 Hz, 1H), 4.72 (s, 2H), 4.38 (br. s, 1H), 2.46-2.49 (m, 2H), 1.76-1.96 (m, 1H), 1.50-1.74 (m, 3H) | 462 | 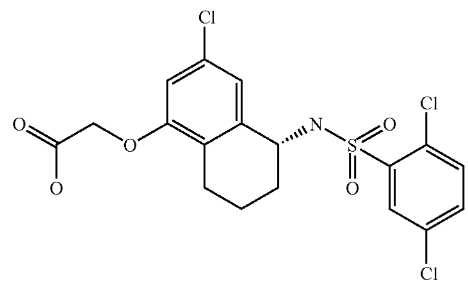 |
| 1-44 | {3-Chloro-2-fluoro-5-[5-(3-isopropyl-phenyl)-pyridine-2-sulfonylamino]-5,6,7,8-tetrahydro-naphthalen-1-yloxy}-acetic acid | 13.07 (br. s, 1H), 9.09 (d, J = 1.22 Hz, 1H), 8.48 (d, J =8.56 Hz, 1H), 8.39 (dd, J = 8.07, 1.96 Hz, 1H), 8.06 (d, J = 8.31 Hz, 1H), 7.59-7.78 (m, 2H), 7.48 (t, J = 7.58 Hz, 1H), 7.39 (d, J = 7.58 Hz, 1H), 6.97 (d, J = 6.85 Hz, 4H), 4.67 (s, 2H), 4.49 (br d, J = 5.38 Hz, 1H) 3.01 (dt, J = 13.69, 6.85 Hz, 1H), 2.64 (br. s, 1H), 1.54-1.85 (m, 5H), 1.27 (d, J = 6.85 Hz, 6H) | 533## | 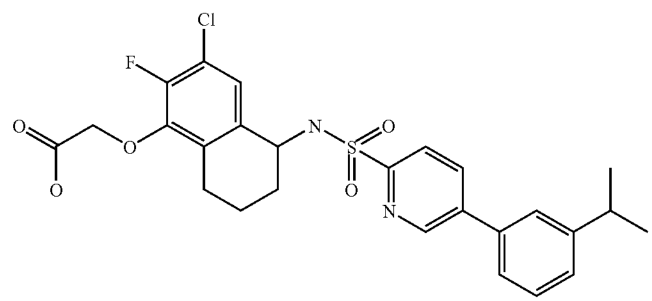 |
| 1-45 | [5-(2,5-Dichloro-benzenesulfonyl-amino)-2-fluoro-5,6,7,8-tetrahydro-naphthalen-1-yloxy]-acetic acid | 12.93 (br. s, 1H), 8.60 (d, J = 9.0 Hz, 1H), 8.00 (d, J = 1.8 Hz, 1H), 7.77 (dd, J = 8.5, 1.8 Hz, 1H), 7.74 (d, J = 8.5 Hz, 1H), 7.06 (dd, J = 11.6, 8.7 Hz, 1H), 6.91 (dd, J = 8.7, 5.1 Hz, 1H), 4.61 (s, 2H), 4.32-4.44 (m, 1H), 2.67 (br. s, 2H), 1.75-1.88 (m, 1H), 1.53-1.66 (m, 3H) | 470# | 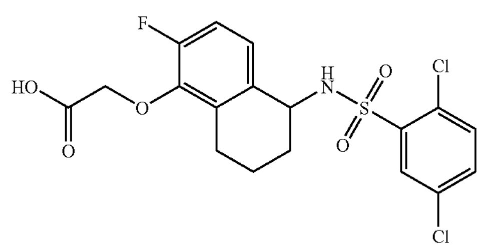 |
| 1-46 | [5-(2,4-Dichloro-benzenesulfonyl-amino)-2-fluoro-5,6,7,8-tetrahydro-naphthalen-1-yloxy]-acetic acid | 12.94 (br. s, 1H), 8.52 (d, J = 9.0 Hz, 1H), 8.05 (d, J = 8.5 Hz, 1H), 7.91 (d, J = 2.1 Hz, 1H), 7.65 (dd, J = 8.5, 2.1 Hz, 1H), 7.07 (dd, J = 11.7, 8.8 Hz, 1H), 6.94 (dd, J = 8.8, 5.0 Hz, 1H), 4.61 (s, 2H), 4.22-4.39 (m, 1H), 2.62-2.74 (m, 2H), 1.83 (br. s, 1H), 1.58 (br. s, 3H) | 470# | 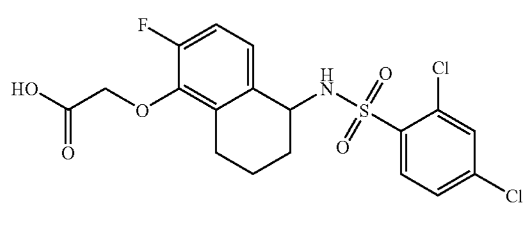 |

-continued

| Example No. | Systematic Name | $^1$H NMR (400 MHz, DMSO-d$_6$) δ ppm | MS (M −+0H)$^−$ | Structure |
|---|---|---|---|---|
| 1-47 | {2-Fluoro-5-[5-(3-isopropyl-phenyl)-pyridine-2-sulfonylamino]-5,6,7,8-tetrahydro-naphthalen-1-yloxy}-acetic acid | 12.94 (br. s, 1H), 9.09 (d, J = 1.71 Hz, 1H), 8.29-8.44 (m, 2H), 8.04 (d, J = 8.31 Hz, 1H), 7.71 (s, 1H), 7.65 (d, J = 7.58 Hz, 1H), 7.48 (t, J = 7.58 Hz, 1H), 7.33-7.42 (m, 1H), 7.05 (d, J = 8.80 Hz, 2H), 4.62 (s, 2H), 4.50-4.55 (m, 1H), 3.01 (dt, J = 13.75, 6.94 Hz, 2H), 2.61-2.76 (m, 1H), 1.57-1.85 (m, 4H), 1.28 (d, J = 6.85 Hz, 6H) | 499## | 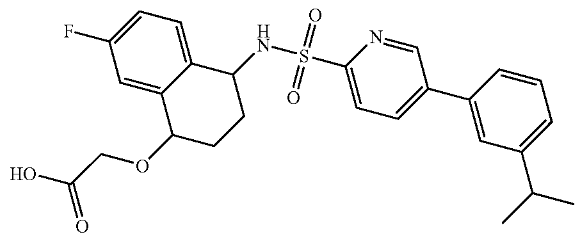 |
| 1-48 | [(R)-3-Bromo-5-(2,5-dichloro-benzenesulfonyl-amino)-5,6,7,8-tetrahydro-naphthalen-1-yloxy]-acetic acid | (300 MHz, DMSO-d$_6$) 8.69 (br. s, 1H), 8.00 (d, J = 2.1 Hz, 1H), 7.77 (dd, J = 8.8, 2.1 Hz, 1H), 7.73 (d, J = 8.8 Hz, 1H), 6.74 (br. s, 1H), 6.73 (br. s, 1H), 4.38 (s, 2H), 4.29-4.36 (m, 1H), 2.36-2.48 (m, 2H), 1.70-1.93 (m, 1H), 1.46-1.70 (m, 3H). | 505 | 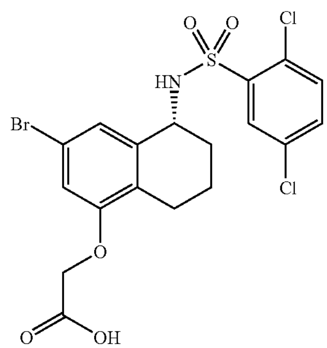 |
| 1-49 | [(R)-3-Bromo-5-(2,5-dichloro-benzenesulfonyl-amino)-5,6,7,8-tetrahydro-naphthalen-1-yloxy]-acetic acid | 13.00 (br. s, 1H), 8.61 (d, J = 9.1 Hz, 1H), 8.04 (d, J = 8.8 Hz, 1H), 7.9 (s, 1H), 7.65 (d, J = 8.5 Hz, 1H), 6.86 (s, 1H), 6.76 (s, 1H), 4.67 (s, 2H), 4.28 (br. s, 1H), 2.45 (br. s, 2H), 1.83 (br. s, 1H), 1.58 (br. s, 3H) | 505 | 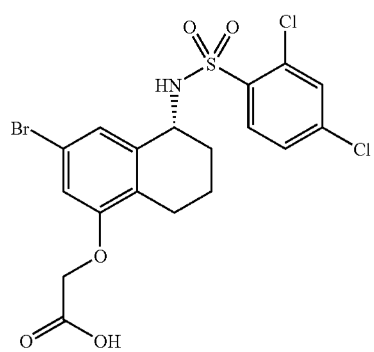 |
| 1-50 | [5-(3,5-Bis-methanesulfonyl-benzenesulfonyl-amino)-3-bromo-5,6,7,8-tetrahydro-naphthalen-1-yloxy]-acetic acid | 13.18 (br. s, 1H), 8.65-8.85 (m, 4H), 6.96 (br. s, 1H), 6.76 (s, 1H), 4.79 (br. s, 2H), 4.57-4.70 (m, 1H), 3.51 (s, 6H), 2.50-2.55 (m, 2H), 1.54-1.91 (m, 4H) | 593 | 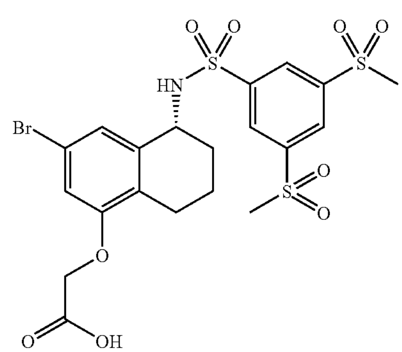 |

| Example No. | Systematic Name | $^1$H NMR (400 MHz, DMSO-d$_6$) δ ppm | MS (M −+OH)$^-$ | Structure |
|---|---|---|---|---|
| 1-51 | [(R)-3-Bromo-5-(3-methoxy-5-trifluoromethyl-benzenesulfonyl-amino)-5,6,7,8-tetrahydro-naphthalen-1-yloxy]-acetic acid | (300 MHz, CDCl$_3$) 7.74 (s, 1H), 7.59 (s, 1H), 7.35 (s, 1H), 6.67 (d, J = 1.8 Hz, 2H), 5.38 (d, J = 8.5 Hz, 1H), 4.61 (s, 2H), 4.30-4.50 (m, 1H), 3.91 (s, 3H), 2.42-2.77 (m, 2H), 1.76 (br. s, 4H) | 560$^\#$ | 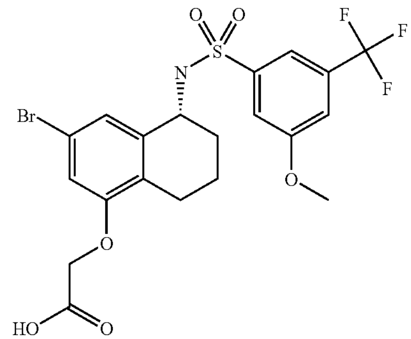 |
| 1-52 | [(R)-3-Bromo-5-(3-fluoro-5-trifluoromethyl-benzenesulfonyl-amino)-5,6,7,8-tetrahydro-naphthalen-1-yloxy]-acetic acid | (300 MHz) 13.04 (br. s, 1H), 8.55 (d, J = 8.2 Hz, 1H), 8.13 (d, J = 8.2 Hz, 1H), 8.05 (d, J = 7.8 Hz, 1H), 8.02 (s, 1H), 6.90 (s, 1H), 6.57 (s, 1H), 4.74 (s, 2H), 4.39-4.56 (m, 1H), 2.38-2.48 (m, 2H), 1.70-1.86 (m, 1H), 1.47-1.70 (m, 3H) | 524 | 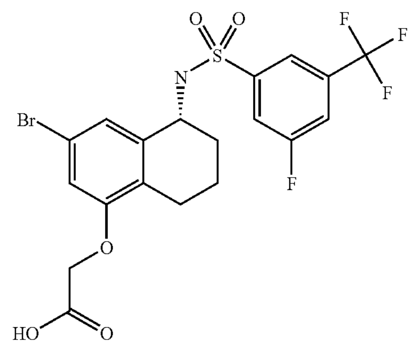 |

$^\#$(M + Na)$^+$
$^{\#\#}$(M ++0H)$^+$
*Resolved using chiral chromatography using Thar Technologies, Inc.'s Multigram ® III instrument, Daicel ® OD column 3 × 25 cm, 25% methanol

Example 2-1

{5-[(3,5-Bis-trifluoromethyl-benzenesulfonyl)-methyl-amino]-3-chloro-2-fluoro-5,6,7,8-tetrahydro-naphthalen-1-yloxy}-acetic acid

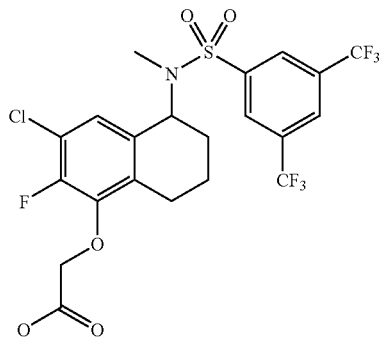

[5-(3,5-Bis-trifluoromethyl-benzenesulfonyl)-methyl-amino)-3-chloro-2-fluoro-5,6,7,8-tetrahydro-naphthalen-1-yloxy]-acetic acid tert-butyl ester

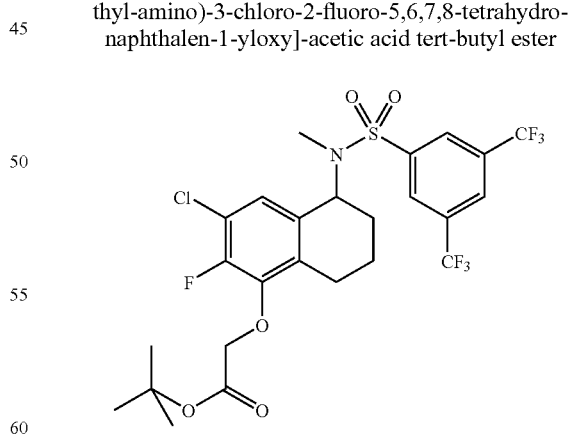

To a cooled solution of [5-(3,5-bis-trifluoromethyl-benzenesulfonylamino)-3-chloro-2-fluoro-5,6,7,8-tetrahydro-naphthalen-1-yloxy]-acetic acid tert-butyl ester (example 1-1, 9$^{th}$ step) (169.4 mg, 0.28 mmol) in N,N-dimethylformamide (2.5 mL) was added potassium carbonate (0.059 g, 0.42 mmol) and methyl iodide (0.02 mL, 0.31 mmol). The reaction mixture was stirred for 2 hours at room temperature and then extracted with ethyl acetate (15 mL×3). The collected organic layers were washed with water (15 mL×3), dried over anhydrous sodium sulfate, filtered, and concentrated under reduced pressure to give [5-(3,5-bis-trifluoromethyl-benzenesulfonyl)-methyl-amino)-3-chloro-2-fluoro-5,6,7,8-tetrahydro-naphthalen-1-yloxy]-acetic acid tert-butyl ester (156.0 mg, 90%), which was used in the next step without further purification.

{5-[(3,5-Bis-trifluoromethyl-benzenesulfonyl)-methyl-amino]-3-chloro-2-fluoro-5,6,7,8-tetrahydro-naphthalen-1-yloxy}-acetic acid

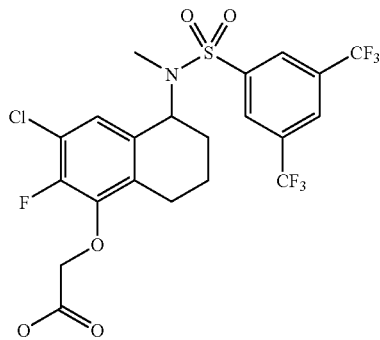

Starting with [5-(3,5-bis-trifluoromethyl-benzenesulfonyl)-methyl-amino)-3-chloro-2-fluoro-5,6,7,8-tetrahydro-naphthalen-1-yloxy]-acetic acid tert-butyl ester, using an analogous method to example 1-1, [5-(3,5-bis-trifluoromethyl-benzenesulfonyl)-methyl-amino)-3-chloro-2-fluoro-5,6,7,8-tetrahydro-naphthalen-1-yloxy]-acetic acid was obtained (69%). $^1$H NMR (400 MHz, DMSO-d$_6$) δ ppm 13.05 (br. s, 1H), 8.58 (s, 1H), 8.56 (s, 2H), 6.72 (d, J=6.8 Hz, 1H), 5.19-5.32 (m, 1H), 4.71 (d, J=1.7 Hz, 2H), 2.60 (s, 3H), 2.54-2.88 (m, 2H), 1.77-1.92 (m, 1H), 1.56-1.76 (m, 2H), 1.51 (m, 1H); MS cald. for $C_{21}H_{19}Cl_2F_6NO_5S$ 563, obsd. 562 (M−H$^+$).

Examples 2-2 to 2-33

The following examples 2-2 to 2-33 were prepared in an analogous manner to example 2-1. In cases where the example is depicted as a single enantiomer, a chiral separation of enantiomers was performed on the racemic final product, as described above.

| Example No. | Systematic Name | $^1$H NMR (400 MHz, DMSO-d$_6$) δ ppm | MS (M−+0H)$^-$ | Structure |
|---|---|---|---|---|
| 2-2 | {5-[(3,5-Bis-trifluoromethyl-benzenesulfonyl)-methyl-amino]-2-methyl-5,6,7,8-tetrahydro-naphthalen-1-yloxy}-acetic acid | 12.89 (br. s, 1H), 8.55 (s, 1H), 8.52 (s, 2H), 7.01 (d, J = 7.7 Hz, 1H), 6.75 (d, J = 7.7 Hz, 1H), 5.17-5.32 (m, 1H), 4.33 (s, 2H), 2.70-2.82 (m, 1H), 2.58-2.64 (m, 1H), 2.56 (s, 3H), 2.19 (s, 3H), 1.73-1.88 (m, 1H), 1.46-1.72 (m, 3H) | 524 | 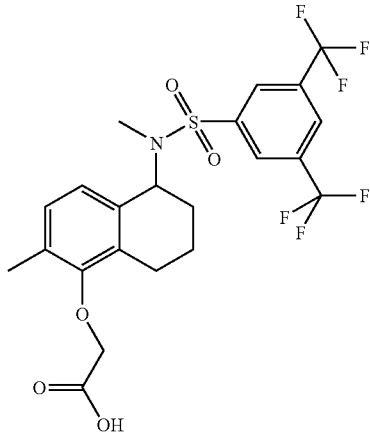 |

| Example No. | Systematic Name | $^1$H NMR (400 MHz, DMSO-d$_6$) δ ppm | MS (M −+0H)$^-$ | Structure |
|---|---|---|---|---|
| 2-3 | {5-[(3,5-Bis-trifluoromethyl-benzenesulfonyl)-methyl-amino]-2-ethyl-5,6,7,8-tetrahydro-naphthalen-1-yloxy}-acetic acid | 12.86 (br. s, 1H), 8.55 (s, 1H), 8.51 (s, 2H), 7.05 (d, J = 7.8 Hz, 1H), 6.80 (d, J = 7.8 Hz, 1H), 5.21-5.29 (m, 1H), 4.23-4.39 (m, 2H), 2.57 (s, 3H), 2.52-2.81 (m, 4H), 1.72-1.88 (m, 1H), 1.43-1.73 (m, 3H), 1.12 (t, J = 7.3 Hz, 3H) | 538 | 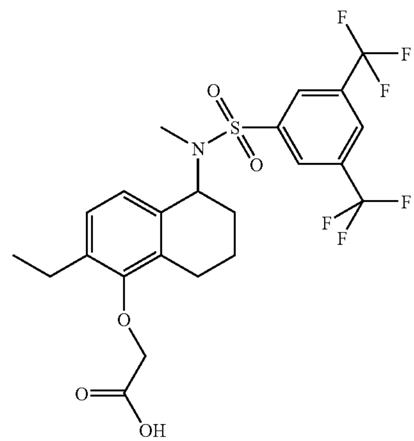 |
| 2-4 | {5-[(3,5-Bis-trifluoromethyl-benzenesulfonyl)-methyl-amino]-3-chloro-5,6,7,8-tetrahydro-naphthalen-1-yloxy}-acetic acid | 13.09 (br. s, 1H), 8.57 (s, 1H), 8.55 (s, 2H), 6.83 (d, J = 2.0 Hz, 1H), 6.49 (s, 1H), 5.24-5.32 (m, 1H), 4.74 (dd, J = 18.3, 16.4 Hz, 2H), 2.60 (s, 3H), 2.54-2.73 (m, 2H), 1.79-1.90 (m, 1H), 1.59-1.77 (m, 2H), 1.52 m, 1 H | 544 | 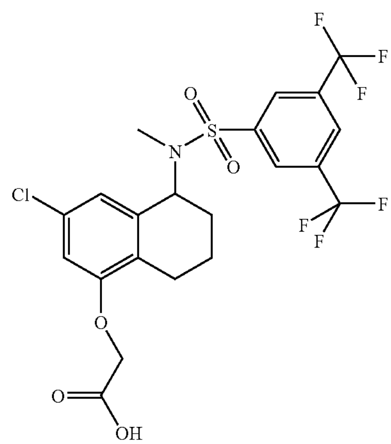 |
| 2-5 | {(R)-5-[(3,5-Bis-trifluoromethyl-benzenesulfonyl)-methyl-amino]-3-chloro-5,6,7,8-tetrahydro-naphthalen-1-yloxy}-acetic acid | N/A | 544 | 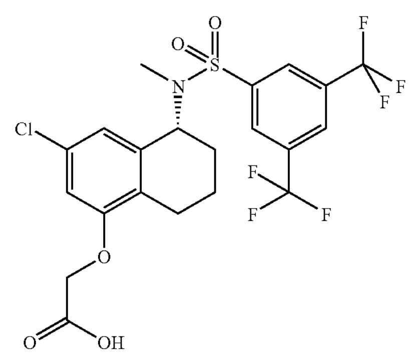 |
| 2-6 | {3-Chloro-5-[(2,4-dichloro-benzenesulfonyl)-methyl-amino]-5,6,7,8-tetrahydro-naphthalen-1-yloxy}-acetic acid | 12.33-13.99 (m, 1H), 8.10 (d, J = 8.5 Hz, 1H), 7.99 (d, J = 2.0 Hz, 1H), 7.68 (dd, J = 8.5, 2.0 Hz, 1H), 6.83 (s, 1H), 6.78 (s, 1H), 4.94 (dd, J = 10.5, 5.6 Hz, 1H), 4.72 (s, 2H), 2.66 - 2.76 (m, 1H), 2.64 (s, 3H), 2.54 (br. s, 1H), 2.28-2.44 (m, 1H), 1.54-1.97 (m, 3H) | 476/478 | 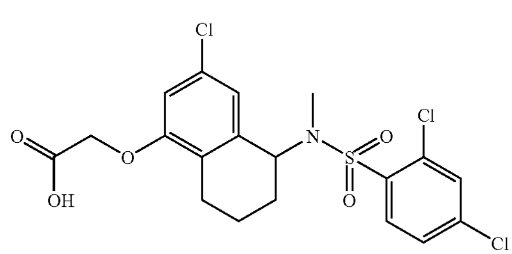 |

| Example No. | Systematic Name | $^1$H NMR (400 MHz, DMSO-d$_6$) δ ppm | MS (M −+0H)$^-$ | Structure |
|---|---|---|---|---|
| 2-7 | {5-[(3,5-Bis-trifluoromethyl-benzenesulfonyl)-methyl-amino]-2,3-dichloro-5,6,7,8-tetrahydro-naphthalen-1-yloxy}-acetic acid | 13.05 (br. s, 1H), 8.57 (s, 1H), 8.55 (s, 2H), 6.90 (s, 1H), 5.25-5.32 (m, 1 4.51 (s, 2H), 2.76-2.87 (m, 1H), 2.62 (s, 3H), 2.52-2.60 (m, 1H), 1.75-1.89 (m, 1H), 1.58-1.75 (m, 2H), 1.53 (br. s, 1H) | 578 | 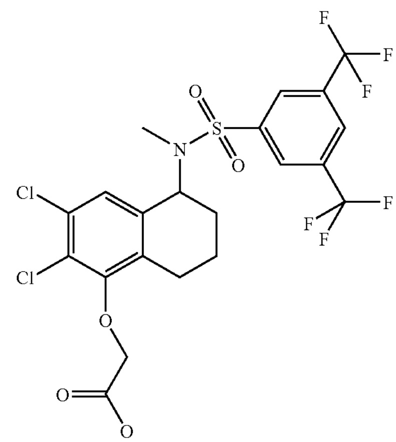 |
| 2-8 | {5-[(3,5-Bis-trifluoromethyl-benzenesulfonyl)-methyl-amino]-3-chloro-2-methyl-5,6,7,8-tetrahydro-naphthalen-1-yloxy}-acetic acid | 12.96 (br. s, 1H), 8.57 (s, 1H), 8.54 (s, 2H), 6.69 (s, 1H), 5.21-5.30 (m, 1H), 4.36 (s, 2H), 2.68 (d, J= 11.7 Hz, 1H), 2.60 (s, 3H), 2.40-2.46 (m, 1H), 2.22 (s, 3H), 1.81 (br. s, 1H), 1.45-1.73 (m, 3H) | 558 | 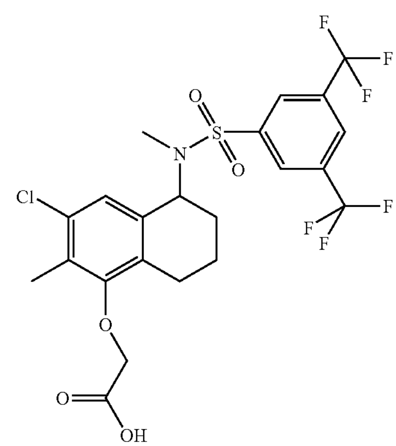 |
| 2-9 | {3-Chloro-5-[(2,5-dichloro-benzenesulfonyl)-methyl-amino]-2-fluoro-5,6,7,8-tetrahydro-naphthalen-1-yloxy}-acetic acid | 13.13 (br. s, 1H), 8.08 (t, J = 1.5 Hz, 1H), 7.81-7.83 (m, 2H), 6.93 (d, J = 6.6 Hz, 1H), 4.96 (dd, J =10.3, 5.4 Hz, 1H), 4.67 (s, 2H), 2.83 (m, 1H), 2.68 (s, 3H), 2.54 (br. s, 1H), 1.82-1.96 (m, 1H), 1.72-1.82 (m, 1H), 1.54-1.74 (m, 2H) | 496/498 | 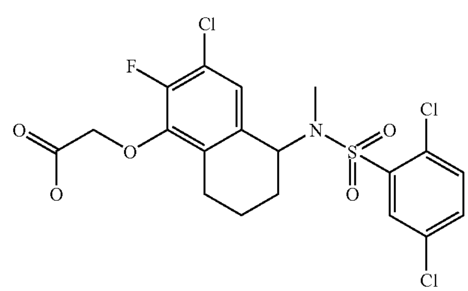 |
| 2-10 | {3-Chloro-5-[(2,5-dichloro-benzenesulfonyl)-methyl-amino]-5,6,7,8-tetrahydro-naphthalen-1-yloxy}-acetic acid | 8.06 (s, 1H), 7.65-7.89 (m, 2H), 6.76 (d, J = 2.0 Hz, 1H), 6.73 (br. s, 1H), 4.94 (dd, J = 10.3, 5.9 Hz, 1H), 4.67 (s, 2H), 2.64 (s, 3H), 2.61 (br. s, 1H), 2.29-2.44 (m, 1H), 1.84-1.93 (m, 1H), 1.71-1.84 (m, 1H), 1.51-1.71 (m, 2H) | 476/478 | 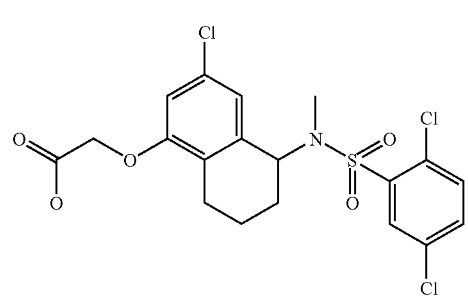 |

-continued

| Example No. | Systematic Name | ¹H NMR (400 MHz, DMSO-d₆) δ ppm | MS (M−+0H)⁻ | Structure |
|---|---|---|---|---|
| 2-11 | {3-Chloro-5-[(2,4-dichloro-benzenesulfonyl)-methyl-amino]-2-fluoro-5,6,7,8-tetrahydro-naphthalen-1-yloxy}-acetic acid | 13.07 (br. s, 1H), 8.10 (d, J = 8.5 Hz, 1H), 8.00 (d, J = 1.5 Hz, 1H), 7.69 (dd, J = 8.5, 1.5 Hz, 1H), 6.96 (d, J = 6.6 Hz, 1H), 4.82-4.98 (m, 1H), 4.68 (br. s, 2H), 2.71-2.92 (m, 1H), 2.65 (s, 3H), 2.57-2.62 (m, 1H), 1.85-1.98 (m, 1H), 1.53-1.83 (m, 3H) | 496/498 | 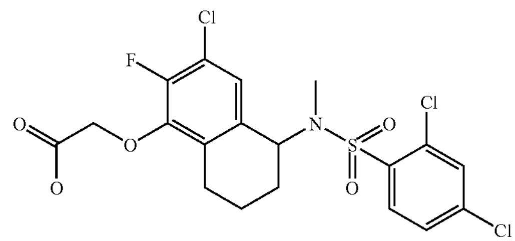 |
| 2-12 | {5-[(3-Bromo-5-trifluoromethyl-benzenesulfonyl)-methyl-amino]-3-chloro-2-fluoro-5,6,7,8-tetrahydro-naphthalen-1-yloxy}-acetic acid | 13.00 (br. s, 1H), 8.43 (br. s, 1H), 8.42 (br. s, 1H), 8.21 (s, 1H), 6.72 (d, J = 6.8 Hz, 1H), 5.14-5.24 (m, 1H), 4.69 (s, 2H), 2.75-2.90 (m, 1H), 2.59 (s, 3H), 2.42-2.46 (m, 1H), 1.83 (br. s, 1H), 1.56-1.76 (m, 2H), 1.45-1.56 (m, 1H) | 574/576 | 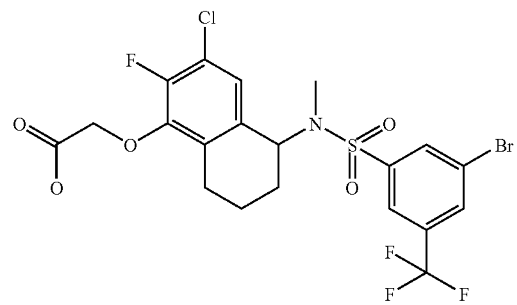 |
| 2-13 | {5-[(3-Bromo-5-trifluoromethyl-benzenesulfonyl)-methyl-amino]-3-chloro-5,6,7,8-tetrahydro-naphthalen-1-yloxy}-acetic acid | 13.05 (br. s, 1H), 8.42 (d, J = 6.4 Hz, 2H), 8.20 (s, 1H), 6.83 (s, 1H), 6.50 (s, 1H), 5.16-5.25 (m, 1H), 4.73 (s, 2H), 2.68 (d, J = 16.1 Hz, 1H), 2.58 (s, 3H), 2.36 (dd, J = 18.8, 10.5 Hz, 1H), 1.85 (br. s, 1H), 1.59-1.77 (m, 2H), 1.45-1.59 (m, 1H) | 554/556 | 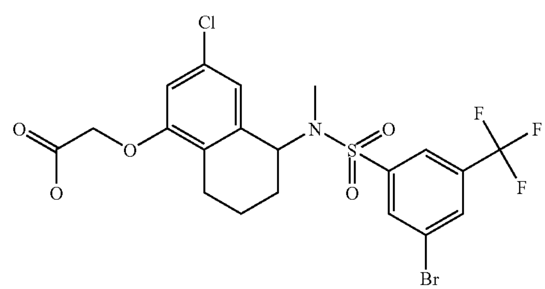 |
| 2-14 | {3-Chloro-5-[(3-fluoro-5-trifluoromethyl-benzenesulfonyl)-methyl-amino]-5,6,7,8-tetrahydro-naphthalen-1-yloxy}-acetic acid | 13.09 (br. s, 1H), 8.14-8.23 (m, 2H), 8.06 (s, 1H), 6.83 (s, 1H), 6.51 (s, 1H), 5.15-5.23 (m, 1H), 4.73 (s, 2H), 2.68 (d, J = 16.1 Hz, 1H), 2.59 (s, 3H), 2.36 (dd, J = 17.4, 10.5 Hz, 1H), 1.84 (br. s, 1H), 1.59-1.75 (m, 2H), 1.45-1.58 (m, 1H) | 494/496 | 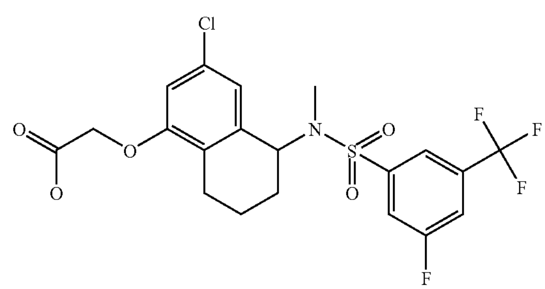 |
| 2-15 | {3-Chloro-2-fluoro-5-[(3-fluoro-5-trifluoromethyl-benzenesulfonyl)-methyl-amino]-5,6,7,8-tetrahydro-naphthalen-1-yloxy}-acetic acid | 13.02 (br. s, 1H), 8.19 (t, J = 9.8 Hz, 2H), 8.06 (s, 1H), 6.73 (d, J = 6.4 Hz, 1H), 5.07-5.22 (m, 1H), 4.70 (s, 2H), 2.82 (d, J = 17.1 Hz, 1H), 2.59 (s, 3H), 2.42-2.48 (m, 1H), 1.83 (br. s, 1H), 1.55-1.76 (m, 2H), 1.43-1.55 (m, 1H) | 512/514 | 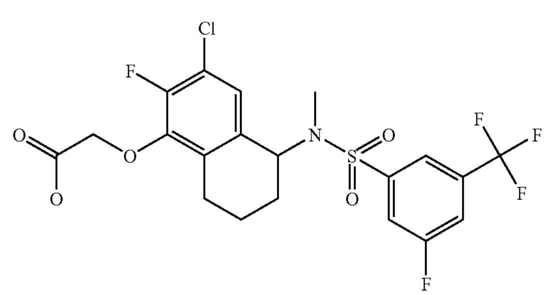 |

| Example No. | Systematic Name | $^1$H NMR (400 MHz, DMSO-$d_6$) δ ppm | MS (M −+0H)$^-$ | Structure |
|---|---|---|---|---|
| 2-16 | {5-[(2,4-Dichloro-trifluoromethyl-benzenesulfonyl)-methyl-amino]-3-fluoro-5,6,7,8-tetrahydro-naphthalen-1-yloxy}-acetic acid | 13.03 (br. s, 1H), 8.10 (d, J = 8.5 Hz, 1H), 7.99 (d, J = 2.0 1H), 7.68 (dd, J = 8.5, 2.0 Hz, 1H), 6.70 (d, J = 11.7 Hz, 1H), 6.56 (d, J = 10.3 Hz, 1H), 4.88-4.98 (m, 1H), 4.71 (s, 2H), 2.63 (s, 3H), 2.59-2.74 (m, 1H), 2.26-2.44 (m, 1H), 1.89 (br. s, 1H), 1.53-1.85 (m, 3H) | 460/462 | 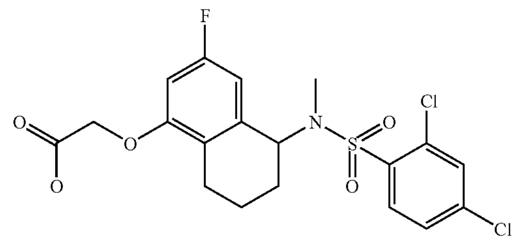 |
| 2-17 | {5-[(3,5-Bis-benzenesulfonyl)-methyl-amino]-3-fluoro-5,6,7,8-tetrahydro-naphthalen-1-yloxy}-acetic acid | 12.88 (br. s, 1H), 8.55 (s, 1H), 8.52 (s, 2H), 7.10 (dd, J = 11.7, 8.7 Hz, 1H), 6.84 (dd, J = 8.7, 5.1 Hz, 1H), 5.22-5.30 (m, 1H), 4.64 (s, 2H), 2.78-2.90 (m, 1H), 2.57 (s, 3H), 2.43-2.49 (m, 1H), 1.80 (br. s, 1H), 1.50-1.76 (m, 2H), 1.46 (br. s, 1H) | 551$^\#$ | 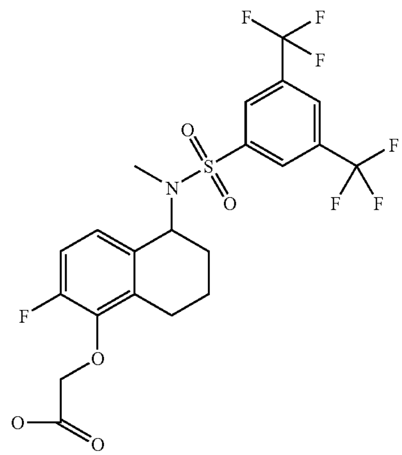 |
| 2-18 | {5-[(2,4-Dichloro-benzenesulfonyl)-methyl-amino]-2,3-difluoro-5,6,7,8-tetrahydro-naphthalen-1-yloxy}-acetic acid | 13.04 (br. s, 1H), 8.10 (d, J = 8.5 Hz, 1H), 8.00 (d, J = 2.0 Hz, 1H), 7.68 (dd, J = 8.5, 2.0 Hz, 1H), 6.84 (dd, J = 11.5, 7.6 Hz, 1H), 4.91 (dd, J =9.0, 6.1 Hz, 1H), 4.74 (s, 2H), 2.81 (d, J = 18.1 Hz, 1 H), 2.64 (s, 3H), 2.41-2.48 (m, 1H), 1.50-1.95 (m, 4H) | 478 | 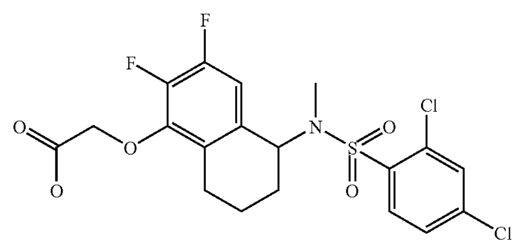 |
| 2-19 | {55-[(2,5-Dichloro-benzenesulfonyl)-methyl-amino]-3-fluoro-5,6,7,8-tetrahydro-naphthalen-1-yloxy}-acetic acid | 13.03 (br. s, 1H), 8.08 (s, 1H), 7.81 (s, 2H), 6.70 (d, J = 10.3 Hz, 1H), 6.53 (d, J = 10.3 Hz, 1H), 4.99 (dd, J = 10.0, 5.1 Hz, 1H), 4.72 (s, 2H), 2.66-2.76 (m, 1H), 2.66 (s, 3H), 2.29-2.44 (m, 1H), 1.56-1.95 (m, 4H) | 484$^\#$ | 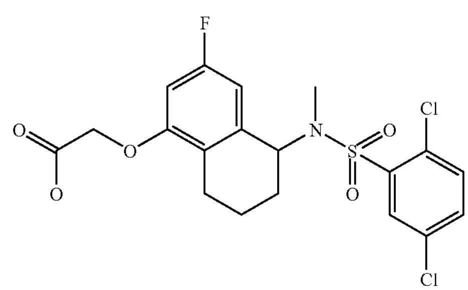 |
| 2-20 | {5-[(3-Bromo-5-trifluoromethyl-benzenesulfonyl)-methyl-amino]-2,3-difluoro-5,6,7,8-tetrahydro-naphthalen-1-yloxy}-acetic acid | 13.04 (br. s, 1H), 8.43 (s, 1H), 8.41 (s, 1H), 8.21 (s, 1H), 6.66 (dd, J = 11.0, 7.6 Hz, 1H), 5.10-5.23 (m, 1H), 4.74 (s, 2H), 2.78 (d, J = 17.6 Hz, 1H), 2.59 (s, 3H), 2.36-2.45 (m, 1H), 1.82 (br. s, 1 H), 1.37-1.76 (m, 3H) | 556 | 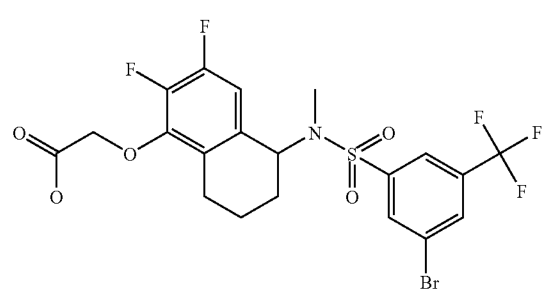 |

| Example No. | Systematic Name | ¹H NMR (400 MHz, DMSO-d₆) δ ppm | MS (M −+0H)⁻ | Structure |
|---|---|---|---|---|
| 2-21 | {5-[(2,5-Dichloro-benzenesulfonyl)-methyl-amino]-2,3-difluoro-5,6,7,8-tetrahydro-naphthalen-1-yloxy}-acetic acid | 13.54 (br. s, 1H), 8.08 (s, 1H), 7.82 (s, 2H), 6.80 (dd, J = 11.5, 7.6 Hz, 1H), 4.96 (dd, J = 10.0, 5.6 Hz, 1H), 4.73 (s, 2H), 2.74-2.86 (m, 1H), 2.67 (s, 3H), 2.39-2.47 (m, 1H), 1.54-1.93 (m, 4H) | 478 | 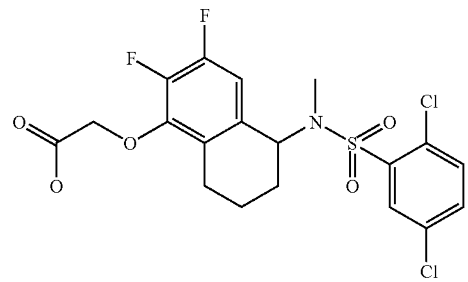 |
| 2-22 | {5-[(3-Bromo-5-trifluoromethyl-benzenesulfonyl)-methyl-amino]-3-fluoro-5,6,7,8-tetrahydro-naphthalen-1-yloxy}-acetic acid | 13.05 (br. s, 1H), 8.43 (br. s, 1H), 8.41 (br. s, 1H), 8.20 (s, 1H), 6.70 (dd, J =10.8, 1.5 Hz, 1H), 6.35 (dd, J = 9.8, 1.5 Hz, 1H), 5.12-5.27 (m, 1H), 4.72 (s, 2H), 2.67 (d, J = 17.6 Hz, 1H), 2.58 (s, 3H), 2.27-2.43 (m, 1H), 1.84 (br. s, 1H), 1.56-1.77 (m, 2H), 1.52 (br. s, 1H) | 562# | 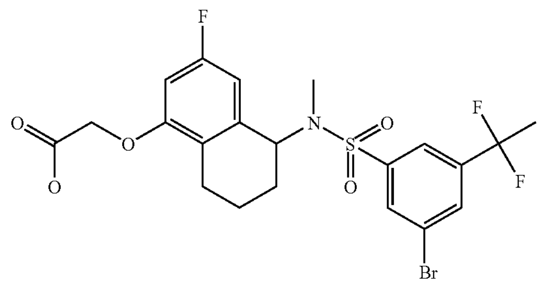 |
| 2-23 | {3-Fluoro-5-[(3-fluoro-5-trifluoromethyl-benzenesulfonyl)-methyl-amino]-5,6,7,8-tetrahydro-naphthalen-1-yloxy}-acetic acid | 13.05 (br. s, 1H), 8.20 (d, J = 7.8 Hz, 1H), 8.17 (d, J = 8.8 Hz, 1H), 8.06 (s, 1H), 6.70 (dd, J = 10.8, 2.0 Hz, 1H), 6.36 (d, J = 9.8 Hz, 1H), 5.13-5.23 (m, 1H), 4.73 (s, 2H), 2.67 (d, J = 16.1 Hz, 1H), 2.59 (s, 3H), 2.26-2.43 (m, 1H), 1.84 (br. s, 1H), 1.57-1.76 (m, 2H), 1.44-1.57 (m, 1H) | 502# | 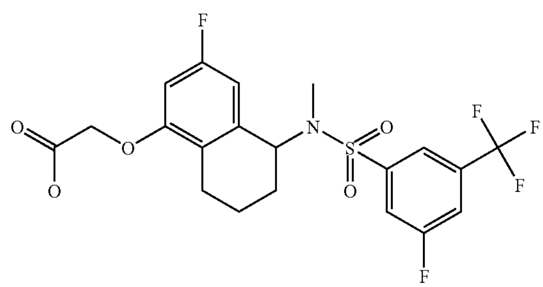 |
| 2-24 | {2,3-Difluoro-5-[(3-fluoro-5-trifluoromethyl-benzenesulfonyl)-methyl-amino]-5,6,7,8-tetrahydro-naphthalen-1-yloxy}-acetic acid | 13.05 (br. s, 1H), 8.20 (d, J = 7.8 Hz, 1H), 8.16 (d, J = 8.8 Hz, 1H), 8.06 (s, 1H), 6.66 (dd, J = 11.5, 7.6 Hz, 1H), 5.07-5.20 (m, 1H), 4.74 (s, 2H), 2.78 (d, J = 16.6 Hz, 1H), 2.59 (s, 3H), 2.39-2.48 (m, 1H), 1.82 (br. s, 1H), 1.54-1.75 (m, 2H), 1.42-1.53 (m, 1H) | 520# | 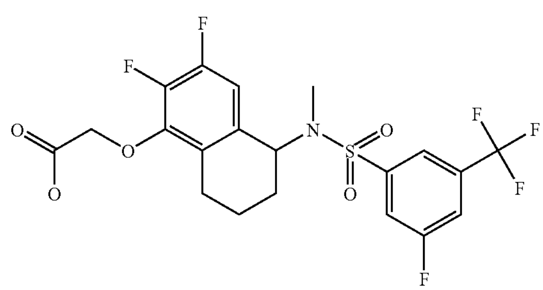 |
| 2-25 | (2,3-Difluoro-5-{[5-(3-isopropyl-phenyl)-pyridine-2-sulfonyl]-methyl-amino}-5,6,7,8-tetrahydro-naphthalen-1-yloxy)-acetic acid | 13.04 (br. s, 1H), 9.14 (s, 1H), 8.41 (d, J = 8.2 Hz, 1H), 8.08 (d, J = 8.2 Hz, 1H), 7.71 (br. s, 1H), 7.65 (d, J = 7.1 Hz, 1H), 7.48 (t, J = 7.1 Hz, 1H), 7.39 (d, J = 7.1 Hz, 1H), 6.86 (dd, J = 10.9, 7.7 Hz, 1H), 5.07 (br. s, 1H), 4.74 (br. s, 2H), 2.89-3.08 (m, 1H), 2.81 (d, J = 17.1 Hz, 1H), 2.65 (s, 3H), 2.40-2.48 (m, 1H), 1.88 (br. s, 1H), 1.73 (br. s, 3H), 1.28 (d, J = 6.6 Hz, 6H) | 531## | 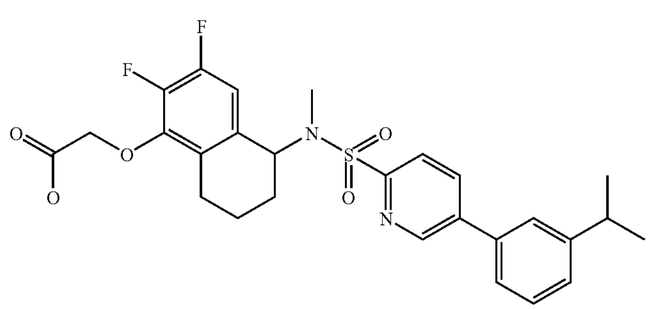 |

| Example No. | Systematic Name | $^1$H NMR (400 MHz, DMSO-d$_6$) δ ppm | MS (M −+0H)$^−$ | Structure |
|---|---|---|---|---|
| 2-26 | (3-Fluoro-5-{[5-(3-isopropyl-phenyl)-pyridine-2-sulfonyl]-methyl-amino}-5,6,7,8-tetrahydro-naphthalen-1-yloxy)-acetic acid | 13.06 (br. s, 1H), 9.14 (s, 1H), 8.41 (d, J = 8.4 Hz, 1H), 8.08 (d, J = 8.4 Hz, 1H), 7.71 (s, 1H), 7.65 (d, J = 7.8 Hz, 1H), 7.48 (t, J = 7.8 Hz, 1H), 7.39 (d, J = 7.8 Hz, 1H), 6.70 (d, J = 10.5 Hz, 1H), 6.56 (d, J = 10.0 Hz, 1H), 5.01-5.13 (m, 1H), 4.72 (s, 2H), 2.93-3.07 (m, 1H), 2.67-2.75 (m, 1H), 2.65 (s, 3H), 2.30-2.45 (m, 1H), 1.89 (br. s, 1H), 1.55-1.81 (m, 3H), 1.28 (d, 6H) | 513## | 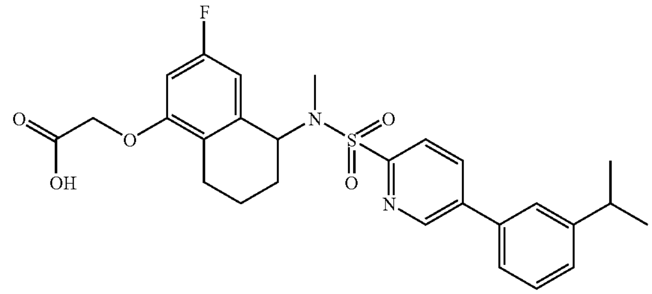 |
| 2-27 | (3-Chloro-5-{[5-(3-isopropyl-phenyl)-pyridine-2-sulfonyl]-methyl-amino}-5,6,7,8-tetrahydro-naphthalen-1-yloxy)-acetic acid | 12.88 (br. s, 1H), 9.14 (d, J = 2.0 Hz, 1H), 8.41 (dd, J = 8.2, 2.0 Hz, 1H), 8.09 (d, J = 8.2 Hz, 1H), 7.70 (s, 1H), 7.65 (d, J = 8.1 Hz, 1H), 7.44-7.51 (m, 1H), 7.39 (d, J = 7.6 Hz, 1H), 6.82 (d, J = 1.2 Hz, 1H), 6.71 (s, 1H), 4.98-5.15 (m, 1H), 4.73 (s, 2H), 2.90-3.07 (m, 1H), 2.68-2.75 (m, 1H), 2.66 (s, 3H), 2.31-2.46 (m, 1H), 1.88 (br. s., 1H), 1.55-1.80 (m, 3H), 1.27 (d, 6H) | 529## | 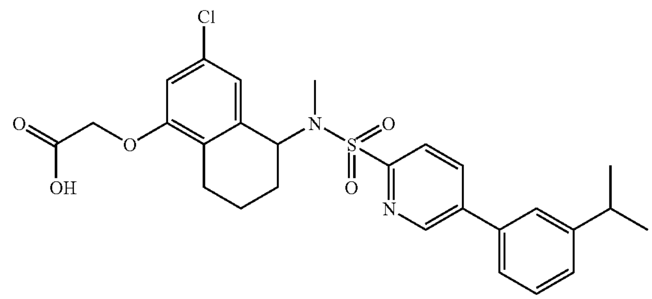 |
| 2-28 | (3-Chloro-2-fluoro-5-{[5-(3-isopropyl-phenyl)-pyridine-2-sulfonyl]-methyl-amino}-5,6,7,8-tetrahydro-naphthalen-1-yloxy)-acetic acid | 13.02 (s, 1H), 9.14 (br. s, 1H), 8.41 (d, J = 8.8 Hz, 1H), 8.09 (d, J = 7.3 Hz, 1 7.70 (br. s, 1H), 7.61-7.68 (m, 1H), 7.43-7.53 (m, 1H), 7.40 (br. s, 1H), 6.87-6.98 (m, 1H), 5.07 (br. s, 1H), 4.70 (br. s, 2H), 3.00 (br. s, 1H), 2.75-2.90 (m, 1H), 2.66 (br. s, 3H), 2.41-2.48 (m, 1H), 1.89 (br. s, 1H), 1.54-1.81 (m, 3H), 1.27 (d, J = 5.9 Hz, 6H) | 547## | 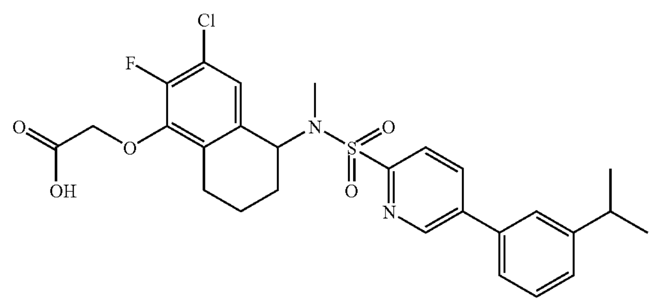 |
| 2-29 | {5-[(2,5-Dichloro-benzenesulfonyl)-methyl-amino]-2-fluoro-5,6,7,8-tetrahydro-naphthalen-1-yloxy}-acetic acid | 12.92 (br. s, 1H), 8.07 (s, 1H), 7.80 (s, 2H), 7.12 (dd, J = 11.7, 8.6 Hz, 1H), 6.91 (dd, J = 8.6, 5.0 Hz, 1H), 4.94-5.04 (m, 1H), 4.64 (s, 2H), 2.83-2.94 (m, 1H), 2.64 (s, 3H), 2.52-2.60 (m, 1H), 1.84-1.93 (m, 1H), 1.68 (br. s, 3H) | 484# | 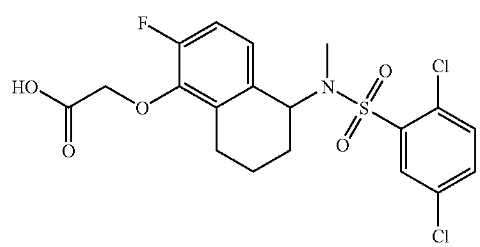 |
| 2-30 | {5-[(2,4-Dichloro-benzenesulfonyl)-methyl-amino]-2-fluoro-5,6,7,8-tetrahydro-naphthalen-1-yloxy}-acetic acid | 12.93 (br. s, 1H), 8.09 (d, J = 8.2 Hz, 1H), 7.98 (s, 1H), 7.68 (d, J = 8.2 Hz, 1H), 7.13 (dd, J = 11.2, 8.8 Hz, 1H), 6.94 (dd, J = 8.8, 4.9 Hz, 1H), 4.85-5.04 (m, 1H), 4.64 (s, 2H), 2.79-2.96 (m, 1H), 2.61 (s, 3H), 2.53-2.58 (m, 1H), 1.82-1.94 (m, 1H), 1.74 (br. s, 3H) | 484# | 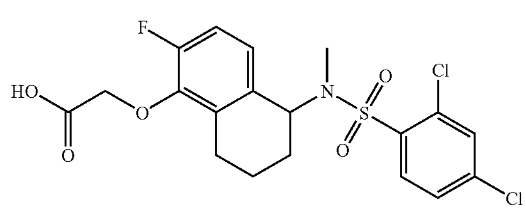 |

-continued

| Example No. | Systematic Name | ¹H NMR (400 MHz, DMSO-d₆) δ ppm | MS (M −+OH)⁻ | Structure |
|---|---|---|---|---|
| 2-31 | (2-Fluoro-5-{[5-(3-isopropyl-phenyl)-pyridine-2-sulfonyl]-methyl-amino}-5,6,7,8-tetrahydro-naphthalen-1-yloxy)-acetic acid | 12.93 (br. s, 1H), 9.14 (d, J = 2.1 Hz, 1H), 8.40 (dd, J = 8.2, 2.1 Hz, 1H), 8.07 (d, J = 8.2 Hz, 1H), 7.72 (s, 1H), 7.66 (d, J = 7.8 Hz, 1H), 7.48 (t, J = 7.8 Hz, 1H), 7.39 (d, J = 7.8 Hz, 1H), 7.13 (dd, J = 12.0, 8.8 Hz, 1H), 7.00 (dd, J = 8.8, 5.3 Hz, 1H), 5.00-5.19 (m, 1H), 4.65 (s, 2H), 2.95-3.07 (m, 1H), 2.79-2.95 (m, 1H), 2.63 (s, 3H), 2.52-2.61 (m, 1H), 1.81-1.96 (m, 1H), 1.51-1.77 (m, 3H), 1.28 (d, J = 6.8 Hz, 6H) | 513## | 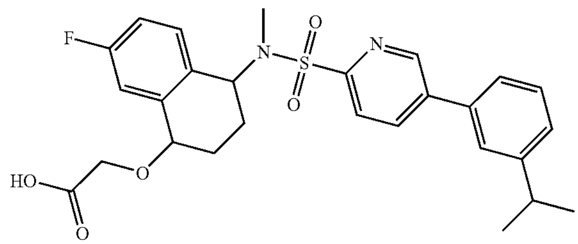 |
| 2-32 | {(R)-3-Bromo-5-[(3-fluoro-5-trifluoromethyl-benzenesulfonyl)-methyl-amino]-5,6,7,8-tetrahydro-naphthalen-1-yloxy}-acetic acid | (300 MHz, CDCl₃) 7.95 (s, 1H), 7.79 (d, J = 7.5 Hz, 1H), 7.59 (d, J = 7.8 Hz, 1H), 6.87 (s, 1H), 6.72 (s, 1H), 5.07-5.23 (m, 1H), 4.66 (s, 2H), 2.81 (d, J = 17.8 Hz, 1H), 2.64 (s, 3H), 2.34-2.51 (m, 1H), 1.89-2.02 (m, 1H), 1.65 (d, J = 7.2 Hz, 3H) | 562# | 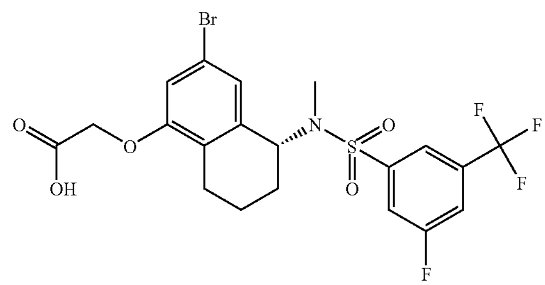 |
| 2-33 | {(R)-3-Bromo-5-[(3-fluoro-5-trifluoromethyl-benzenesulfonyl)-methyl-amino]-5,6,7,8-tetrahydro-naphthalen-1-yloxy}-acetic acid | (300 MHz, CDCl₃) 7.71 (s, 1H), 7.55 (s, 1H), 7.35 (s, 1H), 6.89 (s, 1H), 6.71 (s, 1H), 5.01-5.25 (m, 1H), 4.64 (s, 2H), 3.93 (s, 3H), 2.80 (d, J = 16.3 Hz, 1H), 2.62 (s, 3H), 2.30-2.53 (m, 1H), 1.83-2.02 (m, 1H), 1.53-1.80 (m, 3H) | 574# | 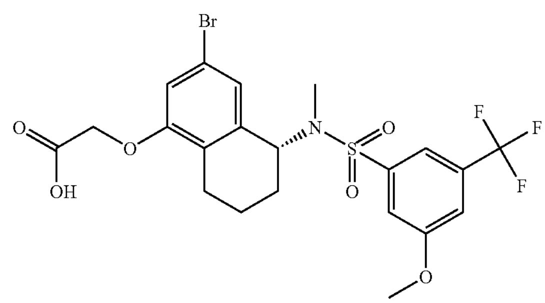 |

(M + Na)⁺
(M ++OH)⁺

Activity and Use of the Compounds

The compounds of formula I possess valuable pharmacological properties. It has been found that said compounds are antagonists at the CRTH2 receptor and may be useful in treating diseases and disorders associated with that receptor such as asthma. The activity of the present compounds as CRTH2 receptor antagonists is demonstrated by the following biological assays.

Human CRTH2 Receptor Binding Assay

A whole cell receptor binding assay using [³H]ramatroban as the competing radioactive ligand was employed to evaluate the compound binding activity to human CRTH2. The radioactive ligand [³H]ramatroban was synthesized according to Sugimoto et. al. (*Eur. J. Pharmacol.* 524, 30-37, 2005) to a specific activity of 42 Ci/mmol.

A cell line stably expressing human CRTH2 was established by transfecting CHO-K1 cells with two mammalian expression vectors that harbored human CRTH2 and G-alpha16 cDNAs, respectively, using FuGene® 6 transfection reagent (from Roche). Stable clones expressing CRTH2 were selected by staining each clone with BM16 (BD Pharmingen™ from BD Biosciences, a division of Becton, Dickinson and Company), which is a rat monoclonal antibody to human CRTH2. The cells were maintained as monolayer cultures in Ham's F-12 medium containing 10% fetal bovine serum, 100 units/mL penicillin, 100 mg/mL streptomycin, 2 mM glutamine, 0.5 mg/mL G418 (geneticin) for CRTH2, and 0.2 mg/mL hygromycin-B (for G-alpha 16). For whole cell receptor binding assay, the monolayer cells were rinsed once with PBS (phosphate buffered saline), dissociated using diammonium ethylenediaminetetraacetate (Versene™ EDTA from the Dow Chemical Company), and suspended in PBS containing 10 mM $MgCl_2$ and 0.06% BSA (bovine serum albumin) at 1.5×10⁶ cells/mL.

The binding reactions (0.2 mL) were performed in 96-well plates at room temperature in PBS containing 1.5×10⁵ cells, 10 mM MgCl$_2$, 0.06% BSA, 20 nM [$^3$H]ramatroban, and test compound at various concentrations. After 1 hour of binding reactions, the cells were harvested on GF™/B filter microplates (microtiter plates with embedded glass fiber from PerkinElmer, Inc.) and washed 5 times with PBS using a Filtermate™ Harvester (a cell harvester that harvests and washes cells from microplates from PerkinElmer, Inc.). The radioactivities bound to the cells were determined using a microplate scintillation counter (TopCount® NXT, from PerkinElmer, Inc.) after adding 50 µL of Microscint™ 20 scintillation fluid (from PerkinElmer, Inc.) to each well of the filter plates. The radioactivity from non-specific binding was determined by replacing compound with 10 µM of 15(R)-15-methyl PGD$_2$ (from Cayman Chemical Company) in the reaction mixtures. The radioactivity bound to the cells in the absence of compound (total binding) was determined by replacing compound with 0.25% of DMSO (dimethyl sulfoxide) in the reaction mixture. Specific binding data were obtained by subtracting the radioactivity of non-specific binding from each binding data.

The IC$_{50}$ value is defined as the concentration of the tested compound that is required for 50% inhibition of total specific binding. In order to calculate the IC$_{50}$ value, the percent inhibition data were determined for 7 concentrations for each compound. The percent inhibition for a compound at each concentration was calculated according to the following formula, [1-(specific binding in the presence of compound)/(total specific binding)]×100. The IC$_{50}$ value was then obtained by fitting the percent inhibition data to a sigmoidal dose-response (4 parameter logistic) model in the XLfit® software Excel add-in program [from ID Business Solutions Ltd., model 205, where $F(x)=(A+(B-A)/(1+((C/x)^D)))$].

The acid compounds of the foregoing examples were tested using the above Human CRTH2 Receptor Binding Assay. The results of the assay showed that all of these compounds have binding activity exhibiting IC$_{50}$ values ranging from 0.0024 µM to 1.1561 µM. For instance, the following table shows the specific IC$_{50}$ values for these compounds:

| Example No. | Human CRTH2 Binding IC$_{50}$ (µM) |
|---|---|
| Example 1-1 | 0.0024 |
| Example 1-2 | 0.1950 |
| Example 1-3 | 0.1470 |
| Example 1-4 | 0.0640 |
| Example 1-5 | 0.0284 |
| Example 1-6 | 0.0058 |
| Example 1-7 | 0.2920 |
| Example 1-8 | 0.0035 |
| Example 1-9 | 0.0058 |
| Example 1-10 | 0.0114 |
| Example 1-11 | 0.0035 |
| Example 1-12 | 0.0261 |
| Example 1-13 | 0.0071 |
| Example 1-14 | 0.0077 |
| Example 1-15 | 0.008 |
| Example 1-16 | 0.0038 |
| Example 1-17 | 0.0036 |
| Example 1-18 | 0.0028 |
| Example 1-19 | 0.0029 |
| Example 1-20 | 0.0025 |
| Example 1-21 | 0.0028 |
| Example 1-22 | 0.0337 |
| Example 1-23 | 0.0036 |
| Example 1-24 | 0.0037 |
| Example 1-25 | 0.0959 |
| Example 1-26 | 0.0422 |
| Example 1-27 | 0.0401 |
| Example 1-28 | 0.0042 |
| Example 1-29 | 0.0182 |
| Example 1-30 | 0.0461 |
| Example 1-31 | 0.1544 |
| Example 1-32 | 0.2686 |
| Example 1-33 | 0.0810 |
| Example 1-34 | 0.0086 |
| Example 1-35 | 0.0070 |
| Example 1-36 | 0.0045 |
| Example 1-37 | 0.0028 |
| Example 1-38 | 0.0034 |
| Example 1-39 | 0.0026 |
| Example 1-40 | 0.0063 |
| Example 1-41 | 0.0034 |
| Example 1-42 | 0.0032 |
| Example 1-43 | 0.0109 |
| Example 1-44 | 0.0164 |
| Example 2-1 | 0.0080 |
| Example 2-2 | 0.3110 |
| Example 2-3 | 0.1770 |
| Example 2-4 | 0.0083 |
| Example 2-5 | 0.0059 |
| Example 2-6 | 0.0929 |
| Example 2-7 | 0.3333 |
| Example 2-8 | 0.6379 |
| Example 2-9 | 1.1561 |
| Example 2-10 | 0.8594 |
| Example 2-11 | 0.5357 |
| Example 2-12 | 0.0123 |
| Example 2-13 | 0.0062 |
| Example 2-14 | 0.0112 |
| Example 2-15 | 0.0141 |
| Example 2-16 | 0.9810 |
| Example 2-17 | 0.1990 |
| Example 2-18 | 2.5240 |
| Example 2-19 | 2.6428 |
| Example 2-20 | 0.2884 |
| Example 2-21 | 2.1016 |
| Example 2-22 | 0.0054 |
| Example 2-23 | 0.1983 |
| Example 2-24 | 0.3799 |

Calcium Flux Assay Using Fluorometric Imaging Plate Reader Cell Culture Conditions CHO-K1 cells previously transfected with G-alpha 16 were subsequently transfected with the human CRTH2 receptor and the neomycin resistance gene. Following selection in 800 µg/mL G418 (geneticin), individual clones were assayed for their receptor expression based on staining with an anti human CRTH2 IgG, followed by assaying for their response to 13,14-dihydro-15-keto Prostaglandin D$_2$ (DK-PDG$_2$) (ligand) in the Ca$^{2+}$ Flux assay. Positive clones were then cloned by limiting dilution cloning. The transfected cells were cultured in Ham's F-12 medium supplemented with 10% fetal bovine serum, 2 mM glutamine, 100 U/mL penicillin/100 µg/mL streptomycin, 200 µg/mL hygromycin B, and 800 µg/mL G418 (geneticin). Cells were harvested with trypsin-EDTA (trypsin-ethylenediaminetetraaceticacid) and counted using ViaCount® reagent (from Guava Technologies, Inc. which contains two DNA-binding dyes that enable the reagent user to distinguish between viable and non-viable cells). The cell suspension volume was adjusted to 2.5×10$^5$ cells/mL with complete growth media. Aliquots of 50 µL were dispensed into BD Falcon™ 384 well black/clear microplates (from BD Biosciences, a division of Becton, Dickinson and Company) and the microplates were placed in a 37° C./CO$_2$ incubator overnight. The following day, the microplates were used in the assay.

Dye Loading and Assay:

Loading Buffer containing dye (from the FLIPR® Calcium 3 Assay Kit from Molecular Devices, a division of MDS Analytical Technologies and MDS Inc.) was prepared by dissolving the contents of one bottle into 200 mL Hank's Balanced Salt Solution containing 20 mM HEPES (4-(2-hydroxyethyl)-1-piperazineethanesulfonic acid) and 2.5 mM probenecid. Growth media was removed from the cell plates and 25 μL of Hank's Balanced Salt Solution (HBSS) containing 20 mM HEPES, 0.05% BSA and 2.5 mM probenecid was added to each well followed by 25 μL of diluted dye using a Multidrop dispenser. The plates were then incubated for 1 hour at 37° C.

During the incubation, test compound plates were prepared by adding 90 μL of HBSS/20 mM HEPES/0.005% BSA buffer to the 2 μL of serial diluted compounds. To prepare serial diluted compounds, 20 mM stocks of compounds were dissolved in 100% DMSO. The compound dilution plate was set up as follows: well #1 received 5 μL of compound plus 10 μL of DMSO. Wells 2-10 received 10 μL of DMSO. 5 μL was mixed and transferred from well #1 into well #2. 1:3 serial dilutions were continued out 10 steps. 2 μL of diluted compound was transferred into duplicate wells of a 384 well "assay plate" and then 90 μL of buffer was added.

After incubation, both the cell and "assay plate" plates were brought to the fluorometric imaging plate reader (FLIPR®) and 20 μL of the diluted compounds were transferred to the cell plates by the FLIPR®. Plates were then incubated for 1 hour at room temperature. After the hour incubation, plates were returned to the FLIPR® and 20 μL of 4.5× concentrated ligand was added to the cell plates. During the assay, fluorescence readings were taken simultaneously from all 384 wells of the cell plate every 1.5 seconds. Five readings were taken to establish a stable baseline, then 20 μL of sample was rapidly (30 μL/sec) and simultaneously added to each well of the cell plate. The fluorescence was continuously monitored before, during and after sample addition for a total elapsed time of 100 seconds. Responses (increase in peak fluorescence) in each well following agonist addition were determined. The initial fluorescence reading from each well, prior to ligand stimulation, was used as a zero baseline value for the data from that well. The responses were expressed as % inhibition of the buffer control. The $IC_{50}$ value, defined as the concentration of a compound that was required for 50% inhibition of the buffer control, was calculated by fitting the percent inhibition data for 10 concentrations to a sigmoidal dose-response (4 parameter logistic) model using Genedata Screener® Condoseo software program [from Genedata AG, model 205, where $F(x)=(A+(B-A)/(1+((C/x)^D)))$].

Representative compounds tested in the binding assay were tested using the above FLIPR® assay (examples 1-1 to 1-17, 1-24, 1-25, 2-1 to 2-14). The results of the FLIPR® assay showed that all of the representative compounds tested in this assay have activity exhibiting $IC_{50}$ values ranging from 0.0001 μM to 3.46 μM.

DK-PGD$_2$-Induced IL-13 Production Assay in Th2 Cells

Inhibition of 13,14-dihydro-15-keto Prostaglandin D$_2$ (DK-PGD$_2$)-induced IL-13 production in T helper type 2 (Th2) cells was applied to evaluate compound cellular potency.

Cultures of Th2 cells were established from blood of healthy human volunteers according to the following procedure. Peripheral blood mononuclear cells (PBMC) were first isolated from 50 mL of fresh blood by Ficoll-Hypaque density gradient centrifugation, followed by CD4$^+$ cell purification using a CD4$^+$ T Cell Isolation Kit II (from Miltenyi Biotec Inc.). The CD4$^+$ T cells were then differentiated to Th2 cells by culturing the cells in X-VIVO 15® medium (from Cambrex BioScience Walkersville Inc.) containing 10% human AB serum (serum of blood type AB from Invitrogen Corporation), 50 U/mL of recombinant human interleukin-2 (rhIL-2) (from PeproTech Inc.) and 100 ng/mL of recombinant human interleukin-4 (rhIL-4) (from PeproTech Inc.) for 7 days. The Th2 cells were isolated using a CD294 (CRTH2) MicroBead Kit (from Miltenyi Biotec Inc.) and amplified in X-VIVO 15® medium containing 10% human AB serum and 50 U/mL of rhIL-2 for 2 to 5 weeks. In general, 70% to 80% of the Th2 cells used in the assay are CRTH2-positive when analyzed by fluorescence-activated cell sorting using the BM16 antibody (as previously described) conjugated to phycoerythrin (PE).

To determine cellular inhibitory potency, compounds at various concentrations were incubated with $2.5 \times 10^4$ Th2 cells and 500 nM DK-PGD$_2$ for 4 hrs at 37° C. in 200 μL of X-VIVO 15® medium containing 10% human AB serum. IL-13 production to the medium was detected by ELISA (enzyme-linked immunosorbent assay) using an "Instant ELISA™" kit (from Bender MedSystems Inc.) according to the procedure suggested by the vendor. The spontaneous production of IL-13 by Th2 cells was determined in the absence of DK-PGD2 stimulation and the value was subtracted from that in the presence of each compound for percent inhibition and $IC_{50}$ calculations.

The percent inhibition of interleukin 13 (IL-13) production for a compound at various concentrations was calculated according to the following formula, [1-(IL-13 production in the presence of compound)/(IL-13 production in the presence of 0.15% DMSO)]×100. The $IC_{50}$ value, defined as the concentration of a compound that is required for 50% inhibition of IL-13 production, was calculated by fitting the percent inhibition data for 7 concentrations to a sigmoidal dose-response (4 parameter logistic) model in the XLfit® software Excel add-in program [ID Business Solutions Ltd., model 205, where $F(x)=(A+(B-A)/(1+((C/x)^D)))$].

Representative compounds tested in the binding assay were tested using the foregoing DK-PGD$_2$-induced IL-13 production assay (examples 1-1 to 1-18, 1-20 to 1-25, 1-37 to 1-43, 2-01 to 2-17). The results of the DK-PGD$_2$-induced IL-13 production assay showed that, with the exception of examples 1-2, 2-2, 2-3, 2-7 to 2-9, 2-11, and 2-16 (which exhibited $IC_{50}$ values greater than 10), the compounds tested in this assay exhibited activity in inhibiting IL-13 production, with $IC_{50}$ values ranging from 0.004 μM to 5.982 μM.

Thus, the compounds of the present invention are useful since the compounds tested show some activity in at least one of the above three assays (i.e., binding at the CRTH2 receptor), and therefore may be useful as antagonists in treating diseases and disorders associated with this receptor such as asthma.

In one embodiment, the present invention relates to a method for the treatment and/or prevention of diseases and disorders which are associated with the modulation of CRTH2 receptors, which method comprises administering a therapeutically effective amount of a compound of formula I to a human being or animal. A method for the treatment and/or prevention of an inflammatory or allergic disease or disorder is preferred. Such diseases or disorders may include (but are not limited to) asthma, chronic obstructive pulmonary disease (COPD), allergic inflammation, and atopic dermatitis.

The present invention is also directed to the administration of a therapeutically effective amount of a compound of formula I in combination or association with other drugs or active agents for the treatment of inflammatory or allergic diseases and disorders. In one embodiment, the present invention relates to a method for the treatment and/or prevention of such diseases or disorders comprising administering to a human or animal simultaneously, sequentially, or separately, a therapeutically effective amount of a compound of formula I and another drug or active agent (such as another anti-inflammatory or anti-allergic drug or agent). These other drugs or active agents may have the same, similar, or a completely different mode of action. Suitable other drugs or active agents may include, but are not limited to: Beta2-adrenergic agonists such as albuterol or salmeterol; corticosteroids such as dexamethasone or fluticasone; antihistamines such as loratidine; leukotriene antagonists such as montelukast or zafirlukast; anti-IgE antibody therapies such as omalizumab; anti-infectives such as fusidic acid (particularly for the treatment of atopic dermatitis); anti-fungals such as clotrimazole (particularly for the treatment of atopic dermatitis); immunosuppressants such as tacrolimus and pimecrolimus; other antagonists of PGD2 acting at other receptors such as DP antagonists; inhibitors of phoshodiesterase type 4 such as cilomilast; drugs that modulate cytokine production such as inhibitors of TNF-alpha converting enzyme (TACE); drugs that modulate the activity of Th2 cytokines IL-4 and IL-5 such as blocking monoclonal antibodies and soluble receptors; PPAR-gamma agonists such as rosiglitazone; and 5-lipoxygenase inhibitors such as zileuton.

Unless stated to the contrary, all compounds in the examples were prepared and characterized as described. All patents and publications cited herein are hereby incorporated by reference in their entirety.

The invention claimed is:
1. A compound of formula I:

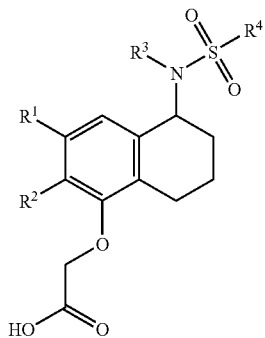

I or a pharmaceutically acceptable salt or ester thereof, wherein:
$R^1$ is hydrogen, halogen, methoxy, or phenyl; and $R^2$ is hydrogen, fluoro, chloro, or alkyl; with the proviso that $R^1$ and $R^2$ are not both hydrogen;
$R^3$ is hydrogen or methyl; and
$R^4$ is phenyl substituted by two substituents independently selected from the group consisting of:
(1) halogen,
(2) lower alkyl optionally substituted by halogen,
(3) lower alkanoyl,
(4) lower alkoxy,
(5) lower alkylsulfanyl, lower alkylsulfinyl, or lower alkylsulfonyl, and
(6) lower cycloalkylsulfanyl, lower cycloalkylsulfinyl, or lower cycloalkylsulfonyl; or alternatively,
$R^4$ is pyridine substituted by one or two substituents independently selected from the group consisting of:
(1) halogen,
(2) lower alkyl optionally substituted by halogen, and
(3) phenyl or pyridine, wherein said phenyl or pyridine is optionally substituted by lower alkyl, lower alkylsulfanyl, lower alkylsulfonyl, lower cycloalkylsulfanyl, or lower cycloalkylsulfonyl.

2. A compound of claim 1 wherein $R^3$ is hydrogen.
3. A compound of claim 1 wherein $R^3$ is methyl.
4. A compound of claim 1 wherein $R^4$ is phenyl substituted by two substituents independently selected from the group consisting of: (1) halogen, and (2) lower alkyl optionally substituted by halogen.
5. A compound of claim 1 wherein $R^4$ is phenyl substituted by two substituents independently selected from the group consisting of:
(1) fluoro;
(2) chloro;
(3) bromo;
(4) lower alkyl
(5) lower alkanoyl;
(6) lower alkylsulfanyl, lower alkylsulfinyl, or lower alkylsulfonyl;
(7) lower cycloalkylsulfanyl, lower cycloalkylsulfinyl, or lower cycloalkylsulfonyl;
(8) trifluoromethyl, difluoromethyl, or fluoromethyl; and
(9) 1,1-difluoroethyl.
6. A compound of claim 1 wherein $R^4$ is phenyl substituted by two substituents independently selected from the group consisting of:
(1) fluoro;
(2) chloro;
(3) bromo;
(4) methyl;
(5) ethyl;
(6) propyl or isopropyl;
(7) butyl, sec-butyl, or tert-butyl;
(8) trifluoromethyl, difluoromethyl, or fluoromethyl; and
(9) 1,1-difluoroethyl.
7. A compound of claim 1 wherein $R^4$ is phenyl substituted by two substituents independently selected from the group consisting of:
(1) fluoro;
(2) chloro;
(3) bromo; and
(4) trifluoromethyl.
8. A compound of claim 1 wherein $R^4$ is pyridine substituted by one substituent selected from the group consisting of:
(1) halogen;
(2) lower alkyl optionally substituted by halogen; and
(3) phenyl or pyridine, wherein said phenyl or pyridine is optionally substituted by lower alkyl.
9. A compound of claim 1 wherein $R^4$ is pyridine substituted by phenyl wherein said phenyl is optionally substituted by lower alkyl.
10. A compound of claim 1 wherein $R^1$ is hydrogen, fluoro, chloro, bromo, methoxy, or phenyl and $R^2$ is hydrogen, fluoro, chloro, methyl, ethyl, propyl, or isopropyl; with the proviso that $R^1$ and $R^2$ are not both hydrogen.
11. A compound of claim 1 wherein $R^1$ is hydrogen, fluoro, chloro, or bromo and $R^2$ is hydrogen, fluoro, chloro, or methyl, ethyl, or isopropyl; with the proviso that $R^1$ and $R^2$ are not both hydrogen.

12. A compound of claim 1 wherein at least one of $R^1$ or $R^2$ is fluoro, chloro, or bromo.

13. A compound of claim 1 wherein $R^1$ is fluoro or chloro.

14. A compound of claim 1 wherein $R^4$ is phenyl substituted by two substituents at positions 3 and 5 on the phenyl ring where such positions are indicated below in formula IC:

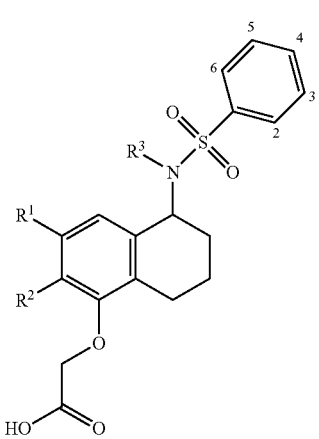

IC wherein $R^1$-$R^3$ are as defined in claim 1.

15. A compound of claim 14 wherein $R^1$ is fluoro or chloro; $R^2$ is hydrogen or fluoro; $R^3$ is hydrogen; and the phenyl ring is substituted at positions 3 and 5 as indicated in formula IC with substituents independently selected from the group consisting of fluoro, bromo, or trifluoromethyl.

16. A compound of claim 14 wherein $R^1$ is fluoro or chloro; $R^2$ is hydrogen or fluoro; $R^3$ is hydrogen; and the phenyl ring is substituted at positions 3 and 5 with trifluoromethyl.

17. A compound of claim 1 which is an (R)-enantiomer as depicted in formula IA:

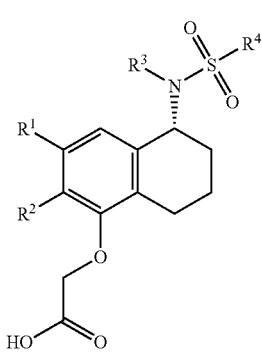

IA wherein $R^1$-$R^4$ are as defined in claim 1.

18. A compound of claim 1 selected from the group consisting of:

[(R)-5-(3,5-Bis-trifluoromethyl-benzenesulfonylamino)-2,3-dichloro-5,6,7,8-tetrahydro-naphthalen-1-yloxy]-acetic acid;

[5-(3,5-Bis-trifluoromethyl-benzenesulfonylamino)-2-isopropyl-5,6,7,8-tetrahydro-naphthalen-1-yloxy]-acetic acid;

[5-(3,5-Bis-trifluoromethyl-benzenesulfonylamino)-2-methyl-5,6,7,8-tetrahydro-naphthalen-1-yloxy]-acetic acid;

[5-(3,5-Bis-trifluoromethyl-benzenesulfonylamino)-2-ethyl-5,6,7,8-tetrahydro-naphthalen-1-yloxy]-acetic acid;

[5-(3,5-Bis-trifluoromethyl-benzenesulfonylamino)-3-chloro-2-methyl-5,6,7,8-tetrahydro-naphthalen-1-yloxy]-acetic acid;

[5-(3,5-Bis-trifluoromethyl-benzenesulfonylamino)-3-chloro-5,6,7,8-tetrahydro-naphthalen-1-yloxy]-acetic acid;

[5-(3,5-Bis-trifluoromethyl-benzenesulfonylamino)-2-chloro-5,6,7,8-tetrahydro-naphthalen-1-yloxy]-acetic acid;

[(R)-5-(3,5-Bis-trifluoromethyl-benzenesulfonylamino)-3-chloro-5,6,7,8-tetrahydro-naphthalen-1-yloxy]-acetic acid;

5-(3,5-Bis-trifluoromethyl-benzenesulfonylamino)-3-chloro-2-fluoro-5,6,7,8-tetrahydro-naphthalen-1-yloxy]-acetic acid; and

[3-Chloro-5-(2,5-dichloro-benzenesulfonylamino)-2-fluoro-5,6,7,8-tetrahydro-naphthalen-1-yloxy]-acetic acid;

or a pharmaceutically acceptable salt or ester thereof.

19. A compound of claim 1 selected from the group consisting of:

[3-Chloro-5-(2,4-dichloro-benzenesulfonylamino)-5,6,7,8-tetrahydro-naphthalen-1-yloxy]-acetic acid;

5-(3,5-Bis-trifluoromethyl-benzenesulfonylamino)-2,3-dichloro-5,6,7,8-tetrahydro-naphthalen-1-yloxy]-acetic acid;

[3-Chloro-5-(2,5-dichloro-benzenesulfonylamino)-5,6,7,8-tetrahydro-naphthalen-1-yloxy]-acetic acid;

[3-Chloro-5-(2,4-dichloro-benzenesulfonylamino)-2-fluoro-5,6,7,8-tetrahydro-naphthalen-1-yloxy]-acetic acid;

[5-(3-Bromo-5-trifluoromethyl-benzenesulfonylamino)-3-chloro-2-fluoro-5,6,7,8-tetrahydro-naphthalen-1-yloxy]-acetic acid;

[3-Chloro-5-(3-fluoro-5-trifluoromethyl-benzenesulfonylamino)-5,6,7,8-Tetrahydro-naphthalen-1-yloxy]-acetic acid;

[5-(3-Bromo-5-trifluoromethyl-benzenesulfonylamino)-3-chloro-5,6,7,8-tetrahydro-naphthalen-1-yloxy]-acetic acid;

[(R)-3-Chloro-5-(2,4-dichloro-benzenesulfonylamino)-5,6,7,8-tetrahydro-naphthalen-1-yloxy]-acetic acid;

[5-(3,5-Bis-trifluoromethyl-benzenesulfonylamino)-3-bromo-5,6,7,8-tetrahydro-naphthalen-1-yloxy]-acetic acid; and

[(R)-5-(3,5-Bis-trifluoromethyl-benzenesulfonylamino)-3-bromo-5,6,7,8-tetrahydro-naphthalen-1-yloxy]-acetic acid;

or a pharmaceutically acceptable salt or ester thereof.

20. A compound of claim 1 selected from the group consisting of:

[3-Chloro-2-fluoro-5-(3-fluoro-5-trifluoromethyl-benzenesulfonylamino)-5,6,7,8-tetrahydro-naphthalen-1-yloxy]-acetic acid;

[5-(3,5-Bis-trifluoromethyl-benzenesulfonylamino)-2-fluoro-5,6,7,8-tetrahydro-naphthalen-1-yloxy]-acetic acid;

[(R)-5-(3,5-Bis-trifluoromethyl-benzenesulfonylamino)-3-methoxy-5,6,7,8-tetrahydro-naphthalen-1-yloxy]-acetic acid;

[5-(3,5-Bis-trifluoromethyl-benzenesulfonylamino)-3-phenyl-5,6,7,8-tetrahydro-naphthalen-1-yloxy]-acetic acid;

[(R)-5-(3,5-Bis-trifluoromethyl-benzenesulfonylamino)-2-chloro-5,6,7,8-tetrahydro-naphthalen-1-yloxy]-acetic acid;

[2,3-Difluoro-5-(3-fluoro-5-trifluoromethyl-benzenesulfonylamino)-5,6,7,8-tetrahydro-naphthalen-1-yloxy]-acetic acid;

[3-Fluoro-5-(3-fluoro-5-trifluoromethyl-benzenesulfony-lamino)-5,6,7,8-tetrahydro-naphthalen-1-yloxy]-acetic acid;
[5-(3-Bromo-5-trifluoromethyl-benzenesulfonylamino)-3-fluoro-5,6,7,8-tetrahydro-naphthalen-1-yloxy]-acetic acid;
5-(3-Bromo-5-trifluoromethyl-benzenesulfonylamino)-2,3-difluoro-5,6,7,8-tetrahydro-naphthalen-1-yloxy]-acetic acid; and
[5-(2,4-Dichloro-benzenesulfonylamino)-2,3-difluoro-5,6,7,8-tetrahydro-naphthalen-1-yloxy]-acetic acid;
or a pharmaceutically acceptable salt or ester thereof.

21. A compound of claim 1 selected from the group consisting of:
[5-(2,4-Dichloro-benzenesulfonylamino)-3-fluoro-5,6,7,8-tetrahydro-naphthalen-1-yloxy]-acetic acid;
[5-(2,5-Dichloro-benzenesulfonylamino)-2,3-difluoro-5,6,7,8-tetrahydro-naphthalen-1-yloxy]-acetic acid;
[5-(2,5-Dichloro-benzenesulfonylamino)-3-fluoro-5,6,7,8-tetrahydro-naphthalen-1-yloxy]-acetic acid;
{2,3-Difluoro-5-[5-(3-isopropyl-phenyl)-pyridine-2-sulfonylamino]-5,6,7,8-tetrahydro-naphthalen-1-yloxy}-acetic acid;
{3-Fluoro-5-[5-(3-isopropyl-phenyl)-pyridine-2-sulfonylamino]-5,6,7,8-tetrahydro-naphthalen-1-yloxy}-acetic acid;
{3-Chloro-5-[5-(3-isopropyl-phenyl)-pyridine-2-sulfonylamino]-5,6,7,8-tetrahydro-naphthalen-1-yloxy}-acetic acid;
[(R)-3-Bromo-5-(3-bromo-5-trifluoromethyl-benzenesulfonylamino)-5,6,7,8-tetrahydro-naphthalen-1-yloxy]-acetic acid;
[(R)-3-Chloro-2-fluoro-5-(3-fluoro-5-trifluoromethyl-benzenesulfonylamino)-5,6,7,8-tetrahydro-naphthalen-1-yloxy]-acetic acid;
[(R)-5-(3-Bromo-5-trifluoromethyl-benzenesulfonylamino)-3-chloro-2-fluoro-5,6,7,8-tetrahydro-naphthalen-1-yloxy]-acetic acid; and
[(R)-3-Chloro-5-(2,4-dichloro-benzenesulfonylamino)-2-fluoro-5,6,7,8-tetrahydro-naphthalen-1-yloxy]-acetic acid;
or a pharmaceutically acceptable salt or ester thereof.

22. A compound of claim 1 selected from the group consisting of:
[(R)-3-Chloro-5-(3-fluoro-5-trifluoromethyl-benzenesulfonylamino)-5,6,7,8-tetrahydro-naphthalen-1-yloxy]-acetic acid;
[(R)-5-(3-Bromo-5-trifluoromethyl-benzenesulfonylamino)-3-chloro-5,6,7,8-tetrahydro-naphthalen-1-yloxy]-acetic acid;
[(R)-3-Chloro-5-(2,5-dichloro-benzenesulfonylamino)-5,6,7,8-tetrahydro-naphthalen-1-yloxy]-acetic acid;
{3-Chloro-2-fluoro-5-[5-(3-isopropyl-phenyl)-pyridine-2-sulfonylamino]-5,6,7,8-tetrahydro-naphthalen-1-yloxy}-acetic acid;
[5-(2,5-Dichloro-benzenesulfonylamino)-2-fluoro-5,6,7,8-tetrahydro-naphthalen-1-yloxy]-acetic acid;
[5-(2,4-Dichloro-benzenesulfonylamino)-2-fluoro-5,6,7,8-tetrahydro-naphthalen-1-yloxy]-acetic acid;
{2-Fluoro-5-[5-(3-isopropyl-phenyl)-pyridine-2-sulfonylamino]-5,6,7,8-tetrahydro-naphthalen-1-yloxy}-acetic acid;
[(R)-3-Bromo-5-(2,5-dichloro-benzenesulfonylamino)-5,6,7,8-tetrahydro-naphthalen-1-yloxy]-acetic acid;
[(R)-3-Bromo-5-(2,4-dichloro-benzenesulfonylamino)-5,6,7,8-tetrahydro-naphthalen-1-yloxy]-acetic acid; and
[5-(3,5-Bis-methanesulfonyl-benzenesulfonylamino)-3-bromo-5,6,7,8-tetrahydro-naphthalen-1-yloxy]-acetic acid;
or a pharmaceutically acceptable salt or ester thereof.

23. A compound of claim 1 selected from the group consisting of:
[5-(3,5-Bis-trifluoromethyl-benzenesulfonyl)-methyl-amino)-3-chloro-2-fluoro-5,6,7,8-tetrahydro-naphthalen-1-yloxy]-acetic acid;
{5-[(3,5-Bis-trifluoromethyl-benzenesulfonyl)-methyl-amino]-2-methyl-5,6,7,8-tetrahydro-naphthalen-1-yloxy}-acetic acid;
{5-[(3,5-Bis-trifluoromethyl-benzenesulfonyl)-methyl-amino]-2-ethyl-5,6,7,8-tetrahydro-naphthalen-1-yloxy}-acetic acid;
{5-[(3,5-Bis-trifluoromethyl-benzenesulfonyl)-methyl-amino]-3-chloro-5,6,7,8-tetrahydro-naphthalen-1-yloxy}-acetic acid;
{(R)-5-[(3,5-Bis-trifluoromethyl-benzenesulfonyl)-methyl-amino]-3-chloro-5,6,7,8-tetrahydro-naphthalen-1-yloxy}-acetic acid;
{3-Chloro-5-[(2,4-dichloro-benzenesulfonyl)-methyl-amino]-5,6,7,8-tetrahydro-naphthalen-1-yloxy}-acetic acid;
{5-[(3,5-Bis-trifluoromethyl-benzenesulfonyl)-methyl-amino]-2,3-dichloro-5,6,7,8-tetrahydro-naphthalen-1-yloxy}-acetic acid;
{5-[(3,5-Bis-trifluoromethyl-benzenesulfonyl)-methyl-amino]-3-chloro-2-methyl-5,6,7,8-tetrahydro-naphthalen-1-yloxy}-acetic acid;
{3-Chloro-5-[(2,5-dichloro-benzenesulfonyl)-methyl-amino]-2-fluoro-5,6,7,8-tetrahydro-naphthalen-1-yloxy}-acetic acid; and
{3-Chloro-5-[(2,5-dichloro-benzenesulfonyl)-methyl-amino]-5,6,7,8-tetrahydro-naphthalen-1-yloxy}-acetic acid;
or a pharmaceutically acceptable salt or ester thereof.

24. A compound of claim 1 selected from the group consisting of:
{3-Chloro-5-[(2,4-dichloro-benzenesulfonyl)-methyl-amino]-2-fluoro-5,6,7,8-tetrahydro-naphthalen-1-yloxy}-acetic acid;
{5-[(3-Bromo-5-trifluoromethyl-benzenesulfonyl)-methyl-amino]-3-chloro-2-fluoro-5,6,7,8-tetrahydro-naphthalen-1-yloxy}-acetic acid;
{5-[(3-Bromo-5-trifluoromethyl-benzenesulfonyl)-methyl-amino]-3-chloro-5,6,7,8-tetrahydro-naphthalen-1-yloxy}-acetic acid;
{3-Chloro-5-[(3-fluoro-5-trifluoromethyl-benzenesulfonyl)-methyl-amino]-5,6,7,8-tetrahydro-naphthalen-1-yloxy}-acetic acid;
{3-Chloro-2-fluoro-5-[(3-fluoro-5-trifluoromethyl-benzenesulfonyl)-methyl-amino]-5,6,7,8-tetrahydro-naphthalen-1-yloxy}-acetic acid;
{5-[(2,4-Dichloro-benzenesulfonyl)-methyl-amino]-3-fluoro-5,6,7,8-tetrahydro-naphthalen-1-yloxy}-acetic acid;
{5-[(3,5-Bis-trifluoromethyl-benzenesulfonyl)-methyl-amino]-2-fluoro-5,6,7,8-tetrahydro-naphthalen-1-yloxy}-acetic acid;
{5-[(2,4-Dichloro-benzenesulfonyl)-methyl-amino]-2,3-difluoro-5,6,7,8-tetrahydro-naphthalen-1-yloxy}-acetic acid;
{5-[(2,5-Dichloro-benzenesulfonyl)-methyl-amino]-3-fluoro-5,6,7,8-tetrahydro-naphthalen-1-yloxy}-acetic acid; and {5-[(3-Bromo-5-trifluoromethyl-benzenesulfonyl)-methyl-amino]-2,3-difluoro-5,6,7,8-tetrahydro-naphthalen-1-yloxy}-acetic acid;

or a pharmaceutically acceptable salt or ester thereof.

25. A compound of claim 1 selected from the group consisting of:

{5-[(2,5-Dichloro-benzenesulfonyl)-methyl-amino]-2,3-difluoro-5,6,7,8-tetrahydro-naphthalen-1-yloxy}-acetic acid;

{5-[(3-Bromo-5-trifluoromethyl-benzenesulfonyl)-methyl-amino]-3-fluoro-5,6,7,8-tetrahydro-naphthalen-1-yloxy}-acetic acid;

{3-Fluoro-5-[(3-fluoro-5-trifluoromethyl-benzenesulfonyl)-methyl-amino]-5,6,7,8-tetrahydro-naphthalen-1-yloxy}-acetic acid;

{2,3-Difluoro-5-[(3-fluoro-5-trifluoromethyl-benzenesulfonyl)-methyl-amino]-5,6,7,8-tetrahydro-naphthalen-1-yloxy}-acetic acid;

(2,3-Difluoro-5-{[5-(3-isopropyl-phenyl)-pyridine-2-sulfonyl]-methyl-amino}-5,6,7,8-tetrahydro-naphthalen-1-yloxy)-acetic acid;

(3-Fluoro-5-{[5-(3-isopropyl-phenyl)-pyridine-2-sulfonyl]-methyl-amino}-5,6,7,8-tetrahydro-naphthalen-1-yloxy)-acetic acid;

(3-Chloro-5-{[5-(3-isopropyl-phenyl)-pyridine-2-sulfonyl]-methyl-amino}-5,6,7,8-tetrahydro-naphthalen-1-yloxy)-acetic acid;

(3-Chloro-2-fluoro-5-{[5-(3-isopropyl-phenyl)-pyridine-2-sulfonyl]-methyl-amino}-5,6,7,8-tetrahydro-naphthalen-1-yloxy)-acetic acid;

{5-[(2,5-Dichloro-benzenesulfonyl)-methyl-amino]-2-fluoro-5,6,7,8-tetrahydro-naphthalen-1-yloxy}-acetic acid;

{5-[(2,4-Dichloro-benzenesulfonyl)-methyl-amino]-2-fluoro-5,6,7,8-tetrahydro-naphthalen-1-yloxy}-acetic acid; and (2-Fluoro-5-{[5-(3-isopropyl-phenyl)-pyridine-2-sulfonyl]-methyl-amino}-5,6,7,8-tetrahydro-naphthalen-1-yloxy)-acetic acid;

or a pharmaceutically acceptable salt or ester thereof.

26. A pharmaceutical composition comprising a therapeutically effective amount of a compound according to claim 1 and a pharmaceutically acceptable carrier.

\* \* \* \* \*